US011499165B2

(12) United States Patent
Deverman et al.

(10) Patent No.: US 11,499,165 B2
(45) Date of Patent: Nov. 15, 2022

(54) TARGETING PEPTIDES FOR DIRECTING ADENO-ASSOCIATED VIRUSES (AAVS)

(71) Applicant: CALIFORNIA INSTITUTE OF TECHNOLOGY, Pasadena, CA (US)

(72) Inventors: Benjamin E. Deverman, Pasadena, CA (US); Viviana Gradinaru, Flintridge, CA (US); Ken Y. Chan, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 555 days.

(21) Appl. No.: 15/374,596

(22) Filed: Dec. 9, 2016

(65) Prior Publication Data

US 2017/0166926 A1 Jun. 15, 2017

Related U.S. Application Data

(60) Provisional application No. 62/266,184, filed on Dec. 11, 2015, provisional application No. 62/421,891, filed on Nov. 14, 2016.

(51) Int. Cl.
| | | |
|---|---|---|
| *C12N 15/86* | (2006.01) | |
| *C07K 14/015* | (2006.01) | |
| *A61K 38/08* | (2019.01) | |
| *C07K 14/005* | (2006.01) | |
| *C12N 7/00* | (2006.01) | |
| *C07K 7/06* | (2006.01) | |
| *A61K 38/00* | (2006.01) | |
| *A61K 38/02* | (2006.01) | |
| *A61K 38/17* | (2006.01) | |
| *A61K 38/18* | (2006.01) | |
| *A61K 38/20* | (2006.01) | |
| *A61K 38/43* | (2006.01) | |
| *A61K 38/47* | (2006.01) | |
| *A61K 38/48* | (2006.01) | |
| *A61K 38/50* | (2006.01) | |
| *A61K 48/00* | (2006.01) | |
| *C07K 16/18* | (2006.01) | |
| *C12N 15/113* | (2010.01) | |

(52) U.S. Cl.
CPC ............. *C12N 15/86* (2013.01); *A61K 38/08* (2013.01); *C07K 7/06* (2013.01); *C07K 14/005* (2013.01); *C07K 14/015* (2013.01); *C12N 7/00* (2013.01); *A61K 38/00* (2013.01); *A61K 38/02* (2013.01); *A61K 38/1709* (2013.01); *A61K 38/185* (2013.01); *A61K 38/2093* (2013.01); *A61K 38/43* (2013.01); *A61K 38/47* (2013.01); *A61K 38/4813* (2013.01); *A61K 38/50* (2013.01); *A61K 48/00* (2013.01); *C07K 16/18* (2013.01); *C07K 2319/00* (2013.01); *C12N 15/113* (2013.01); *C12N 15/1137* (2013.01); *C12N 2310/122* (2013.01); *C12N 2310/141* (2013.01); *C12N 2320/32* (2013.01); *C12N 2330/51* (2013.01); *C12N 2750/14141* (2013.01); *C12N 2750/14142* (2013.01); *C12N 2750/14143* (2013.01); *C12N 2750/14171* (2013.01); *C12Y 302/0102* (2013.01); *C12Y 304/14009* (2013.01); *C12Y 305/01015* (2013.01)

(58) Field of Classification Search
CPC ...... C12N 15/86; C12N 7/00; C12N 2330/51; C12N 2750/14141; C12N 2750/14143; A61K 38/08; A61K 38/02; A61K 38/1709; A61K 48/00; C07K 14/005; C07K 14/015; C07K 2319/00; C07K 7/06
USPC ....... 435/320.1; 424/199.1, 233.1; 514/44 R; 530/327
See application file for complete search history.

(56) References Cited

U.S. PATENT DOCUMENTS

| | | | |
|---|---|---|---|
| 5,919,676 A | 7/1999 | Graham et al. | |
| 6,228,646 B1 | 5/2001 | Hardy | |
| 6,274,354 B1 | 8/2001 | Wilson et al. | |
| 6,379,943 B1 | 4/2002 | Graham et al. | |
| 6,410,271 B1 | 6/2002 | Zhu et al. | |
| 9,018,138 B2 | 4/2015 | Lupoid et al. | |
| 9,585,971 B2 * | 3/2017 | Deverman | C12N 15/1068 |
| 9,957,303 B2 | 5/2018 | Deverman et al. | |
| 10,202,425 B2 | 2/2019 | Deverman et al. | |
| 10,301,360 B2 | 5/2019 | Deverman et al. | |
| 10,519,198 B2 | 12/2019 | Deverman et al. | |
| 2002/0058325 A1 | 5/2002 | Hardy | |
| 2007/0036760 A1 | 2/2007 | Wilson et al. | |
| 2007/0172460 A1 | 7/2007 | Kleinschmidt et al. | |
| 2009/0042257 A1 | 2/2009 | Rodriguez | |

(Continued)

FOREIGN PATENT DOCUMENTS

| | | |
|---|---|---|
| CN | 101182534 A | 5/2008 |
| CN | 110913866 A | 3/2020 |

(Continued)

OTHER PUBLICATIONS

Michelfelder et al. (2011) PLoS ONE, vol. 6(8), e23101.doi:10.1371/journal. pone.0023101, pp. 1-11.*
Wu et al. Journal of Virology (2000) vol. 74, No. 18, 8635-8647.*
Deverman et al., "Cre-dependent selection yields AAV variants for widespread gene transfer to the adult brain," Nature Biotechnology, Feb. 1, 2016, vol. 34, No. 2, pp. 204-209.

(Continued)

*Primary Examiner* — Anne Marie S Wehbe
(74) *Attorney, Agent, or Firm* — Sheppard, Mullin, Richter & Hampton LLP

(57) ABSTRACT

Disclosed herein are peptide sequences capable of directing adeno-associated viruses (AAV) to target specific environments, for example the nervous system and the heart, in a subject. Also disclosed are AAVs having non-naturally occurring capsid proteins comprising the disclosed peptide sequences, and methods of using the AAVs to treat diseases.

6 Claims, 38 Drawing Sheets

Specification includes a Sequence Listing.

(56) References Cited

U.S. PATENT DOCUMENTS

| | | |
|---|---|---|
| 2009/0202490 A1 | 8/2009 | Schaffer et al. |
| 2010/0105123 A2 | 4/2010 | Halek et al. |
| 2011/0223635 A1 | 9/2011 | Deisseroth et al. |
| 2013/0059732 A1 | 3/2013 | Lisowski et al. |
| 2013/0142764 A1 | 6/2013 | Davidson et al. |
| 2013/0195801 A1 | 8/2013 | Gao et al. |
| 2015/0079038 A1* | 3/2015 | Deverman ......... C12N 15/1068 424/93.2 |
| 2015/0315612 A1 | 11/2015 | Wilson et al. |
| 2017/0166926 A1 | 6/2017 | Deverman et al. |
| 2017/0204144 A1 | 7/2017 | Deverman et al. |
| 2017/0240885 A1 | 8/2017 | Deverman et al. |
| 2019/0144509 A1 | 5/2019 | Deverman et al. |
| 2019/0292230 A1 | 9/2019 | Deverman et al. |

FOREIGN PATENT DOCUMENTS

| | | |
|---|---|---|
| CN | 110914427 A | 3/2020 |
| CN | 111108198 A | 5/2020 |
| CN | 111448308 A | 7/2020 |
| EP | 1290205 | 3/2006 |
| EP | 3561062 | 10/2019 |
| JP | 2014-518614 | 8/2014 |
| RU | 2457252 | 7/2012 |
| WO | WO 2001/092551 | 12/2001 |
| WO | WO 2005/017101 | 2/2005 |
| WO | WO2008103993 | 8/2008 |
| WO | WO 2009/012176 | 1/2009 |
| WO | WO 2012/145601 A2 | 10/2012 |
| WO | WO2015040002 | 3/2015 |
| WO | WO 2015/168666 | 11/2015 |
| WO | WO2015168666 | 11/2015 |
| WO | WO 2017/100671 A1 | 6/2017 |

OTHER PUBLICATIONS

International Search Report and Written Opinion dated Mar. 28, 2017 for International Patent Application No. PCT/US2016/065969 filed Dec. 9, 2016, 18 pages.
Communication pursuant to Article 94(3) EPC issued by the European Patent Office dated Jan. 31, 2018 in EP 14 843 244.6-111.
Database UniProt [Online] Jan. 9, 2013, Uncharacterized protein ECO:0000313 Ensembl:ENSPSIP00000004403, EBI accession No. UNIPROT:K7F8P3.
Office Action dated Feb. 8, 2018 in U.S. Appl. No. 15/422,259, filed Feb. 1, 2017.
Extended European Search Report dated May 9, 2019 for European Application No. 16873985.2.
Office Action dated May 15, 2019 for Russian Application No. 2018120736, filed Jul. 11, 2018.
Office Action dated May 31, 2019 in U.S. Appl. No. 16/222,549, filed Dec. 17, 2018.
Albert et al., "Site-specific integration of DNA into wild-type and mutant lox sites placed in the plant genome," The Plant Journal: for cell and molecular biology, 1995, vol. 7(4), pp. 649-659.
Araki, K. et al., "Targeted integration of DNA using mutant lox sites in embryonic stem cells," Nucleic Acids Res, 1997, vol. 25, pp. 868-872.
Aschauer, D.F. et al., "Analysis of transduction efficiency, tropism and axonal transport of AAV serotypes 1, 2, 5, 6, 8 and 9 in the mouse brain," 2013, PLoS One 8(9), e76310, 16 pages, doi:10.1371/journal.pone.0076310.
Asokan, A. et al., "The AAV Vector Toolkit: Poised at the Clinical Crossroads," Molecular Therapy : the Journal of the American Society of Gene Therapy, 2012, 20(4):699-708.
Asokan, A., "Reengineered AAV vectors: old dog, new tricks," Discovery medicine, 2010, vol. 9, pp. 399-403.
Ayuso, E. et al., "High AAV vector purity results in serotype- and tissue-independent enhancement of transduction efficiency," Gene Therapy, 2010, vol. 17(4), pp. 503-510, doi:10.1038/gt.2009.157.

Balazs, A.B. et al., Antibody-based protection against HIV infection by vectored immunoprophylaxis, Nature, 2011, vol. 481, No. 7379, pp. 81-84, doi:doi:10.1038/nature10660.
Balazs, A.B. et al., "Broad protection against influenza infection by vectored immunoprophylaxis in mice," Nature Biotechnology, Jul. 31, 2013 (7):647-52. doi:10.1038/nbt.2618.
Bartel, M. et al., "Enhancing the Clinical Potential of AAV Vectors by Capsid Engineering to Evade Pre-Existing Immunity," Frontiers in Microbiology, 2011, vol. 2, Article 204, 10 pages, doi 10.3389/fmicb.2011.00204.
Bartlett, J.S. et al., "Selective and rapid uptake of adeno-associated virus type 2 in brain," Human Gene Therapy, Mar. 1998, vol. 9, No. 8, pp. 1181-1186, doi: 10.1089/hum.1998.9.8-1181.
Bartlett, J.S. et al., "Targeted adeno-associated virus vector transduction of nonpermissive cells mediated by a bispecific F(ab'gamma)2 antibody," Nat Biotechnol, 1999, vol. 17, pp. 181-186, doi:10.1038/6185.
Betley, J.N. et al., "Adeno-associated viral vectors for mapping, monitoring, and manipulating neural circuits," Hum Gene Ther, 2011, vol. 22, pp. 669-677, doi:10.1087/hum.2010.204.
Bevan, A.K. et al., "Systemic gene delivery in large species for targeting spinal cord, brain, and peripheral tissues for pediatric disorders," Molecular therapy : the journal ofthe American Society of Gene Therapy, 2011, vol. 19, pp. 1971-1980, doi:10.1038/mt.2011.157.
Borel, F. et al., "Recombinant AAV as a platform for translating the therapeutic potential of RNA interference," Molecular Therapy : the Journal ofthe American Society of Gene Therapy, 2014, vol. 22, pp. 692-701, doi:10.1038/mt.2013.285.
Boudreau, R.L. et al., "Nonallele-specific silencing of mutant and wild-type huntingtin demonstrates therapeutic efficacy in Huntington's disease mice," Molecular therapy : the journal ofthe American Society of Gene Therapy, 2009, vol. 17, pp. 1053-1063, doi:10.1038/mt.2009.17.
Boutin, S. et al., "Prevalence of serum IgG and neutralizing factors against adeno-associated virus (AAV) types 1, 2, 5, 6, 8, and 9 in the healthy population: implications for gene therapy using AAV vectors," Hum Gene Ther, 2010, vol. 21, pp. 704-712, doi:10.1089/hum.2009.182.
Calcedo, R. et al., "Worldwide epidemiology of neutralizing antibodies to adeno-associated viruses," J Infect Dis, 2009, vol. 199, pp. 381-390, doi:10.1086/595830.
Callaway, E.M., "Transneuronal circuit tracing with neurotropic viruses," Curr Opin Neurobiol, 2008, vol. 18, pp. 617-623.
Castle et al., "Long-distance axonal transport of AAV9 is driven by dynein and kinesin-2 and is trafficked in a highly motile Rab7-positive compartment," Molecular Therapy, 2014, vol. 22, pp. 554-566.
Castle, M.J. et al., "Adeno-Associated Virus Serotypes 1, 8, and 9 Share Conserved Mechanisms for Anterograde and Retrograde Axonal Transport," Hum Gene Ther., 2014, 25(8), pp. 705-720.
Cearley, C.N. et al., "A single injection of an adeno-associated virus vector into nuclei with divergent connections results in widespread vector distribution in the brain and global correction of a neurogenetic disease," The Journal of Neuroscience : the official journal ofthe Society for Neuroscience, 2007, vol. 27, pp. 9928-9940.
Chakrabarty, P., et al., "Capsid serotype and timing of injection determines AAV transduction in the neonatal mice brain," PLoS One, 2013, vol. 8, pp. e67680, doi:10.1371/journal.pone.0067680.
Chiorini, J.A. et al., Cloning and characterization of adeno-associated virus type, J. Virol., 1999, vol. 73, pp. 1309-1319.
Chung, K. et al., "CLARITY for mapping the nervous system," Nat Methods, 2013, vol. 10, No. 6, pp. 508-513.
Dalkara, D. et al., "In vivo-directed evolution of a new adeno-associated virus for therapeutic outer retinal gene delivery from the vitreous," Science translational medicine, 2013, vol. 5, No. 189, pp. 189ra176, doi: 10.1126/scitranslmed.3005708.
Dufour, B.D., et al., "Intrajugular vein delivery of AAV9-RNAi prevents neuropathological changes and weight loss in Huntington's disease mice," Molecular therapy : the journal of the American Society of Gene Therapy, 2014, vol. 22, pp. 797-810, doi:10.1038/mt.2013.289.

(56) References Cited

OTHER PUBLICATIONS

Duque, S. et al., "Intravenous Administration of Self-complementary AAV9 Enables Transgene Delivery to Adult Motor Neurons," Molecular therapy : the journal of the American Society of Gene Therapy, 2009, vol. 17, pp. 1187-1196.
European Search Report dated Jan. 20, 2017 for European Patent Application No. 14843244.6, in 6 pages.
Excoffon, K.J.D.A. et al., "Directed evolution of adeno-associated virus to an infectious respiratory virus," Proceedings of the National Academy of Sciences of the United States of America, 2009, vol. 106, No. 10, pp. 3865-3870, doi:10.1073/pnas.0813365106.
Farris et al., "Improved splicing of adeno-associated viral (AAV) capsid protein-supplying pre-mRNAs leads to increased recombinant AAV vector production," Human Gene Therapy, 2008, vol. 19, pp. 1421-1427.
Fenno, L. et al., "The development and application of optogenetics," Annual review of neuroscience, 2011, vol. 34, pp. 389-412.
Fenno, L.E. et al., "Targeting cells with single vectors using multiple-feature Boolean logic," Nat Methods, 2014, vol. 11, pp. 763-772.
Flotte et al., "Adeno-associated virus vectors for gene therapy of cystic fibrosis," Methods Enzymol, 1998, vol. 292, pp. 717-732.
Foust, K.D. et al., "Intravascular AAV9 preferentially targets neonatal neurons and adult astrocytes," Nature biotechnology, 2009, vol. 27, pp. 59-65.
Foust, K.D. et al., "Rescue of the spinal muscular atrophy phenotype in a mouse model by early postnatal delivery of SMN," Nat Biotechnol, 2010, vol. 28, pp. 271-274, doi:10.1038/nbt.1610.
Foust, K.D. et al., "Therapeutic AAV9-mediated Suppression of Mutant SOD1 Slows Disease Progression and Extends Survival in Models of Inherited ALS," Molecular therapy: the journal of the American Society of Gene Therapy, 2013, vol. 21, No. 12, pp. 2148-2159, doi:10.1038/mt.2013.211.
Garcia, A.D.R et al., "GFAP-expressing progenitors are the principal source of constitutive neurogenesis in adult mouse forebrain," Nature neuroscience, 2004, vol. 7, pp. 1233-1241, doi:10.1038/nn1340.
Garg, S.K. et al., "Systemic Delivery of MeCP2 Rescues Behavioral and Cellular Deficits in Female Mouse Models of Rett Syndrome," The Journal of neuroscience : the official journal of the Society for Neuroscience, 2013, vol. 33, pp. 13612-13620, doi:10.1523/JNEUROSCI.1854-13.2013.
Gaudet, D. et al., "Review of the clinical development of alipogenetiparvovec gene therapy for lipoprotein lipase deficiency," Atherosclerosis Supplements 2010, vol. 11, pp. 55-60, doi:10.1016/j.atherosclerosissup.2010.03.004.
Gibson et al., "Enzymatic assembly of DNA molecules up to several hundred kilobases," Nature Methods, 2009, vol. 6(5), pp. 343-345.
Gray, S.J. et al., "Directed Evolution of a Novel Adeno-associated Virus (AAV) Vector That Crosses the Seizure-compromised Blood-Brain Barrier (BBB)," Molecular therapy : the journal of the American Society of Gene Therapy, 2009, vol. 18, pp. 570-578.
Gray, S.J. et al., "Preclinical Differences of Intravascular AAV9 Delivery to Neurons and Glia: A Comparative Study of Adult Mice and Nonhuman Primates," Molecular therapy : the journal of the American Society of Gene Therapy, 2011, vol. 19, pp. 1058-1069.
Gray, S. J. et al., "Production of recombinant adeno-associated viral vectors and use in in vitro and in vivo administration," Current Protocols in Neuroscience / Editorial Board, Jacqueline N. Crawley . . . [ et al.], 2011, Chapter 4, Unit 4.17, p. 4.17.1-4.17.30, doi:10.1002/0471142301.ns0417s57.
Grieger, J. C. et al., "Production and characterization of adeno-associated viral vectors," Nature Protocols, 2006, vol. 1(3), pp. 1412-1428, doi:10.1038/nprot.2006.207.
Grimm, D. et al., "In vitro and in vivo gene therapy vector evolution via multispecies interbreeding and retargeting of adeno-associated viruses," Journal of virology, 2008, vol. 82, pp. 5887-5911.

Guenthner, C.J., et al., "Permanent genetic access to transiently active neurons via TRAP: targeted recombination in active populations," Neuron, 2013, vol. 78, pp. 773-784, doi:10.1016/j.neuron.2013.03.025.
Hancock, J.F. et al., "A CAAX or a CAAL motif and a second signal are sufficient for plasma membrane targeting of ras proteins," EMBO J., 1991, vol. 10, pp. 4033-4039.
High, K.H., et al., "Current status of haemophilia gene therapy," Haemophilia : the official journal of the World Federation of Hemophilia, 2014, 20 Suppl. 4, pp. 43-49, doi: 10.1111/hae.12411.
Hirt, B., "Selective extraction of polyoma DNA from infected mouse cell cultures," Journal of Molecular Biology, 1967, vol. 26(2), pp. 365-369.
Hutson, T.H. et al., "Corticospinal tract transduction: a comparison of seven adeno-associated viral vector serotypes and a non-integrating lentiviral vector," Gene therapy, 2012, vol. 19, pp. 49-60.
Inagaki, K. et al., "Frequency and spectrum of genomic integration of recombinant adeno-associated virus serotype 8 vector in neonatal mouse liver," J Virol, 2008, vol. 82, pp. 9513-9524.
Inagaki, K. et al., "Robust systemic transduction with AAV9 vectors in mice: efficient global cardiac gene transfer superior to that of AAV8," Molecular therapy : the journal of the American Society of Gene Therapy, 2006, vol. 14, pp. 45-53, doi:10.1016/j.ymthe.2006.03.014.
International Preliminary Report on Patentability dated Mar. 15, 2016 for International Patent Application No. PCT/US2014/055490 filed Sep. 12, 2014, 10 pages.
International Search Report and Written Opinion dated Dec. 24, 2014 for International Patent Application No. PCT/US2014/055490 filed Sep. 12, 2014, 18 pages.
Izpisua Belmonte, J.C., et al., "Brains, genes, and primates," Neuron, 2015, vol. 86, pp. 617-631, doi:10.1016/j.neuron.2015.03.021.
Kaeppel, C. et al., "A largely random AAV integration profile after LPLD gene therapy," Nat Med, 2013, vol. 19, pp. 889-891.
Kaplitt et al., "Long-term gene expression and phenotypic correction using adeno-associated virus vectors in the mammalian brain," Nature, 1994, vol. 8, pp. 148-154.
Kaplitt, M.G. et al., "Safety and tolerability of gene therapy with an adeno-associated virus (AAV) borne GAD gene for Parkinson 's disease: an open label, phase I trial," Lancet, 2007, vol. 369, pp. 2097-2105.
Kawashima, T., et al., "Functional labeling of neurons and their projections using the synthetic activity-dependent promoter E-SARE," Nat Methods, 2013, vol. 10, pp. 889-895, doi:10.1038/nmeth.2559.
Kessler et al., "Gene delivery to skeletal muscle results in sustained expression and systemic delivery of a therapeutic protein," Proceedings of the National Academy of Sciences USA, 1996, vol. 93, pp. 14082-14087.
Knipe, D. et al., "Fields of virology," edition (2006), 2007, Section 57, vol. II (Lippincott Williams & Wilkins), pp. 2107-2185.
Koerber, J.T. et al., "Construction of diverse adeno-associated viral libraries for directed evolution of enhanced gene delivery vehicles," Nature protocols, 2006, vol. 1, pp. 701-706.
Levitt, N. et al., "Definition of an efficient synthetic poly(A) site," Genes and Development, 1989, vol. 3, pp. 1019-1025.
Limberis, M.P. et al., "Intranasal antibody gene transfer in mice and ferrets elicits broad protection against pandemic influenza," Sci Transl Med, 2013, 5(187):187ra72, 10 pages.
Lisowski, L. et al., "Selection and evaluation of clinically relevant AAV variants in a xenograft liver model," Nature, 2014, vol. 506, pp. 382-386.
Löw, K. et al., "Direct and retrograde transduction of nigral neurons with AAV6, 8, and 9 and intraneuronal persistence of viral particles," Human gene therapy, 2013, vol. 24, pp. 613-629.
Luo, L. et al., "Genetic dissection of neural circuits," Neuron, 2008, vol. 57, pp. 634-660.
Maguire, A.M. et al., "Safety and efficacy of gene transfer for Leber's congenital amaurosis," N Engl J Med, 2008, vol. 358, pp. 2240-2248, doi:10.1056/NEJMoa0802315.
Maguire, C. A. et al., Directed evolution of adeno-associated virus for glioma cell transduction, Journal of neuro-oncology, 2010, vol. 96, No. 3, pp. 337-347, doi:10.1007/s11060-009-9972-7.

(56) References Cited

OTHER PUBLICATIONS

Maguire, C.A., et al., "Gene therapy for the nervous system: challenges and new strategies," Neurotherapeutics, 2014, vol. 11, pp. 817-839, doi:10.1007/s13311-014-0299-5.
Maheshri, N. et al., "Directed evolution of adeno-associated virus yields enhanced gene delivery vectors," Nature biotechnology, 2006, vol. 24, No. 2, pp. 198-204, doi:10.1038/nbt1182.
Marshel, J.H. et al., "Targeting single neuronal networks for gene expression and cell labeling in vivo," Neuron, 2010, vol. 67, pp. 562-574.
Martino, A.T. et al., "The genome of self-complementary adeno-associated viral vectors increases Toll-like receptor 9-dependent innate immune responses in the liver," Blood, 2011, vol. 117, pp. 6459-6468.
McBride, J.L. et al., "Preclinical safety of RNAi-mediated HTT suppression in the rhesus macaque as a potential therapy for Huntingtons disease," Molecular Therapy : the Journal of the American Society of Gene Therapy, 2011, vol. 19, pp. 2152-2162.
McCarty, D.M., "Self-complementary AAV vectors; advances and applications," Molecular Therapy : the Journal ofthe American Society of Gene Therapy, 2008, vol. 16, pp. 1648-1656.
MGI Mouse Genome Informatics Web Site. Available at http://www.informatics.jax.org in some form no later than Aug. 6, 2014. While no copy of the website as it existed on Aug. 6, 2014 is in Applicant's possession, Applicant has provided the website that was printed on Jan. 22, 2015, 1 page.
Mittermeyer, G. et al., "Long-term evaluation of a phase 1 study of AADC gene therapy for Parkinson's disease," Hum Gene Ther, 2012, vol. 23, pp. 377-381.
Muller, O.J., et al., "Random peptide libraries displayed on adeno-associated virus to select for targeted gene therapy vectors," Nat Biotechnol, 2003, vol. 21, pp. 1040-1046, doi:10.1038/nbt856.
Nathwani, A. C. et al., "Adenovirus-associated virus vector-mediated gene transfer in hemophilia B," The New England Journal of Medicine, 2011, vol. 365, No. 25, pp. 2357-2365, doi:10.1056/NEJMoa1108046.
Nathwani, A.C. et al., "Long-term safety and efficacy following systemic administration of a self-complementary AAV vector encoding human FIX pseudotyped with serotype 5 and 8 capsid proteins," Molecular therapy : the journal of the American Society of Gene Therapy, 2011, vol. 19, pp. 876-885, doi:10.1038/mt.2010.274.
National Institute of Health. Advisory Committee to the Director, Interim Report: Brain Research Through Advancing Innovation Neurotechnologies (BRAIN) Working Group, Sep. 16, 2013, pp. 1-58.
Nowrouzi, A. et al., "Integration frequency and intermolecular recombination of rAAV vectors in non-human primate skeletal muscle and liver," Mol Ther, 2012, vol. 20, pp. 1177-1186.
Ojala, D.S., et al., "Adeno-associated virus vectors and neurological gene therapy," Neuroscientist, 2015, vol. 21, pp. 84-98, doi: 10.1177/1073858414521870.
Osakada, F. et al., "New rabies virus variants for monitoring and manipulating activity and gene expression in defined neural circuits," Neuron, 2011, vol. 71, pp. 617-631.
Pasca, A.M., et al., "Functional cortical neurons and astrocytes from human pluripotent stem cells in 3D culture," Nature methods, 2015, vol. 12, pp. 671-678, doi:10.1038/nmeth.3415.
Perdomini, M. et al., "Prevention and reversal of severe mitochondrial cardiomyopathy by gene therapy in a mouse model of Friedreich's ataxia," Nat. Med., 2014, vol. 20, pp. 542-547, doi:10.1038/nm.3510.
Pulicherla, N. et al., "Engineering Liver-detargeted AAV9 Vectors for Cardiac and Musculoskeletal Gene Transfer," Molecular Therapy: the Journal of the American Society of Gene Therapy, 2011, vol. 19, pp. 1070-1078, doi:10.1038/mt.2011.22.
Qiu et al., "Characterization ofthe Transcription Profile of Adeno-Associated Virus Type 5 Reveals a Number of Unique Features Compared to Previously Characterized Adeno-Associated Viruses," Journal of Virology., 2002, vol. 76, pp. 12435-12447.

Salegio, E.A. et al., "Axonal transport of adeno-associated viral vectors is serotype-dependent," Gene Ther, 2013, vol. 20, pp. 348-352.
Samaranch et al., "AAV9 Transduction in The Central Nervous System of Non-Human Primates," Human gene therapy, 2011, vol. 22, pp. 329-337.
Samaranch, L. et al., "Adeno-associated virus serotype 9 transduction in the central nervous system of nonhuman primates," Hum Gene Ther, 2012, vol. 23, pp. 382-389, doi:10.1089/hum.2011.200.
Sambrook et al., "Molecular Cloning: A Laboratory Manual," 2nd Ed., Cold Spring Harbor Laboratory Press, Cold Spring Harbor, N.Y., 1989, 39 pages.
Savitt et al., "Bcl-x Is Required for Proper Development ofthe Mouse Substantia Nigra," The Journal of Neuroscience, 2005, vol. 25, pp. 6721-6728.
Schaffer, D.V. et al., "Molecular Engineering of Viral Gene Delivery Vehicles," Annual Review of Biomedical Engineering, 2008, vol. 10, pp. 169-194.
Schuster, D.J. et al., "Biodistribution of adeno-associated virus serotype 9 (AAV9) vector after intrathecal and intravenous delivery in mouse," Front Neuroanat, 2014, vol. 8, Article 42, 14 pages, doi:10.3389/fnana.2014.00042.
Shaner, N.C. et al., "A bright monomeric green fluorescent protein derived from Branchiostoma lanceolatum," Nat Methods, 2013, vol. 10, pp. 407-409.
Simonelli, F. et al., "Gene Therapy for Leber's Congenital Amaurosis is Safe and Effective Through 1.5 Years After Vector Administration," Molecular Therapy : the Journal ofthe American Society of Gene Therapy, 2009, vol. 18(3), pp. 643-650, doi:10.1038/mt.2009.277.
Smith, A.D et al., "The neural network ofthe basal ganglia as revealed by the study of synaptic connections of identified neurones," Trends Neurosci, 1990, vol. 13, pp. 259-265.
Sonntag, F. et al., "A viral assembly factor promotes AAV2 capsid formation in the nucleolus," Proceedings ofthe National Academy of Sciences ofthe United States of America, 2010, vol. 107, pp. 10220-10225, doi:10.1073/pnas.1001673107.
Southwell, A.L. et al., "Intrabody gene therapy ameliorates motor, cognitive, and neuropathological symptoms in multiple mouse models of Huntington's disease," The Journal of Neuroscience : the official journal of the Society for Neuroscience, 2009, vol. 29, No. 43, pp. 13589-13602, doi: 110.1523/JNEUROSCI.4286-09.2009.
Tang et al., "Role of ornithine decarboxylase antizyme inhibitor in vivo", Genes to Cells, Dec. 10, 2008, vol. 14, No. 1, pp. 79-87, XP055324401.
Tomer, R. et al., "Advanced CLARITY for rapid and high-resolution imaging of intact tissues," Nat Protoc, 2014, vol. 9, pp. 1682-1697.
Valori, C.F. et al., "Systemic delivery of scAAV9 expressing SMN prolongs survival in a model of spinal muscular atrophy," Sci Transl Med, 2010, 2(35):35ra42, 9 pages, doi:10.1126/scitranslmed.3000830.
Van Der Marel, S., et al., "Neutralizing antibodies against adeno-associated viruses in inflammatory bowel disease patients: implications for gene therapy," Inflamm Bowel Dis, 2011, vol. 17, pp. 2436-2442, doi:10.1002/ibd.21673.
Vandendriessche, T. et al., "Efficacy and safety of adeno-associated viral vectors based on serotype 8 and 9 vs. lentiviral vectors for hemophilia B gene therapy," Journal of thrombosis and haemostasis : JTH, 2007, vol. 5, pp. 16-24.
Wagner et al., "Efficient and persistentgene transfer of AAV-CFTR in maxillary sinus," Lancet, 1998, vol. 351, Issue 9117, pp. 1702-1703.
Wall, N.R. et al., "Differential innervation of direct- and indirect-pathway striatal projection neurons," Neuron, 2013, vol. 79, pp. 347-360.
Wall, N.R., et al., "Monosynaptic circuit tracing in vivo through Cre-dependent targeting and complementation of modified rabies virus," Proc Natl Acad Sci USA, 2010, vol. 107, pp. 21848-21853, doi:10.1073/pnas.1011756107.
Wang, H., et al., "Widespread spinal cord transduction by intrathecal injection of rAAV delivers efficacious RNAi therapy for amyo-

(56) References Cited

OTHER PUBLICATIONS trophic lateral sclerosis," Hum Mol Genet, 2014, vol. 23, pp. 668-681, doi:10.1093/hmg/ddt454.
Wang, J. et al., "Existence of transient functional double-stranded DNA intermediates during recombinant AAV transduction," Proceedings of the National Academy of Sciences of the United States of America, 2007, vol. 104, No. 32, pp. 13104-13109, doi:10.1073/pnas.0702778104.
Wobus, C.E., et al., "Monoclonal antibodies against the adeno-associated virus type 2 (AAV-2) capsid: epitope mapping and identification of capsid domains involved in AAV-2-cell interaction and neutralization of AAV-2 infection," J Virol, 2000, vol. 74, pp. 9281-9293.
Wu et al., "Mutational analysis of the adeno-associated virus type 2 (AAV2) capsid gene and construction of AAV2 vectors with altered tropism," Journal of Virology, 2000, vol. 74, No. 18, pp. 8635-8647.
Wu, T. et al., "Self-complementary AAVs induce more potent transgene product-specific immune responses compared to a single-stranded genome," Mol Ther, 2012, vol. 20, pp. 572-579.
Wu, Z., et al., "Adeno-associated virus serotypes: vector toolkit for human gene therapy," Molecular therapy : the journal of the American Society of Gene Therapy, 2006, vol. 14, pp. 316-327, doi: 10.1016/j.ymthe.2006.05.009.
Xie, J., et al., "MicroRNA-regulated, Systemically Delivered rAAV9: A step closer to CNS-restricted transgene expression," Molecular therapy, 2010, vol. 19, pp. 526-535, doi:10.1038/mt.2010.279.
Yang, B. et al., Global CNS Transduction of Adult Mice by Intravenously Delivered rAAVrh.8 and rAAVrh.10 and Nonhuman Primates by rAAVrh.10, Molecular Therapy, 2014a, vol. 22, pp. 1299-1309.
Yang, B. et al., "Single-Cell Phenotyping within Transparent Intact Tissue through Whole-Body Clearing," Cell, 2014, vol. 158, pp. 945-958. doi:10.1016/j.cell.2014.07.017.
Yang, L. et al., "A myocardium tropic adeno-associated virus (AAV) evolved by DNA shuffling and in vivo selection," Proceedings of the National Academy of Sciences of the United States of America, 2009, vol. 106, pp. 3946-3951.
Ying, Y., et al., "Heart-targeted adeno-associated viral vectors selected by in vivo biopanning of a random viral display peptide library," Gene therapy, 2010, vol. 17, pp. 980-990, doi: 10.1038/gt.2010.44.
Zariwala et al., "A Cre-dependent GCaMP3 reporter mouse for neuronal imaging in vivo", J. Neurosci., Feb. 29, 2012, vol. 32, No. 9, pp. 3131-3141.
Zolotukhin, S. et al., "Recombinant adeno-associated virus purification using novel methods improves infectious titer and yield," Gene therapy, 1999, vol. 6, pp. 973-985, doi:10.1038/sj.gt.3300938.
Bartel et al., "Directed evolution of novel adeno-associated viruses for therapeutic gene delivery," Gene Therapy 2012, 19, 694-700.
Colman et al., Visual Biochemistry, 5th edition, Laboratory of Knowledge, Moscow, 2018, p. 58.
Extended European Search Report dated Jan. 4, 2017 for European Application No. 14843244.6.
Groth et al., "A phage integrase directs efficient site-specific integration in human cells," PNAS 2000, 97(11), 5995-6000.
Huser et al., "Kinetics and Frequency of Adeno-Associated Virus Site-Specific Integration into Human Chromosome 19 Monitored by Quantitative Real-Time PCR," J. Virol. 2002, 76(15), 7554-7559.
Koerber et al., "DNA Shuffling of Adeno-associated Virus Yields Functionally Diverse Viral Progeny," Mol Ther. 2008, 16(10), 1703-1709.
Koerber et al., "Molecular Evolution of Adeno-associated Virus for Enhanced Glial Gene Delivery," Mol. Ther 2009, 7(12), 2088-2095.

Office Action dated Sep. 6, 2017 in U.S. Appl. No. 15/422,237.
Office Action dated Dec. 24, 2019 for Chilean Patent Application No. 01522-2018 filed Jun. 7, 2018.
Varadi et al., "Novel random peptide libraries displayed on AAV serotype 9 for selection of endothelial cell-directed gene transfer vectors," Gene Therapy 2012, 19, 800-809.
Waterkamp et al., "Isolation of targeted AAV2 vectors from novel virus display libraries," J Gene Med. 2006, 8(11), 1307-1319.
Notice before Examination dated Sep. 22, 2019 for Israeli Patent Application No. 259842.
Notice of Allowance dated Aug. 15, 2019 in U.S. Appl. No. 16/222,549, filed Dec. 17, 2018.
Office Action dated Dec. 3, 2019 for Russian Application No. 2018120736 filed Jul. 11, 2018.
Singer et al., "Genes and Genomes, A changing Perspective", 1998, 1, p. 63.
Office Action dated Jan. 22, 2020 in Colombian Patent Application No. NC2018/0007203.
Chen & Rice, "New Insight Into Site-Specific Recombination From FLP Recombinase-DNA Structures," Annu. Rev. Biophys. Biomol. Struct. 2003, 32, 135-159.
Non-Final Office Action dated Jul. 10, 2020 in U.S. Appl. No. 16/379,641.
Notice of Allowance dated Apr. 27, 2020 in Russian Patent Application No. 2018120736.
Van Duyne et al., "A Structural View of Cre-*loxP* Site-Specific Recombination," Annu. Rev. Biophys. Biomol. Struct. 2001, 30, 87-1 04.
Office Action dated Jul. 17, 2020 in Colombian Patent Application No. NC2018/0007203.
Office Action dated Jul. 19, 2020 for Chilean Patent Application No. 01522-2018 filed Jun. 7, 2018.
Office Action dated Dec. 8, 2020 for Japanese Patent Application No. 2018-530606 filed Jun. 11, 2018.
Xu et al., "Adeno-related viral shell modification and tumor targeting therapy," Chinese Science Bulletin, 53(21):2546-2553 (2008).
Non-Final Office Action dated Feb. 2, 2021 in U.S. Appl. No. 16/680,402.
Notice of Allowance dated Dec. 30, 2020 in U.S. Appl. No. 16/379,641.
Hu et al., Research Progress of Adenovirus Vectors Used in Gene Therapy, Med & Pharm J Chin PLA, vol. 23, No. 5, pp. 76-80, Oct. 2011.
Notice of Allowance dated May 12, 2021 in U.S. Appl. No. 16/680,402.
Office Action dated Jul. 5, 2021 in Chinese Patent Application No. 201680081708.1.
Decision of Refusal dated Jul. 9, 2021 in Japanese Patent Application No. 2018-530606.
Extended European Search Report dated Jul. 30, 2021 for European Patent Application No. 21152352.7.
Yu et al., Cloning of ORF5 gene of PRRSV HN25 strain and construction of recombinant adenovirus, Animal Husbandry and Veterinary, vol. 42, No. 1, pp. 61-63, 2010.
Chan et al. "Engineered AAVs for efficient noninvasive gene delivery to the central and peripheral nervous systems" Nat Neurosci. 2017, 20(8): 1172-1179. doi:10.1038/nn.4593.
Decision of Refusal dated Dec. 7, 2021 in Japanese Patent Application No. 2018-530606.
Office Action dated Nov. 23, 2021 in Israeli Patent Application No. 259842.
Office Action dated Dec. 20, 2021 in Canadian Patent Application No. 3,007,495.
Office Action dated Dec. 29, 2021 in Korean Patent Application No. 10-2018-7019747.

* cited by examiner

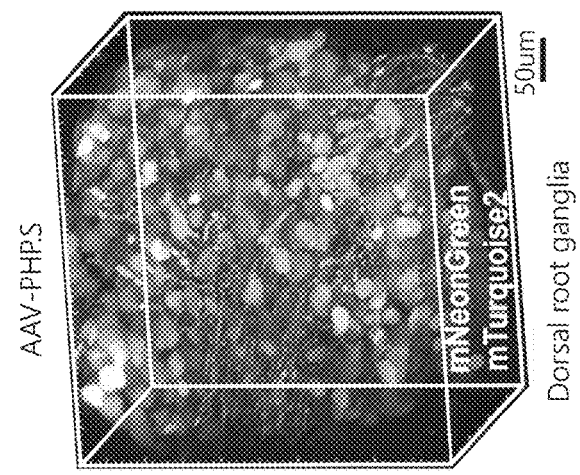
FIG. 3C
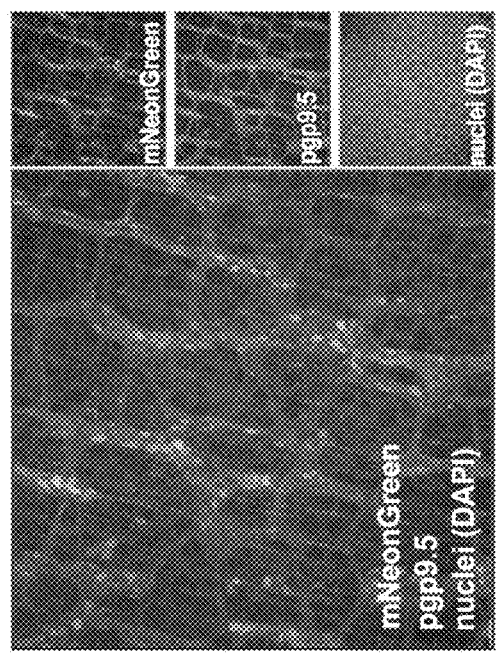
FIG. 3D
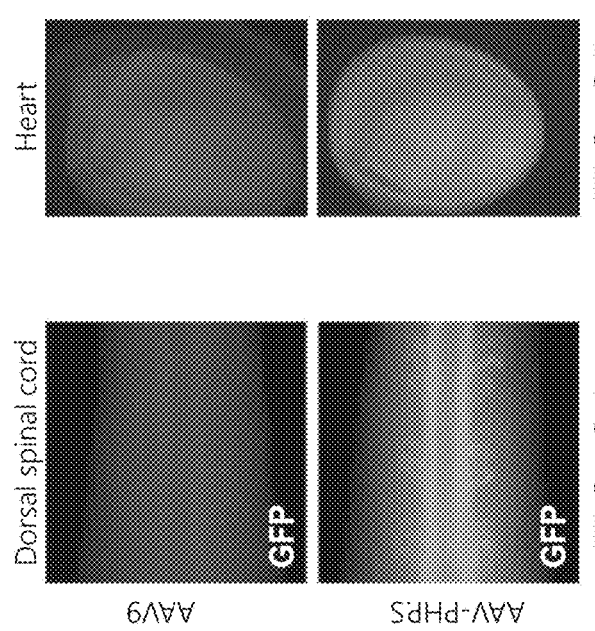
FIG. 3A
FIG. 3B

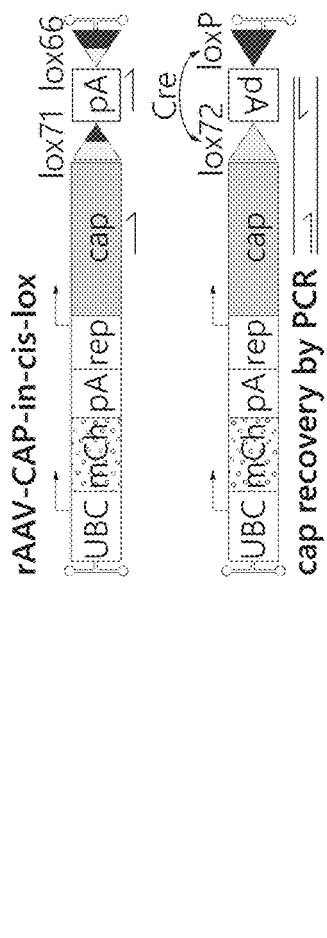
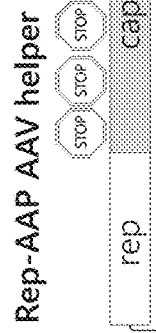
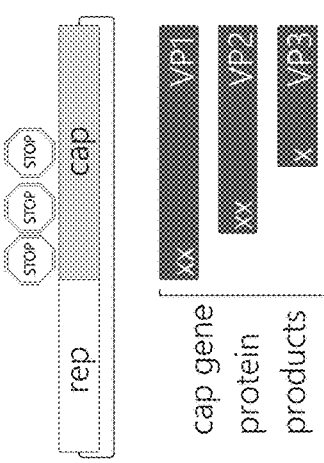
FIG. 4B
FIG. 4D
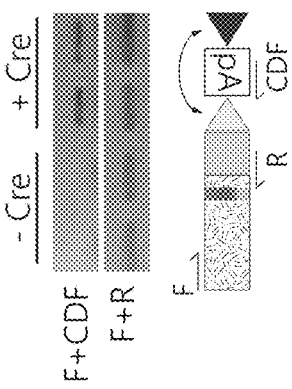
FIG. 4C
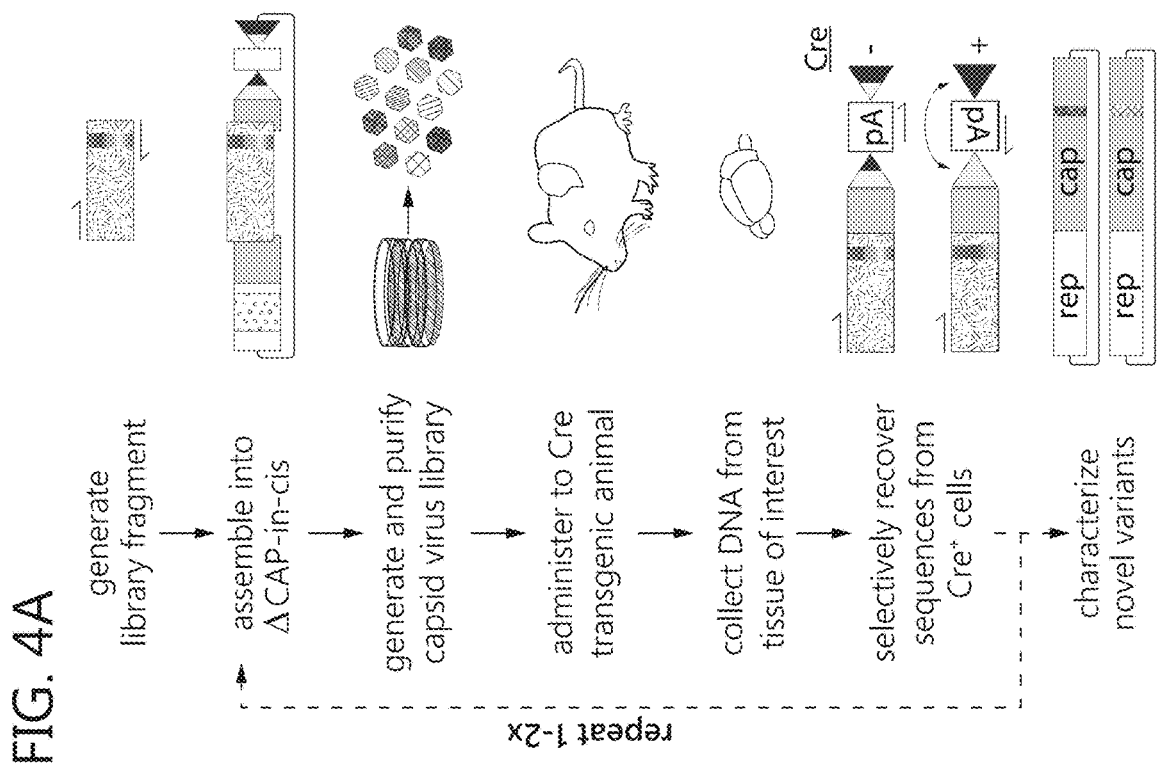
FIG. 4A

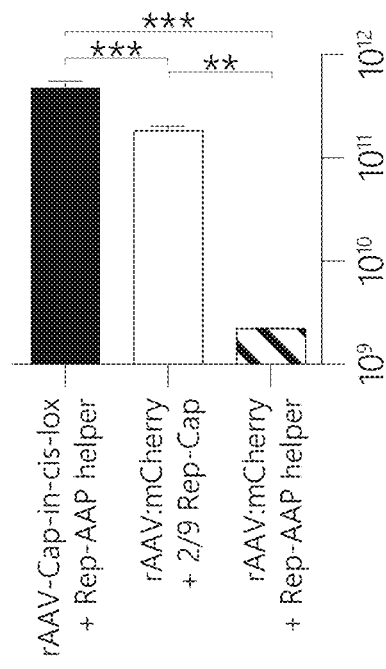
FIG. 4E
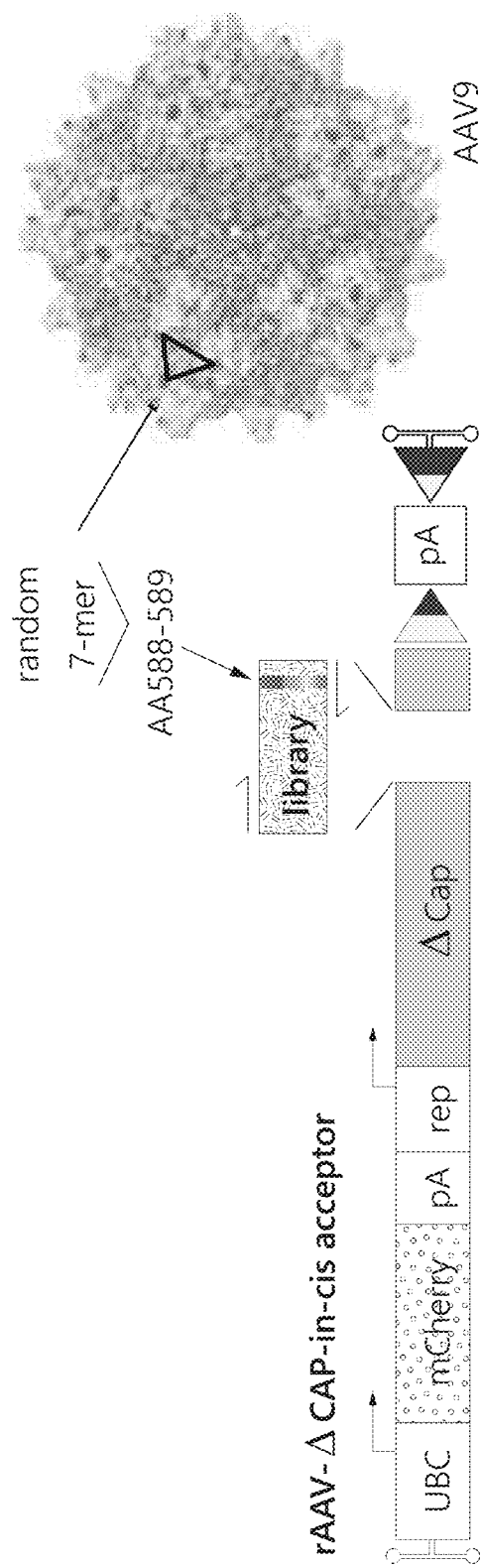
FIG. 4F
FIG. 4G

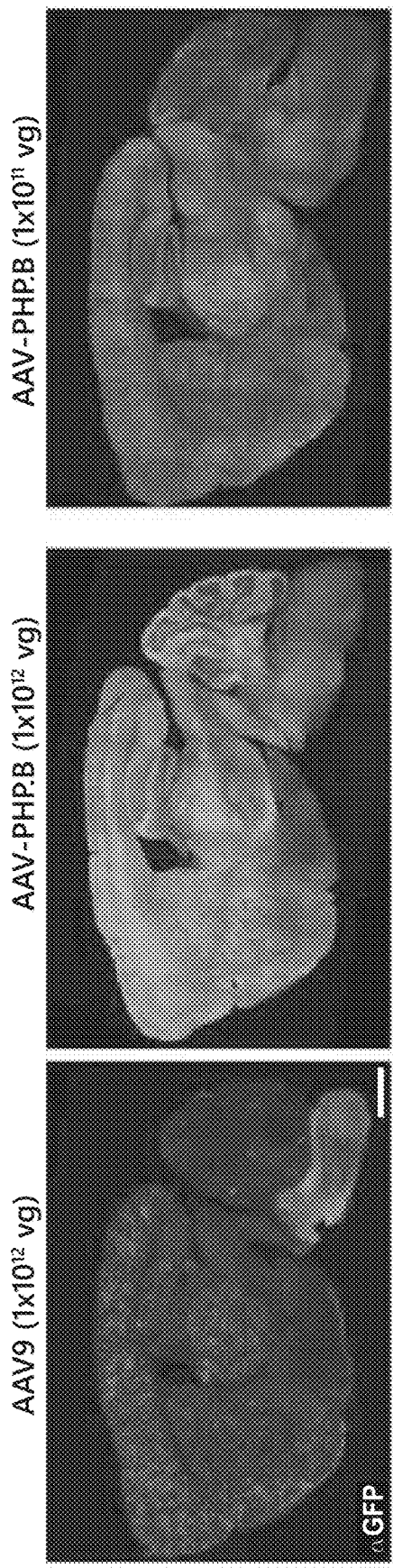
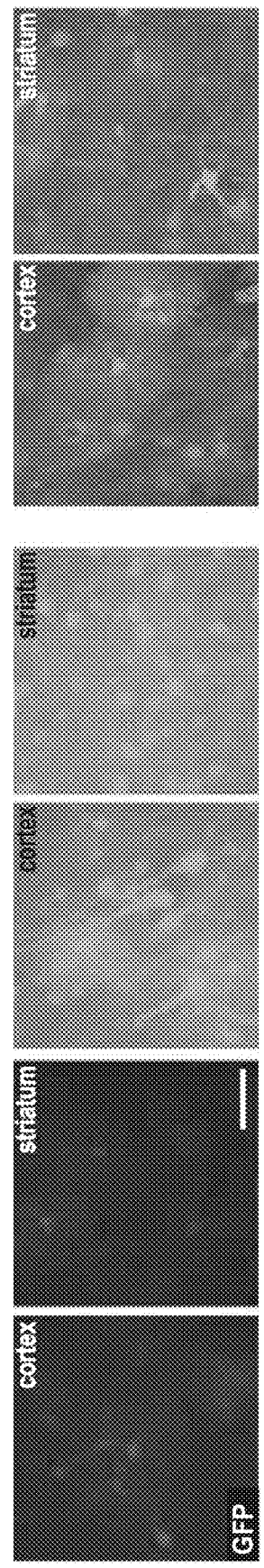
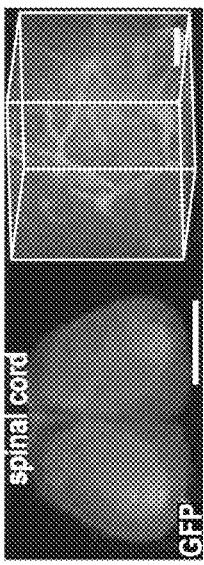
FIG. 5A
FIG. 5B
FIG. 5C
FIG. 5D

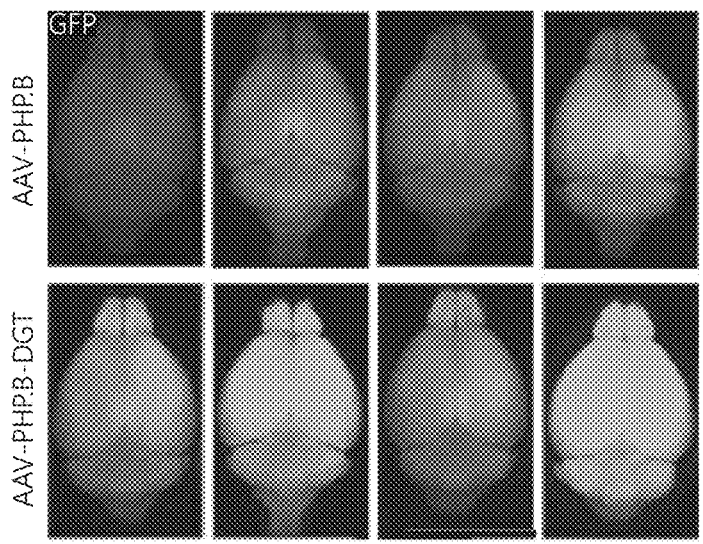
FIG. 19A
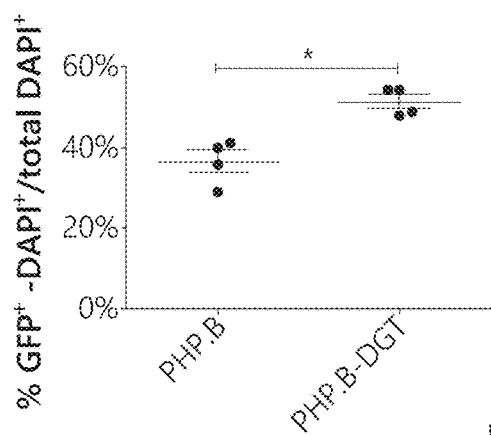 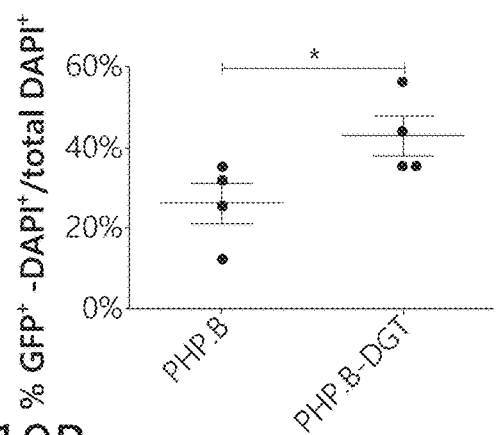
FIG. 19B
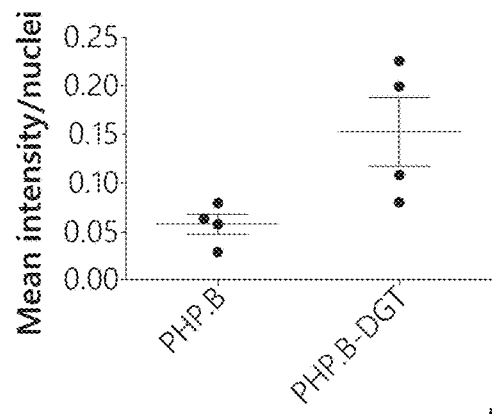 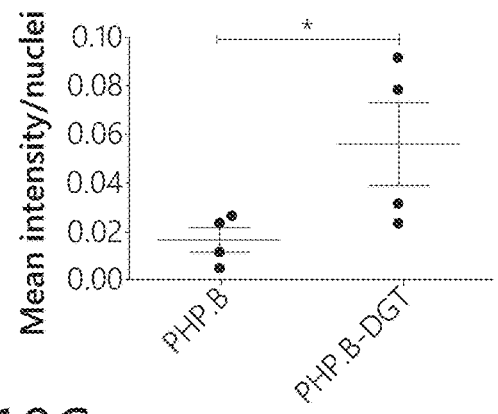
FIG. 19C

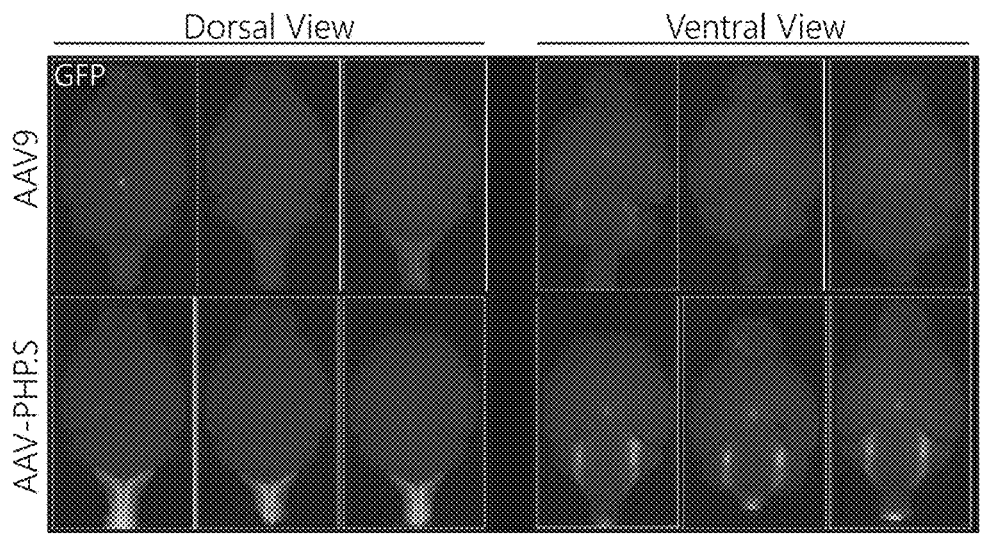
FIG. 20A GFP fluorescence – whole brain images
Spinal Cord
FIG. 20B
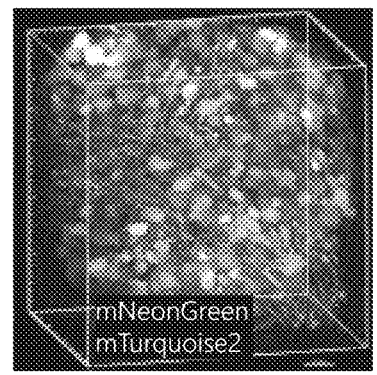
Dorsal root ganglia
FIG. 20C
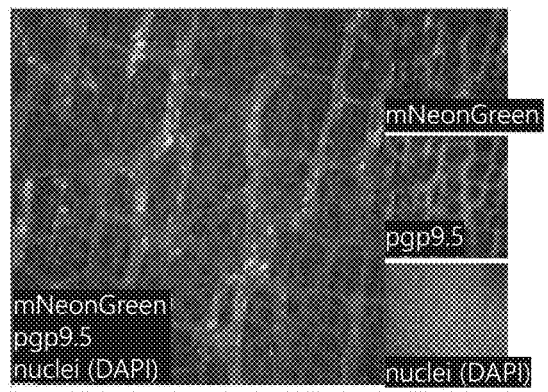
Intestine
FIG. 20D

PHP.B 7-mer – inserted between AA 588-589

PHP.B  SAQTLAVPFKAQAQ (SEQ ID NO: 48)

| | |
|---|---|
| XXX1 | SXXXLAVPFKAQAQ (SEQ ID NO: 49) |
| XXX2 | SAQXXXXVPFKAQAQ (SEQ ID NO: 50) |
| XXX3 | SAQTLXXXFKAQAQ (SEQ ID NO: 51) |
| XXX4 | SAQTLAVXXXAQAQ (SEQ ID NO: 52) |
| XXX5 | SAQTLAVPFXXXAQ (SEQ ID NO: 53) |

AAV-PHP.N VP1 Capsid Sequence
SEQ ID NO: 46

MAADGYLPDWLEDNLSEGIREWWALKPGAPQPKANQQHQDNARGLVLPGYKYLGPNGLDKGEP
VNAADAAALEHDKAYDQQLKAGDNPYLKYNHADAEFQERLKEDTSFGGNLGRAVFQAKKRLLEP
LGLVEEAAKTAPGKKRPVEQSPQEPDSSAGIGKSGAQPAKKRLNFGQTGDTESVPDPQPIGEPP
AAPSGVGSLTMASGGGAPVADNNEGADGVGSSSGNWHCDSQWLGDRVITTSTRTWALPTYNNHL
YKQISNSTSGGSSNDNAYFGYSTPWGYFDFNRFHCHFSPRDWQRLINNNWGFRPKRLNFKLFNI
QVKEVTDNNGVKTIANNLTSTVQVFTDSDYQLPYVLGSAHEGCLPPFPADVFMIPQYGYLTLND
GSQAVGRSSFYCLEYFPSQMLRTGNNFQFSYEFENVPFHSSYAHSQSLDRLMNPLIDQYLYYLS
RTINGSGQNQQTLKFSVAGPSNMAVQGRNYIPGPSYRQQRVSTTVTQNNNSEFAWPGASSWALN
GRNSLMNPGPAMASHKEGEDRFFPLSGSLIFGKQGTGRDNVDADKVMITNEEIKTTNPVATES
YGQVATNHQSSTLAVPFEKAQAQTGWVQNQGILPGMVWQDRDVYLQGPIWAKIPHTDGNFHPSP
LMGGFGMKHPPPQILIKNTPVPADPPTAFNKDKLNSFITQYSTGQVSVEIEWELQKENSKRWNP
EIQYTSNYYKSNNVEFAVNTEGVYSEPRPIGTRYLTRNL

FIG. 22B

AAV-PHP.S VP1 Capsid Sequence
SEQ ID NO: 47

MAADGYLPDWLEDNLSEGIREWWALKPGAPQPKANQQHQDNARGLVLPGYKYLGPNGLDKGEP
VNAADAAALEHDKAYDQQLKAGDNPYLKYNHADAEFQERLKEDTSFGGNLGRAVFQAKKRLLEP
LGLVEEAAKTAPGKKRPVEQSPQEPDSSAGIGKSGAQPAKKRLNFGQTGDTESVPDPQPIGEPP
AAPSGVGSLTMASGGGAPVADNNEGADGVGSSSGNWHCDSQWLGDRVITTSTRTWALPTYNNHL
YKQISNSTSGGSSNDNAYFGYSTPWGYFDFNRFHCHFSPRDWQRLINNNWGFRPKRLNFKLFNI
QVKEVTDNNGVKTIANNLTSTVQVFTDSDYQLPYVLGSAHEGCLPPFPADVFMIPQYGYLTLND
GSQAVGRSSFYCLEYFPSQMLRTGNNFQFSYEFENVPFHSSYAHSQSLDRLMNPLIDQYLYYLS
RTINGSGQNQQTLKFSVAGPSNMAVQGRNYIPGPSYRQQRVSTTVTQNNNSEFAWPGASSWALN
GRNSLMNPGPAMASHKEGEDRFFPLSGSLIFGKQGTGRDNVDADKVMITNEEIKTTNPVATES
YGQVATNHQSAQQAVRTSLAQAQTGWVQNQGILPGMVWQDRDVYLQGPIWAKIPHTDGNFHPSP
LMGGFGMKHPPPQILIKNTPVPADPPTAFNKDKLNSFITQYSTGQVSVEIEWELQKENSKRWNP
EIQYTSNYYKSNNVEFAVNTEGVYSEPRPIGTRYLTRNL

TARGETING PEPTIDES FOR DIRECTING ADENO-ASSOCIATED VIRUSES (AAVS)

RELATED APPLICATIONS

The present application claims priority under 35 U.S.C. § 119(e) to U.S. Provisional Application No. 62/266,184, filed on Dec. 11, 2015 and U.S. Provisional Application No. 62/421,891, filed on Nov. 14, 2016. The present application is also related to U.S. patent application Ser. No. 14/485,024, filed on Sep. 12, 2014. The contents of these related applications are herein expressly incorporated by reference in their entireties.

STATEMENT REGARDING FEDERALLY SPONSORED R&D

This invention was made with government support under Grant No. AG047664, Grant No. OD017782, Grant No. NS087949, Grant No. NS090577, and Grant No. MH103824 awarded by the National Institutes of Health. The government has certain rights in the invention.

REFERENCE TO SEQUENCE LISTING

The present application was filed with a Sequence Listing in electronic format and provided as a file entitled SEQLISTING.TXT which was created Dec. 9, 2016 and 40 Kb in size. The Sequence Listing is updated by an Electronic Substitute Sequence Listing file entitled "SubSeqListing", created on Jan. 3, 2021, which is 40 Kb in size. The information in the electronic format of the Sequence Listing and the Substitute Sequence Listing is incorporated herein by reference in its entirety.

BACKGROUND

Field

The present application relates generally to the field of gene delivery. More particularly, the application relates to peptide sequences capable of directing adeno-associated viruses (AAV) to target tissues or organs, novel recombinant AAVs, and methods of using the AAVs to treat various diseases.

Description of the Related Art

Recombinant adeno-associated viruses (rAAV) are vectors used for in vivo gene transfer to carry out gene therapies and facilitate the gene transfer critical for a wide variety of basic science studies. Several characteristics make rAAVs attractive as gene delivery vehicles: (i) they provide long-term transgene expression, (ii) they are not associated with any known human disease, (iii) they elicit relatively weak immune responses, (iv) they are capable of transducing a variety of dividing and non-dividing cell types and (v) the rAAV genome can be packaged into a variety of capsids, or protein coat of the virus, which have different transduction characteristics and tissue tropisms. Gene therapies that use rAAV vectors have been successful in clinical trials including treatment for Leber's congenital amaurosis, hemophilia associated with factor IX deficiency and lipoprotein lipase deficiency. In addition, rAAV-gene based therapy has been successful in pre-clinical models in a variety of diseases including Rett syndrome, congenital ALS, Parkinson's, Huntington's disease and Spinal Muscular Atrophy. rAAV based therapy has also shown success in delivering neutralizing antibodies to treat infectious diseases such as HIV and influenza. rAAVs are also popular vectors for in vivo delivery of transgenes for non-therapeutic scientific studies, such as optogenics. However, the successful use of rAAVs for the treatment of disease and for the delivery of genes for scientific studies for many applications has been constrained by the lack of capsid serotypes that can efficiently transduce certain difficult cell types, and the lack of serotypes that can efficiently and selectively target a desired cell type/organ after systemic delivery.

SUMMARY

Disclosed herein are an AAV vector comprising an amino acid sequence that comprises at least 4 contiguous amino acids of the sequence QAVRTSL (SEQ ID NO: 37). The amino acid sequence can be, for example, a part of a capsid protein of the AAV vector. In some embodiments, the sequence QAVRTSL (SEQ ID NO: 37) is inserted between AA588-589 of an AAV sequence of the vector (SEQ ID NO: 45). In some embodiments, the sequence QAVRTSL (SEQ ID NO: 37) is inserted between AA586-592 of an AAV sequence of the vector (SEQ ID NO: 45). In some embodiments, the amino acid sequence further comprises at least two of amino acids 587, 588, 589, or 590 of SEQ ID NO: 45.

Also disclosed is an AAV vector comprising a sequence of 11 contiguous amino acids $X_1X_2X_3X_4X_5X_6X_7X_8X_9X_{10}X_{11}$, wherein $X_1$ is D, A, E, Q, N, G, or S;
$X_2$ is G, N, S, T, Q, or V;
$X_3$ is T, S or N;
$X_4$ is L or V;
$X_5$ is A, S, Q, P, or T;
$X_6$ is V, T, Q, N, L, or M;
$X_7$ is P;
$X_8$ is F, Y, V, L, C, or S;
$X_9$ is K, R or S;
$X_{10}$ is A or N; and
$X_{11}$ is Q or P, wherein the AAV vector does not comprise amino acid sequence AQTLAVPFKAQ (SEQ ID NO: 1). In some embodiments, the sequence of 11 contiguous amino acids is part of, or comprises, a targeting peptide. In some embodiments, $X_1$ is D, $X_2$ is G, $X_3$ is T, $X_4$ is L, $X_6$ is V or T, $X_8$ is F, any combination thereof. In some embodiments, $X_1$ is D, $X_2$ is G, $X_3$ is T, $X_4$ is L, $X_6$ is V or T, or $X_8$ is F. In some embodiments, $X_1$ is D, $X_2$ is G, $X_3$ is T, $X_4$ is L, $X_6$ is V or T, and $X_8$ is F. In some embodiments, $X_4$ is L, $X_5$ is A, $X_6$ is V, $X_7$ is P, $X_8$ is F, $X_9$ is K, $X_{10}$ is A, and $X_{11}$ is Q. In some embodiments, amino acids $X_1X_2X_3$ are DGT, GGT, EGT, DST, EST, QGT, NQT, SGS, SGN, ATT, AVT, or ART. In some embodiments, amino acids $X_1X_2$ are AQ, $X_6$ is V, $X_7$ is P, $X_8$ is F, $X_9$ is K, $X_{10}$ is A, and $X_{11}$ is Q. In some embodiments, $X_3$ is T and $X_4$ is L. In some embodiments, $X_5$ is A. In some embodiments, $X_1$ is A, $X_2$ is Q, $X_3$ is T, $X_4$ is L, $X_8$ is F, $X_9$ is K, $X_{10}$ is A, and $X_{11}$ is Q. In some embodiments, amino acids $X_5X_6X_7$ are AVP, ATP, AQP, QQP, PQP, SNP, STP, SQP, QLP, TMP, or TTP. In some embodiments, amino acids $X_1X_2X_3X_4X_5X_6$ are AQTLAV and $X_{10}X_{11}$ is AQ. In some embodiments, amino acids $X_7X_8X_9$ are PFK. In some embodiments, amino acids $X_1X_2X_3X_4X_5X_6X_7X_8$ are AQTLAVPF. In some embodiments, amino acids $X_9X_{10}X_{11}$ are KAQ, KAP, or SNP. In some embodiments, the sequence of 11 continuous amino acid is part of a capsid protein of the AAV vector. In some embodiments, the sequence of 11 contiguous amino acids is inserted between AA586-589 of an AAV capsid protein sequence, for example SEQ ID NO: 45, of the vector. In some embodiments, the sequence of 11 continuous amino acids is one of SEQ ID NOs: 1-36.

Disclosed herein is a pharmaceutical composition, comprising one or more of the AAV vectors disclosed herein and one or more pharmaceutical acceptable carriers.

Also disclosed herein is a peptide, wherein the peptide comprises an amino acid sequence set forth in one of SEQ ID NOs: 1-44, 48-53, 65-68, and 80-93. In some embodiments, the peptide is conjugated to a nanoparticle, a second molecule, a viral capsid protein, or a combination thereof. In some embodiments, the peptide is part of an AAV. For example, the peptide can be a capsid protein of the AAV.

Some embodiments disclosed herein provide nucleic acid sequenc encoding all of the peptides, including the targeting peptides and fragments thereof.

Also disclosed herein is a capsid protein comprising one more targeting peptides disclosed herein. For example, the capsid protein can comprise an amino acid sequence that comprises at least 4 contiguous amino acids of the sequence QAVRTSL (SEQ ID NO: 37). Ins ome embodiments, the capsid protein comprises a sequence of 11 contiguous amino acids $X_1X_2X_3X_4X_5X_6X_7X_8X_9X_{10}X_{11}$, wherein $X_1$ is D, A, E, Q, N, G, or S;
$X_2$ is G, N, S, T, Q, or V;
$X_3$ is T, S or N;
$X_4$ is L or V;
$X_5$ is A, S, Q, P, or T;
$X_6$ is V, T, Q, N, L, or M;
$X_7$ is P;
$X_8$ is F, Y, V, L, C, or S;
$X_9$ is K, R or S;
$X_{10}$ is A or N; and
$X_{11}$ is Q or P, wherein the capsid protein does not comprise amino acid sequence AQTLAVPFKAQ (SEQ ID NO: 1). In some embodiments, $X_1$ is D, $X_2$ is G, $X_3$ is T, $X_4$ is L, $X_6$ is V or T, or $X_8$ is F. In some embodiments, $X_4$ is L, $X_5$ is A, $X_6$ is V, $X_7$ is P, $X_8$ is F, $X_9$ is K, $X_{10}$ is A, and $X_{11}$ is Q. In some embodiments, amino acids $X_1X_2X_3$ are DGT, GGT, EGT, DST, EST, QGT, NQT, SGS, SGN, ATT, AVT, or ART. In some embodiments, amino acids $X_1X_2$ are AQ, $X_6$ is V, $X_7$ is P, $X_8$ is F, $X_9$ is K, $X_{10}$ is A, and $X_{11}$ is Q. In some embodiments, $X_3$ is T and $X_4$ is L. In some embodiments, $X_5$ is A. In some embodiments, $X_1$ is A, $X_2$ is Q, $X_3$ is T, $X_4$ is L, $X_8$ is F, $X_9$ is K, $X_{10}$ is A, and $X_{11}$ is Q. In some embodiments, amino acids $X_5X_6X_7$ are AVP, ATP, AQP, QQP, PQP, SNP, STP, SQP, QLP, TMP, or TTP. In some embodiments, amino acids $X_1X_2X_3X_4X_5X_6$ are AQTLAV and $X_{10}X_{11}$ is AQ. In some embodiments, $X_7X_8X_9$ is PFK. In some embodiments, amino acids $X_1X_2X_3X_4X_5X_6X_7X_8$ are AQTLAVPF. In some embodiments, amino acids $X_9X_{10}X_{11}$ are KAQ, KAP, or SNP. Also provided are nucleic acid sequences encoding the capsid proteins disclosed herein and the fragments thereof.

A method of delivering a nucleic acid to a target environment of a subject in need is also disclosed. The method, in some embodiments, comprises: providing a composition comprising an AAV, wherein the AAV comprises a capsid protein that comprises a sequence of 11 contiguous amino acids $X_1X_2X_3X_4X_5X_6X_7X_8X_9X_{10}X_{11}$, and wherein the AAV comprises a nucleic acid to be delivered to the target environment of of the subject, wherein $X_1$ is D, A, E, Q, N, G, or S;
$X_2$ is G, N, S, T, Q, or V;
$X_3$ is T, S or N;
$X_4$ is L or V;
$X_5$ is A, S, Q, P, or T;
$X_6$ is V, T, Q, N, L, or M;
$X_7$ is P;
$X_8$ is F, Y, V, L, C, or S;
$X_9$ is K, R or S;
$X_{10}$ is A or N; and
$X_{11}$ is Q or P, wherein the capside protein does not comprise amino acid sequence AQTLAVPFKAQ (SEQ ID NO: 1); and administering the composition to the subject. The method, in some embodiments, comprises: providing a composition comprising an AAV, wherein the AAV comprises a capsid protein that comprises an amino acid sequence that comprises at least 4 contiguous amino acids of the sequence QAVRTSL (SEQ ID NO: 37), and wherein the AAV comprises a nucleic acid to be delivered to the target environment of the subject; and administering the composition to the subject. The target environment can be, for example, the heart, the nervous system, or a combination thereof. In some embodiments, the target environment is the central nervous system, the peripheral nervous system, the heart, or a combination thereof. In some embodiments, the target environment is neurons, astrocytes, cardiomyocytes, or a combination thereof. In some embodiments, the composition is a pharmaceutical composition. In some embodiments, the nucleic acid to be delivered to the nervous system comprises one or more of: a) a nucleic acid sequence encoding a trophic factor, a growth factor, or a soluble protein; b) a cDNA that restores protein function to humans or animals harboring a genetic mutation(s) in that gene; c) a cDNA that encodes a protein that can be used to control or alter the activity or state of a cell; d) a cDNA that encodes a protein or a nucleic acid used for assessing the state of a cell; e) a cDNA and/or associated guide RNA for performing genomic engineering; f) a sequence for genome editing via homologous recombination; g) a DNA sequence encoding a therapeutic RNA; h) a shRNA or an artificial miRNA delivery system; and i) a DNA sequence that influences the splicing of an endogenous gene. The subject in need can be, for example, a subject suffering from or at a risk to develop one or more of chronic pain, cardiac failure, cardiac arrhythmias, Friedreich's ataxia, Huntington's disease (HD), Alzheimer's disease (AD), Parkinson's disease (PD), Amyotrophic lateral sclerosis (ALS), spinal muscular atrophy types I and II (SMA I and II), Friedreich's Ataxia (FA), Spinocerebellar ataxia, lysosomal storage disorders that involve cells within the CNS. The lysosomal storage disorder can be, for example, Krabbe disease, Sandhoff disease, Tay-Sachs, Gaucher disease (Type I, II or III), Niemann-Pick disease (NPC1 or NPC2 deficiency), Hurler syndrome, Pompe Disease, or Batten disease. In some embodiments, the AAV is administered to the subject via intravenous administration or systemic administration. The nervous system can be, for example, the central nervous system. In some embodiments, the nucleic acid is delivered to dorsal root ganglia, visceral organs, or a combination thereof of the subject. In some embodiments, the nucleic acid is delivered astrocytes, neurons, or a combination thereof of the subject. In some embodiments, the subject is an adult animal.

BRIEF DESCRIPTION OF THE DRAWINGS

FIGS. 3A-3D depict the enhanced transduction of AAV-PHP.S in the mouse heart and peripheral nerves as compared with AAV9. FIG. 3A depicts sensory fibers entering the dorsal spinal cord of mice 3 weeks after intravenous injection of $2 \times 10^{12}$ vg/mouse of ssAAV9:CAG-NLS-GFP or ssAAV-PHP.S:CAG-NLS-GFP (NLS, nuclear localization signal) into adult mice. AAV-PHP.S provides stronger GFP expression in the sensory fibers than AAV9 as shown by brighter staining of the AAV-PHP.S treated sample relative to the AAV9 treated sample. FIG. 3B shows images of native fluorescence from GFP protein expression, shown by bright signals, from the heart 3 weeks after intravenous administration of $1 \times 10^{12}$ vector genomes (vg)/mouse of recombinant single stranded (ss)AAV9:CAG-GFP-2A-Luc or ssAAV-PHP.S:CAG-GFP-2A-Luc. FIG. 3C depicts a 3D projection image showing native fluorescence in a dorsal root ganglion of a mouse 4 weeks after injection of a mixture of $1 \times 10^{12}$ vg of ssAAV-PHP.S:CAG-mNeonGreen and $1 \times 10^{12}$ vg of ssAAV-PHP.S:CAG-mTurquoise. Both channels are shown together in the grayscale image. FIG. 3D depicts AAV-PHP.S transducing cells within the enteric nervous system after intravenous injection. Bright spots mark cells transduced by AAV-PHP.S. Images show a maximum intensity projection from the adult mouse intestine assessed 3 weeks after intravenous administration of $1 \times 10^{12}$ vg/mouse of ssAAV-PHP.S:CAG-mNeonGreen. Bright spots show mNeon-Green expression from the AAV-PHP.S vector (see, left panel and upper right panel). Neurons with the myenteric plexus are labeled with an antibody against pgp9.5 and nuclei labeled by DAPI are shown in lower, right panel.

FIGS. 4A-4G depict Cre-dependent recovery of AAV capsid sequences from transduced target cells. FIG. 4A depicts an overview of the CREATE selection process. PCR is used to introduce diversity (full visual spectrum vertical band) into a capsid gene fragment. The fragment is cloned into the rAAV genome harboring the remaining capsid gene and is used to generate a library of virus variants. The library is injected into Cre transgenic animals and PCR is used to selectively recover capsid sequences from Cre+ cells. FIG. 4B depicts the rAAV-Cap-in-cis-lox rAAV genome. Cre inverts the polyadenylation (pA) sequence flanked by the lox71 and lox66 sites. PCR primers (half arrows) are used to selectively amplify Cre-recombined sequences. FIG. 4C depicts PCR products from Cre recombination-dependent (top) and -independent (bottom) amplification of capsid library sequences recovered from two Cre+ or Cre- mice. Schematics (bottom) show the PCR amplification strategies (see FIGS. 8A-8B for details). FIG. 4D is a schematic illustration of the AAV genes within the Rep-AAP AAV helper plasmid and the proteins encoded by the cap gene. Stop codons inserted in the cap gene eliminate VP1, VP2 and VP3 capsid protein expression. FIG. 4E depicts DNase-resistant AAV vector genomes (vg) produced with the split AAV2/9 rep-AAP and rAAV-Cap-in-cis-lox genome (top) as compared to the vg produced with standard AAV2/9 rep-cap helper and rAAV-UBC-mCherry genome (middle) or with the AAV2/9 rep-AAP and rAAV-UBCmCherry genome (bottom). N=3 independent trials per group; mean±s.d.; p<0.01, *p<0.001; oneway ANOVA and Tukey multiple comparison test. FIG. 4F depicts cloning the 7-mer capsid library into the rAAV-ΔCap-in-cis vector. FIG. 4G depicts the AAV9 surface model. FIGS. 4F-4G show the location of the 7-mer inserted between AA588-589.

FIGS. 5A-5G depict AAV-PHP.B mediated gene delivery through the CNS after intravenous injection in adult mice. In FIGS. 5A-5F, ssAAV9:CAG-GFP or ssAAV-PHP.B:CAG-GFP at the dose of $1 \times 10^{12}$ vg/mouse or $1 \times 10^{11}$ vg/mouse was intravenously injected into adult mice. FIG. 5A, show images of GFP expression (indicative of expression from ssAAV genomes delivered by the indicated capsid) in mice given AAV9 (left) and mice given AAV-PHP.B (middle and right), respectively, three weeks after injection. GFP expression is shown by bright signals. FIG. 5B shows expression of GFP (indicated by bright signals) in the cortex or striatum in 50 µm maximum intensity projection (MIP) confocal images. FIG. 5C shows expression of the GFP protein (indicated by bright signals) in the PARS-cleared lumbar spinal cord. FIG. 5D shows expression of the GFP protein (indicated by bright signals) in the retina (left: 20 µm MIP, transverse section; right: whole-mount MIP). FIGS. 5E-5F show expression of the GFP proteins (indicated by bright signals) in 3D MIP images of PARS-cleared tissue from AAV-PHP.B transduced cortex and striatum and indicated organs from mice transduced with AAV9 (top) and AAV-PHP.B (bottom). In FIG. 5F, the arrows highlight nerves that express the capsid proteins. Asterisks in the image of the pancreas highlight islet cells expressing GFP. Major tick marks in 3D projections are 100 µm. FIG. 5G depicts AAV biodistribution in the indicated CNS regions and organs 25 days after intravenous injection $1 \times 10^{11}$ vg into adult mice. N=3 for AAV-PHP.B and n-4 for AAV9; mean+/−s.d; p<0.01, *p<0.001, unpaired t tests corrected for multiple comparisons by the Holm-Sidak method. Scale bars: 1 mm (FIGS. 5A and 5C (left)); 50 µm (FIGS. 5B, 5C (right), 5D, and 5E). Major tick marks in 3D projections in FIGS. 5C, 5E and 5F are 100 µm.

FIGS. 6A-6E are images showing that AAV-PHP.B transduces astrocytes, oligodendrocytes and neurons: expression of GFP proteins 3 weeks after intravenous injection of $1 \times 10^{11}$ (FIG. 6A) or $1 \times 10^{12}$ (FIGS. 6B-6E) of ssAAV-PHP.B:CAG-GFP into adult mice. FIG. 6A shows a MIP image of staining in the hippocampus. Bright signals indicate expression of the AAV-PHP.B construct and dark signals indicate GFAP expression. FIG. 6B shows immunohistochemistry to detect expression of AAV-PHP.B and the CC1 marker in the cortex. Numbered boxes highlight examples of double positive cells. Corresponding single-channel images are shown (right). Asterisks highlight cells without detectable GFP expression. FIG. 6C shows immunohistochemistry to detect transduction of AAV-PHP.B and the NeuN marker in the indicated brain region. FIG. 6D shows MIP images of GFP fluorescence showing transduction of AAV-PHP.B and TH IHC in the midbrain. FIG. 6D depicts AAV-PHP.B transduction and Calbindin (Calb) IHC in the cerebellum. FIG. 6F-6H depict quantification of the percentage of cells positive for AAV-PHP.B transduction in the indicated brain region 3 weeks post injection. FIG. 6I shows AAV-PHP.B transducing ChAT spinal motor neurons. Bright spots show AAV-PHP.B expression. Darker signals show IHC for ChAT. Images depict whole transverse spinal cord sections (left) or ventral horn MIP image (right). The percentage of ChAT in whole transverse spinal cord sections (left) or ventral horn MIP image (right). The percentage of ChAT neurons that expressed AAV-PHP.B in each spinal cord region is given +/− the 95% confidence interval. For quantification, n=5 per group; mean+/−s.d.; All pairs of AAV9 vs AAV-PHP.B means were found to be different (***p<0.001) unpaired t tests corrected for multiple comparison by the Holm-Sidak method. Scale bars: 20 μm (FIGS. 6A-6B and FIG. 6D), 50 μm (FIGS. 6C and 6I (right)), 200 μm (FIG. 6E) and 1 mm (FIG. 6I (left)).

FIGS. 7A-7C and 7E shows expression of AAV-PHP.A 3 weeks after intravenous injection of $3\times10^{11}$ of ssAAV9:CAG-GFP or ssAAV-PHP.A:CAG-GFP into adult mice. FIGS. 7A-7B depict representative images of IHC for ssAAV9:CAG-GFP and AAV-PHP.A:CAG-GFP. FIG. 7C shows IHC for the GFP proteins in the hippocampus. Dark signals show IHC for GFAP in the hippocampus. Numbered boxes highlight examples of cells expressing both the GFP proteins and GFAP. Corresponding single-channel images are shown on the right. In FIG. 7D, $2.5\times10^{11}$ vg of ssAAV-PHP.A:CAG-NLS-GFP was injected intravenously into adult mice. Graphs show quantitation of the percentage of Aldh1l1 and NeuN cells positive for NLS-GFP. FIG. 7E shows AAV-PHP.A expression (bright signals) in the liver (tissue autofluorescence are shown with dark signals). FIG. 7F depicts AAV biodistribution in the CNS region and peripheral organs 25 days after intravenous injection of $1\times10^{11}$ vg into adult mice. In FIGS. 7E-7F, N=4 per group; mean+/−s.d: p<0.05, p<0.01, ***p<0.001, unpaired t tests corrected for multiple comparisons by the Holm=Sidak method. Scale bars: 1 mm (FIG. 7A); 100 μm (FIG. 7B); and 50 μm (FIG. 7C).

FIG. 8A is a schematic illustration of PCR products with 7 amino acids (referred to as "7AA" herein) of randomized sequence (represented by the full spectrum vertical bar) inserted after amino acid 588. The primers used to generate the library are indicated by name and half arrows. The PCR template was modified to eliminate a naturally occurring EarI restriction site within the capsid gene fragment (xE) (See Examples for details). FIG. 8B is a schematic illustration showing the rAAV-Cap-in-cis genome and the primers used to quantify vector genomes and recover sequences that have transduced Cre expressing cells. The PCR-based recovery is performed in two steps. Step 1 provides target cell-specific sequence recovery by selectively amplifying Cap sequences from genomes that have undergone Cre-dependent inversion of the downstream polyadenylation (pA) sequence. For step 1, 9CapF functions as a forward primer and the CDF primer functions as the reverse primer on templates recombined by Cre. Step 2 uses primers XF and AR to generate the PCR product that is cloned into rAAV-ΔCap-in-cis plasmid (library regeneration) or to clone into an AAV2/9 rep-cap trans plasmid (variant characterization). Table 1 provides non-limiting examples of the primer sequences that can be used in the PCR illustrated in FIGS. 8A-8B.

FIG. 9A is an image of representative sagittal brain sections from mice assessed 2 weeks after injection $3.3\times10^{10}$ vg/mouse of ssAAV-CAG-mNeonGreen-farnesylated (mNeGreen-f) packaged into AAV-PHP.B or the second or third most enriched variants, AAV-PHP.B2 and AAV-PHP.B3. Bright signals show expression of the GFP proteins. Data are representative of 2 (AAV-PHP.B) and 3 (AAV-PHP.B2 and AAV-PHP.B3) mice per group. FIG. 9B shows the amount of DNase-resistant vg obtained from preparations of the individual variants recovered from GFAP-Cre selections. Yields are given as the number of purified vector genome copies per 150 mm dish of producer cells; mean+/−s.d. *p<0.05, one-way ANOVA and Tukey multiple comparison test. The number of independent preparations for each capsid is shown within the bar.

In FIGS. 10A-10D, adult mice were injected with $1\times10^{12}$ vg of AAV-PHP.B: CAG-GFP and assessed for expression of the GFP protein 3 weeks later. Representative images show IHC for AAV-PHP.B expression (FIGS. 10A-10C) or native fluorescence from GFP protein expression (FIG. 10D) together with IHC for the indicated antigen and brain region. In FIG. 10E, adult mice were injected with $3.3\times10^{10}$ vg of ssAAV-PHP.B: CAG-mNeGrn-f assessed at 2 weeks post injection. Native fluorescence from mNeGrn-f co-localizes with some endothelial cells expression CD31. In FIGS. 10F-10G, adult mice were injected with $2\times10^{12}$ vg of ssAAV-PHP.B:CAG-NLS-GFP and assessed at 3 weeks post injection. Bright signals show expression of AAV-PHP.B, and dark signal shows expression of Ibal. Asterisks indicate cells that express the indicated antigen, but have no detectable expression of AAV-PHP.B. Parvalbumin (PV), Calbindin (Calb) and Calretinin (CR). Scale bars: 20 μm (FIGS. 10A-10D); 50 μm (FIGS. 10E-10F) and 500 μm (FIG. 10G).

In FIGS. 12A-12D, adult mice were injected with $2\times10^{12}$ vg of ssAAV-PHP.B:CAG-NLS-GFP and assessed at 3 weeks post injection. Images show native fluorescence from GFP protein expression along with IHC for the indicated antigen in the indicated brain region. In all panels, arrows indicate colocalization of GFP expression with IHC for the indicated antigen. FIGS. 12B-12C are single-plane confocal images; FIGS. 12A and 12D are MIP. Corpus Callosum (cc), substantia nigra pars compacta (SNc), ventral tagmental area (VTA). Scale bars: 50 μm.

FIG. 13A shows that AAV-PHP.B provides higher transduction of human neurons and astrocytes in associated monolayer cultures. Representative images show expression from the GFP cDNA delivered using the AAV9, AAV-PHP.A, and AAV-PHP.B capsids at five days after viral transduction (ssAAV-CAG-NLS-GFP packaged in AAV9, AAV-PHP.A, or AAV-PHP.B; $1 \times 10^9$ vg/well) of dissociated iPSC-derived human cortical spheroids differentiated in vitro. Cells expressing the GFP proteins colocalize with astrocytes immunostained for GFAP or neurons immunostained for MAP2 as indicated by white arrows. FIG. 13B shows quantification of the percentage of GFAP+ or MAP2+ cells infected by AAV9, AAV-PHP.A or AAV-PHP.B (n=3 differentiations into cortical spheroids of two human iPSC lines derived from two subjects; two-way ANOVA, Tukey multiple comparison test; mean+/−s.d.). FIG. 13C shows that AAV9, AAV-PHP.A and AAV-PHP.B transduce intact human 3D cortical cultures (cortical spheroids differentiated from human iPSCs). Images of human iPSC-derived cortical spheroid cryosections (day 205 of in vitro differentiation) transduced with ssAAV-CAG-NLS-GFP packaged in AAV9, AAV-PHP.A or AAV-PHP.B show native fluorescence from GFP protein expression together with immunostaining of GFAP and MAP2. Insets show co-lableing of the GFP protein with GFAP+ astrocytes (cyan) or MAP2+ neurons. Scale bars: 40 μm (FIG. 13A); and 100 μm (FIG. 13C).

FIGS. 14A-14B are representative images of capsid immunostaining (bright staining) using the B1 anti-AAV VP3 antibody that recognizes a shared internal epitope in the cerebellum (FIG. 14A) or striatum (FIG. 14B) in the brains of mice injected intravenously one hour prior to fixation by cardiac perfusion. Capsid immunostaining was detectable throughout the brains of mice injected with AAV-PHP.A and AAV-PHP.B, but was rarely seen in the brains of mice that received the same dose of AAV9. Cell nuclei were labeled with DAPI (dark staining). Lipofuscin autofluorescence can be distinguished from capsid staining by its presence in both green and red channels. The inset of FIG. 14A shows a 3D MIP image of the area highlighted in the AAV-PHP.B image. Arrows highlight capsid IHC signal; asterisks indicate vascular lumens. Data are representative of 2 (no virus and AAV-PHP.A) or 3 (AAV9 and AAV-PHP.B) mice per group. FIG. 14C is a representative image of GFP expression (bright staining) with DAPI (white staining) and CD31 (dark staining) 24 hours post-administration of AAV-PHP.B Arrows highlight GFP-expressing cells. FIG. 14D shows quantification of the number of GFP expression cells present along the vasculature in the indicated brain regions. N=3 per group; mean+/−s.d.: AAV-PHP.B vs AAV9 and AAV-PHP.A, ***p<0.001 for all regions; AAV9 vs AAV-PHP.A, not significant; two-way ANOVA, Scale bars: 200 μm (FIG. 14A); 50 μm (FIGS. 14B-14C); Major tick marks are 50 μm in the high magnification inset (FIG. 14A).

FIG. 15A show images of representative sagittal brain sections from mice assessed 2 weeks after injection of $3.3 \times 10^{10}$ vg/mouse of ssAAV-CAG-mNeon-Green-farneyslated (mNeGrn-f) packaged into AAV-PHP.B or the second or third most enriched variants, AAV-PHP.B2 and AAV-PHP.B3. Bright signals indicate mNeGrn-f expression from cDNA delivered by the three enriched variants, AAV-PHP.B (left), AAV-PHP.B2 (middle), and AAV-PHP.B3 (right). FIG. 15B show high magnification (40×) grayscale images of NLS-GFP expression within brain sections assessed 3 weeks after injection of $2 \times 10^{12}$ vg/mouse of ssAAV-CAG-NLS-GFP packaged into AAV-PHP.B, AAV-PHP.B2 or AAV-B3.

FIGS. 19A-19C show that CNS transduction by AAV-PHP.B-DGT is more efficient than by AAV-PHP.B after adult IV administration. FIG. 19A shows whole-brain images (dorsal view) of ssAAV-CAG-NLS-GFP expression 3 weeks after IV administration of $1 \times 10^{11}$ vg/mouse of ssAAV-CAG-NLS-GFP packaged into the indicated capsid. Expression of ssAAV-CAG-NLS-GFP is indicated by bright grayscale signal. FIG. 19B depicts graphs showing the percentage of total nuclei (DAN+) in the motor cortex (left) or striatum (right) that express GFP. FIG. 19C depicts graphs showing the mean expression of ssAAV-CAG-NLS-GFP per GFP+ nuclei. N=4 animals per group.

FIGS. 20A-20D depict peripheral nerve transduction by AAV-PHP.S as compared to AAV9. FIG. 20A are whole-brain images (dorsal view, left and ventral view, right) of expression of AAV-PHP.S three weeks after IV administration of $1 \times 10^{12}$ vg/mouse of ssAAV-CAG-NLS-GFP packaged into the indicated capsid. Expression of GFP is indicated in grayscale. Note, despite using nuclear-localized GFP, expression of GFP is strong enough in the peripheral neuron axons entering the spinal cord and brain stem to be visible in these whole brain images. FIG. 20B is an image showing a transverse section of the spinal cord after transduction with $3 \times 10^{12}$ vg (total) of ssAAV-PHP.S:CAG-XFP-mix. FIG. 20C is a 3D projection image showing native fluorescence in a dorsal root ganglion of a mouse 4 weeks after injection of a mixture of $1 \times 10^{12}$ vg of ssAAV-PHP.S:CAG-mNeonGreen and $1 \times 10^{12}$ of ssAAV-PHP.S:CAGmTurquoise. FIG. 20D is an image showing AAV-PHP.S transducing cells within enteric nervous system after intravenous injection. native mNeonGreen fluorescence (bright signal) marks cells transduced by AAV-PHP.S. Images show a maximum intensity projection from the adult mouse intestine assessed 3 weeks after intravenous administration of 1×10$^{12}$ vg/mouse of ssAAV-PHP.S:CAG-mNeonGreen. Neurons are labeled with an antibody against pgp9.5 (grey staining) and nuclei labeled by DAPI are shown by dark staining. Individual channels are shown to the right. The top right image shows mNeonGreen expression in the enteric nervous system indicative of transduction by AAV-PHP.S:CAG-mNeonGreen.

FIG. 21 depicts evolution of the AAV-PHP.B 7-mer peptide and flanking sequences. The PHP.B 7-mer was inserted between AA588-589 of the AAV9 capsid. The five site saturation libraries (XXX1-XXX5) were generated by PCR, mixed in equal amounts and used to generate DNA. The DNA was then used to generate the AAV capsid libraries.

FIGS. 22A-22B show the amino acid sequences of AAV-PHP.N VP1 capsid (FIG. 22A) and AAV-PHP.S VP1 capsid (FIG. 22B). FIG. 22A: the AAV-PHP.S 7-mer insertion is underlined, and the two amino acids that differ from AAV-PHP.B 7-mer are highlighted. FIG. 22B: the AAV-PHP.S 7-mer is underlined.

FIG. 23A shows images of GFP expression in the whole brain. FIGS. 23B-23C are images of GFP expression in sagittal brain section. FIGS. 23D-23E are images of GFP expression in transverse spinal cord sections. Bright signals in the images indicate GFP expression.

FIGS. 24A-24C are images showing native GFP fluorescence from GFP protein expression in brain sections from adult mice injected with AAV-PHP.B (top) or AAV-PHP.N (bottom) in the cortex (FIG. 24A), striatum (FIG. 24B), and cerebellum (FIG. 24C). GFP expression is indicated by the bright signal. FIG. 24D shows the percentage of nuclei (DAPI$^+$) cells that expressed GFP after injection of AAV-PHP.B or AAV-PHP.N. FIG. 24E shows the percentage of NeuN$^+$ neurons (cortex or striatum) or Calbindin$^+$ (Calb) Purkinje neurons in the cerebellum that express GFP. FIG. 24F shows the percentage of S100b$^+$ cells that express GFP. FIG. 24G shows the mean fluorescence intensity of individual GFP$^+$ nuclei in the indicated brain region. The data was generated by taking the mean fluorescence value for each nuclei. *p<0.05, **p<0.01, student unpaired T test.

FIG. 25A are images showing native GFP fluorescence after transduction of 1×10$^{12}$ vg of ssAAV-CAG-NLS-GFP packaged into AAV9 or AAV-PHP.S. GFP expression is indicated by the bright signal. FIG. 25B shows the percentage of PGP9.5$^+$ DRG neurons that express nuclear GFP. FIG. 25C shows the mean median median fluorescence intensity of GFP$^+$ cells transduced with the indicated vector. FIG. 25D shows AAV-PHP.S transducing cardiac ganglia and cardiac muscle. AAV-PHP.S expression is indicated by the bright signal. p<0.01, **p<0.0001, student unpaired T test.

DETAILED DESCRIPTION

Figure 1:
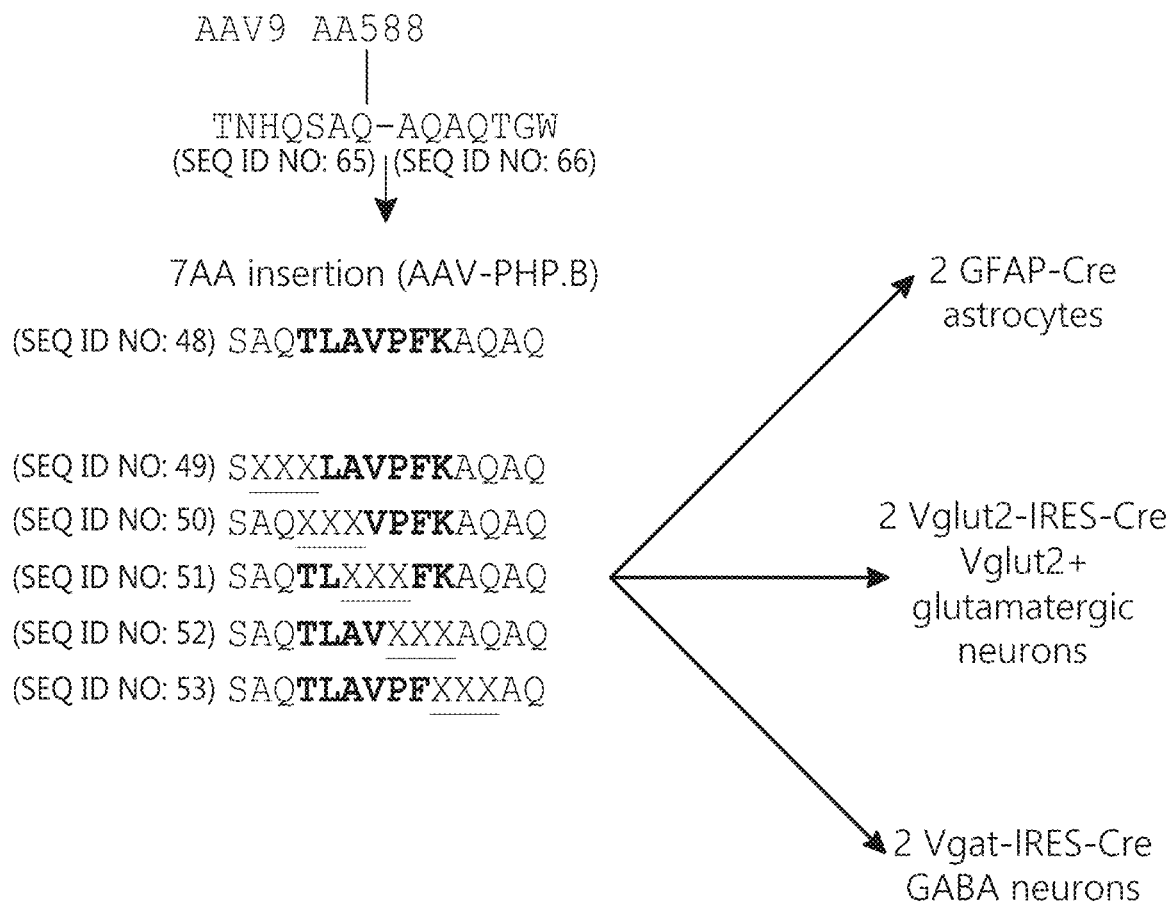
FIG. 1 depicts a schematic of the diversification strategy used to generate the AAV-PHP.B-XXX library. The AAV capsid containing the AAV-PHP.B 7-mer was diversified at 3 consecutive amino acid positions indicated by the XXX starting at 2 amino acids (hereafter referred to as "AA") from the 7mer insertion and continuing to +9 AA. Each XXX library was shifted by 2AA. A total of 5 XXX libraries were generated to span the 11 AA. The AAV-PHP.B-XXX PCR fragments were then assembled into the rAAV-Cap-in-cis-acceptor plasmid as described in U.S. Patent Publication 2015/0079038. And this rAAV genome was used to generate the AAV virus library which was then injected at a dose of $1 \times 10^{11}$ vg/mouse into adult GFAP-Cre, Vgat-IRES-Cre and Vglut-IRES-Cre mice, for selection of the variants that transduce astrocytes, GAGAergic neurons, and glutamatergic neurons, respectively. After two rounds of selection, numerous variants were found to be enriched in the sequences recovered from one or more of the Cre lines. One of those sequences, AAV-PHP.N (DGTLAVPFKAQ (SEQ ID NO: 4)) was chosen for characterization as an individual variant. The three amino acids of AAV-PHP.N that were varied from AAV-PHP.B are DGT and the sequence that differs from AAV-PHP.B is DG.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and make part of this disclosure The present application provides AAVs capable of delivering nucleic acids to a target environment, for example, a cell, a population of cells, a tissues, an organ, or a combination thereof, in a subject transducted with the AAVs. For example, the AAVs can be used to deliver nucleic acids to the nervous system, for example, central nervous system (CNS) and/or peripheral nervous system (PNS) of a subject. In some embodiments, the AAVs can be used to deliver nucleic acids to the heart of a subject, Also disclosed herein are peptides capable of directing AAVs to a target environment (e.g., the nervous system, the heart, or the combination thereof) in a subject, AAV capsid proteins comprising the peptides, compositions (e.g., pharmaceutical compositions) comprising AAV vectors having capsid proteins comprising the peptides, and the nucleic acid sequences encoding the peptides and AAV capsid proteins. In addition, methods of making and using the AAV vectors are also disclosed. In some embodiments, the AAV vectors are used to prevent and/or treat one or more diseases and disorders, for example diseases and disorders related to nervous system and/or the heart.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N.Y. 1989). For purposes of the present disclosure, the following terms are defined below.

The term "vector" as used herein, can refer to a vehicle for carrying or transferring a nucleic acid. Non-limiting examples of vectors include plasmids and viruses (for example, AAV viruses).

The term "construct," as used herein, refers to a recombinant nucleic acid that has been generated for the purpose of the expression of a specific nucleotide sequence(s), or that is to be used in the construction of other recombinant nucleotide sequences.

As used herein, the term "plasmid" refers to a nucleic acid that can be used to replicate recombinant DNA sequences within a host organism. The sequence can be a double stranded DNA.

As used herein, the terms "nucleic acid" and "polynucleotide" are interchangeable and refer to any nucleic acid, whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged methylene phosphonate, phosphorothioate, methylphosphonate, phosphorodithioate, bridged phosphorothioate or sultone linkages, and combinations of such linkages. The terms "nucleic acid" and "polynucleotide" also specifically include nucleic acids composed of bases other than the five biologically occurring bases (adenine, guanine, thymine, cytosine and uracil).

As used herein, amino acid "$X_n$" or "Bn" of a peptide sequence of two or more contiguous amino acids refers to an amino acid at $n^{th}$ (n is a positive integer) position of the peptide sequence. For example, in a peptide sequence of 11 contiguous amino acids $X_1X_2X_3X_4X_5X_6X_7X_8X_9X_{10}X_{11}$, $X_1$ is the amino acid at position 1 (i.e., the $1^{st}$ position) of the peptide sequence, $X_2$ is the amino acid at position 2 (i.e., the $2^{nd}$ position) of the peptide sequence, $X_3$ is the amino acid at position 3 (i.e., the $3^{rd}$ position) of the peptide sequence, $X_4$ is the amino acid at position 4 (i.e., the $4^{th}$ position) of the peptide sequence, $X_5$ is the amino acid at position 5 (i.e., the $5^{th}$ position) of the peptide sequence, $X_6$ is the amino acid at position 6 (i.e., the $6^{th}$ position) of the peptide sequence, $X_7$ is the amino acid at position 7 (i.e., the $7^{th}$ position) of the peptide sequence, $X_8$ is the amino acid at position 8 (i.e., the $8^{th}$ position) of the peptide sequence, $X_9$ is the amino acid at position 9 (i.e., the $9^{th}$ position) of the peptide sequence, $X_{10}$ is the amino acid at position 10 (i.e., the $10^{th}$ position) of the peptide sequence, and $X_{11}$ is the amino acid at position 11 (i.e., the $11^{th}$ position) of the peptide sequence. For example, if there is A at position 9, G at position 10 and Q at position 11 in the peptide sequence, it is described as that amino acids $X_9X_{10}X_{11}$ are AGQ. As another example, in a peptide sequence of $QAB_3B_4TSL$, it means that $B_3$ is the amino acid at postion 3 of the peptide sequence, and $B_4$ is the amino acid at position 4 of the peptide sequence.

The term "recombinase recognition sequence" or "recombinase recognition site" refers to a sequence of nucleic acid that is recognizable by a recombinase and can serve as the substrate for a recombination event catalyzed by said recombinase. The sequence can be, for example, double stranded DNA.

The term "virus genome" refers to a nucleic acid sequence that is flanked by cis acting nucleic acid sequences that mediate the packaging of the nucleic acid into a viral capsid. For AAVs and parvoviruses, for example it is known that the "inverted terminal repeats" (ITRs) that are located at the 5' and 3' end of the viral genome have this function and that the ITRs can mediate the packaging of heterologous, for example, non-wt virus genomes, into a viral capsid.

The term "element" refers to a separate or distinct part of something, for example, a nucleic acid sequence with a separate function within a longer nucleic acid sequence. The term "regulatory element" and "expression control element" are used interchangeably herein and refer to nucleic acid molecules that can influence the expression of an operably linked coding sequence in a particular host organism. These terms are used broadly to and cover all elements that promote or regulate transcription, including promoters, core elements required for basic interaction of RNA polymerase and transcription factors, upstream elements, enhancers, and response elements (see, e.g., Lewin, "Genes V" (Oxford University Press, Oxford) pages 847-873). Exemplary regulatory elements in prokaryotes include promoters, operator sequences and a ribosome binding sites. Regulatory elements that are used in eukaryotic cells can include, without limitation, transcriptional and translational control sequences, such as promoters, enhancers, splicing signals, polyadenylation signals, terminators, protein degradation signals, internal ribosome-entry element (IRES), 2A sequences, and the like, that provide for and/or regulate expression of a coding sequence and/or production of an encoded polypeptide in a host cell.

As used herein, the term "variant" refers to a polynucleotide or polypeptide having a sequence substantially similar to a reference polynucleotide or polypeptide. In the case of a polynucleotide, a variant can have deletions, substitutions, additions of one or more nucleotides at the 5' end, 3' end, and/or one or more internal sites in comparison to the reference polynucleotide. Similarities and/or differences in sequences between a variant and the reference polynucleotide can be detected using conventional techniques known in the art, for example polymerase chain reaction (PCR) and hybridization techniques. Variant polynucleotides also include synthetically derived polynucleotides, such as those generated, for example, by using site-directed mutagenesis. Generally, a variant of a polynucleotide, including, but not limited to, a DNA, can have at least about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to the reference polynucleotide as determined by sequence alignment programs known by skilled artisans. In the case of a polypeptide, a variant can have deletions, substitutions, additions of one or more amino acids in comparison to the reference polypeptide. Similarities and/or differences in sequences between a variant and the reference polypeptide can be detected using conventional techniques known in the art, for example Western blot. Generally, a variant of a polypeptide, can have at least about 60%, about 65%, about 70%, about 75%, about 80%, about 85%, about 90%, about 91%, about 92%, about 93%, about 94%, about 95%, about 96%, about 97%, about 98%, about 99% or more sequence identity to the reference polypeptide as determined by sequence alignment programs known by skilled artisans.

The term "AAV" or "adeno-associated virus" refers to a Dependoparvovirus within the Parvoviridae genus of viruses. For example, the AAV can be an AAV derived from a naturally occurring "wild-type" virus, an AAV derived from a rAAV genome packaged into a capsid derived from capsid proteins encoded by a naturally occurring cap gene and/or a rAAV genome packaged into a capsid derived from capsid proteins encoded by a non-natural capsid cap gene, for example, AAV-PHP.N and AAV-PHP.S. As disclosed herein, the terms "AAV-PHP.eB", "AAV-PHP.N", and "AAV-PHP.B-DGT" are used interchangeably to refer to an AAV variant having a non-natural capsid protein comprising a 11-mer amino acid sequence DGTLAVPFKAQ (SEQ ID NO: 4, which is referred to herein as "PHP.eB", "PHP.N" "PHP.B-DGT" sequence, respectively).

The term "rAAV" refers to a "recombinant AAV". In some embodiments, a recombinant AAV has an AAV genome in which part or all of the rep and cap genes have been replaced with heterologous sequences.

The term "rep-cap helper plasmid" refers to a plasmid that provides the viral rep and cap gene functions. This plasmid can be useful for the production of AAVs from rAAV genomes lacking functional rep and/or the capsid gene sequences.

The term "vector" is defined as a vehicle for carrying or transferring a nucleic acid. Non-limiting examples of vectors include plasmids and viruses.

The term "cap gene" refers to the nucleic acid sequences that encode capsid proteins that form, or contribute to the formation of, the capsid, or protein shell, of the virus. In the case of AAV, the capsid protein may be VP1, VP2, or VP3. For other parvoviruses, the names and numbers of the capsid proteins can differ.

The term "rep gene" refers to the nucleic acid sequences that encode the non-structural proteins (rep78, rep68, rep52 and rep40) required for the replication and production of virus.

A "library" may be in the form of a multiplicity of linear nucleic acids, plasmids, viral particles or viral vectors. A library will include at least two linear nucleic acids.

When the inserted nucleic acid sequences are randomly generated, N=A, C, G, or T; K=G or T; M=A or C.

Unless specified otherwise, the left-hand end of any single-stranded polynucleotide sequence discussed herein is the 5' end; the left-hand direction of double-stranded polynucleotide sequences is referred to as the 5' direction.

The term "naturally occurring" as used herein refers to materials which are found in nature or a form of the materials that is found in nature.

Standard techniques can be used for recombinant DNA, oligonucleotide synthesis, and tissue culture and transformation (e.g., electroporation, lipofection). Enzymatic reactions and purification techniques can be performed according to manufacturer's specifications or as commonly accomplished in the art or as described herein. The foregoing techniques and procedures can be generally performed according to conventional methods well known in the art and as described in various general and more specific references that are cited and discussed throughout the present specification. See, e.g., Sambrook et al., *Molecular Cloning: A Laboratory Manual* (2d ed., Cold Spring Harbor Laboratory Press, Cold Spring Harbor, N.Y. (1989)), which is incorporated herein by reference for any purpose. Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

As used herein, a "subject" refers to an animal that is the object of treatment, observation or experiment. "Animal" includes cold- and warm-blooded vertebrates and invertebrates such as fish, shellfish, reptiles, and in particular, mammals. "Mammal," as used herein, refers to an individual belonging to the class Mammalia and includes, but not limited to, humans, domestic and farm animals, zoo animals, sports and pet animals. Non-limiting examples of mammals include mice; rats; rabbits; guinea pigs; dogs; cats; sheep; goats; cows; horses; primates, such as monkeys, chimpanzees and apes, and, in particular, humans. In some embodiments, the mammal is a human. However, in some embodiments, the mammal is not a human.

As used herein, the term "treatment" refers to an intervention made in response to a disease, disorder or physiological condition manifested by a patient, particularly a patient suffering from one or more serotonin-related diseases. The aim of treatment may include, but is not limited to, one or more of the alleviation or prevention of symptoms, slowing or stopping the progression or worsening of a disease, disorder, or condition and the remission of the disease, disorder or condition. The term "treat" and "treatment" includes, for example, therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors. In some embodiments, "treatment" refers to both therapeutic treatment and prophylactic or preventative measures. Those in need of treatment include those already affected by a disease or disorder or undesired physiological condition as well as those in which the disease or disorder or undesired physiological condition is to be prevented. For example, in some embodiments treatment may enhance or reduce the level of serotonin in the subject, thereby to reduce, alleviate, or eradicate the symptom(s) of the disease(s). As used herein, the term "prevention" refers to any activity that reduces the burden of the individual later expressing those serotonin-related disease symptoms. This can take place at primary, secondary and/or tertiary prevention levels, wherein: a) primary prevention avoids the development of symptoms/disorder/condition; b) secondary prevention activities are aimed at early stages of the condition/disorder/symptom treatment, thereby increasing opportunities for interventions to prevent progression of the condition/disorder/symptom and emergence of symptoms; and c) tertiary prevention reduces the negative impact of an already established condition/disorder/symptom by, for example, restoring function and/or reducing any condition/disorder/symptom or related complications. The term "prevent" does not require the 100% elimination of the possibility of an event. Rather, it denotes that the likelihood of the occurrence of the event has been reduced in the presence of the compound or method.

As used herein, the term "effective amount" refers to an amount sufficient to effect beneficial or desirable biological and/or clinical results.

"Pharmaceutically acceptable" carriers are ones which are nontoxic to the cell or mammal being exposed thereto at the dosages and concentrations employed. "Pharmaceutically acceptable" carriers can be, but not limited to, organic or inorganic, solid or liquid excipients which is suitable for the selected mode of application such as oral application or injection, and administered in the form of a conventional pharmaceutical preparation, such as solid such as tablets, granules, powders, capsules, and liquid such as solution, emulsion, suspension and the like. Often the physiologically acceptable carrier is an aqueous pH buffered solution such as phosphate buffer or citrate buffer. The physiologically acceptable carrier may also comprise one or more of the following: antioxidants including ascorbic acid, low molecular weight (less than about 10 residues) polypeptides, proteins, such as serum albumin, gelatin, immunoglobulins; hydrophilic polymers such as polyvinylpyrrolidone, amino acids, carbohydrates including glucose, mannose, or dextrins, chelating agents such as EDTA, sugar alcohols such as mannitol or sorbitol, salt-forming counterions such as sodium, and nonionic surfactants such as Tween™, polyethylene glycol (PEG), and Pluronics™. Auxiliary, stabilizer, emulsifier, lubricant, binder, pH adjustor controller, isotonic agent and other conventional additives may also be added to the carriers.

Targeting Sequences

Disclosed herein are targeting peptides capable of directing AAV (for example, directing the AAV for the purpose of delivering one or more nucleic acids) to target environments in a subject. The target environment can be, for example, a cell, a cell population, one or more tissues, one or more organs, or a combination thereof in the subject. In some embodiments, the target environment is the central nervous system (CNS). In some embodiments, the target environment is the peripheral nervous system (PNS). In some embodiments, the target environment is the heart. In some embodiments, the targeting peptide is capable directing AAV to, or primarily to, the CNS of the subject (referred herein as a "CNS targeting peptide"). In some embodiments, the targeting peptide is capable directing AAV to, or primarily to, the PNS of the subject (referred herein as a "PNS targeting peptide"). In some embodiments, the targeting peptide is capable directing AAV to, or primarily to, the heart of the subject (referred herein as a "heart targeting peptide"). In some embodiments, the targeting peptide is a CNS targeting peptide. In some embodiments, the targeting peptide is a PNS targeting peptide. In some embodiments, the targeting peptide is a heart targeting peptide. For example, the CNS targeting peptide can, in some embodiments, direct AAV to deliver nucleic acids to neurons, glia, endothelia cells, astrocytes, cerebellar Purkinje cells, or a combination thereof, of the CNS. In some embodiments, the targeting peptide is capable of directing AAV to deliver nucleic acid to the CNS, the heart (e.g., cardiomyocytes in the heart), peripheral nerves, or a combination thereof, in the subject. In some embodiments, the subject is an adult, for example, a subject who is three years and older.

The targeting peptide (e.g., the CNS targeting peptide, the PNS targeting peptide, and the heart targeting peptide) can vary in length. For example, the targeting peptide can be, or be at least, three, four, five, six, seven, eight, nine, ten, eleven, twelve, fifteen, eighteen, twenty, twenty-five, thirty, or a range between any two of these values, amino acids long. In some embodiments, the targeting peptide is, or is about, seven amino acids long. In some embodiments, the targeting peptide is, or is about, eleven amino acids long. In some embodiments, the targeting peptide is, or is about, seven to eleven amino acids long.

In some embodiments, the targeting peptide comprises or consists of a sequence of 11 contiguous amino acids $X_1X_2X_3X_4X_5X_6X_7X_8X_9X_{10}X_{11}$, wherein $X_1$ is D, A, E, Q, N, G, or S;
$X_2$ is G, N, S, T, Q, or V;
$X_3$ is T, S or N;
$X_4$ is L or V;
$X_5$ is A, S, Q, P, or T;
$X_6$ is V, T, Q, N, L, or M;
$X_7$ is P;
$X_8$ is F, Y, V, L, C, or S;
$X_9$ is K, R or S; and
each of $X_{10}$ and $X_{11}$ is independently any amino acid.

In some embodiments, the targeting peptide is not, or does not comprise, the amino acid sequence AQTLAVPFKAQ (SEQ ID NO: 1). In some embodiments of the targeting peptide, $X_{10}$ and $X_{11}$ can independently be any amino acids, for example any of the standard amino acids. As used herein, standard amino acids include Alanine (abbreviated as "Ala" or "A"), Arginine (abbreviated as "Arg" or "R"), Asparagine (abbreviated as "Asn" or "N"), Aspartic acid (abbreviated as "Asp" or "D"), Cysteine (abbreviated as "Cys" or "C"), Glutamic acid (abbreviated as "Glu" or "E"), Glutamine (abbreviated as "Gln" or "Q"), Glycine (abbreviated as "Gly" or "G"), Histidine (abbreviated as "His" or "H"), Isoleucine (abbreviated as "Ile" or "I"), Leucine (abbreviated as "Leu" or "L"), Lysince (abbreviated as "Lys" or "K"), Methionine (abbreviated as "Met" or "M"), Phenylalanine (abbreviated as "Phe" or "F"), Proline (abbreviated as "Pro" or "P"), Serine (abbreviated as "Ser" or "S"), Threonine (abbreviated as "Thr" or "T"), Tryptophan "abbreviated as "Trp" or "W"), Tyrosine (abbreviated as "Tyr" or "Y"), Valine (abbreviated as "Val" or "V"). In some embodiments, $X_{10}$ is A or N. In some embodiments, $X_{11}$ is Q or P. $X_{10}$ and $X_{11}$ can be the same or different amino acid. In some embodiments, $X_1$ is D. In some embodiments, $X_2$ is G. In some embodiments, $X_3$ is T. In some embodiments, $X_4$ is L. In some embodiments, $X_6$ is V or T. In some embodiments, $X_8$ is F. In some embodiments, the amino acid sequence $X_4X_5X_6X_7X_8X_9X_{10}X_{11}$ is LAVPFKAQ (SEQ ID NO: 80). In some embodiments, the amino acid sequence $X_1X_2X_3$ is DGT, GGT, EGT, DST, EST, QGT, NQT, SGS, SGN, ATT, AVT, or ART. In some embodiments, the amino acid sequence $X_1X_2$ is AQ, and amino acids $X_6X_7X_8X_9X_{10}X_{11}$ are VPFKAQ (SEQ ID NO: 81). In some embodiments, $X_3$ is T and $X_4$ is L. In some embodiments, $X_5$ is A. In some embodiments, the amino acid sequence $X_1X_2$ is AQ, the amino acid sequence $X_3X_4$ is TL, and the amino acid sequence $X_8X_9X_{10}X_{11}$ is FKAQ (SEQ ID NO: 82). In some embodiments, the amino acid sequence $X_5X_6X_7$ is AVP, ATP, AQP, QQP, PQP, SNP, STP, SQP, QLP, TMP, or TTP. In some embodiments, the amino acid seqeunce $X_1X_2X_3X_4X_5X_6$ is AQTLAV (SEQ ID NO: 83) and the amino acid sequence $X_{10}X_{11}$ is AQ. In some embodiments, amino acids $X_7X_8X_9$ are PFK. In some embodiments, the amino acid sequence $X_1X_2X_3X_4X_5X_6X_7X_8$ is AQTLAVPF (SEQ ID NO: 84). In some embodiments, the amino acid sequence $X_9X_{10}X_{11}$ is KAQ, KAP, or SNP. In some embodiments, the sequence of 11 contiguous amino acids $X_1X_2X_3X_4X_5X_6X_7X_8X_9X_{10}X_{11}$ is DGTLATPFKXX (X can be any amino acid, SEQ ID NO: 68). In some embodiments, the sequence of 11 contiguous amino acids $X_1X_2X_3X_4X_5X_6X_7X_8X_9X_{10}X_{11}$ is GGTLATPFKAQ (SEQ ID NO: 10). Various combinations of the embodiments described herein are encompassed in the scope of the present disclosure. For example, when $X_{10}$ is A, $X_{11}$ can be Q or P; and when $X_1$ is D, $X_2$ can be any one of G, N, S, T, and V. As another example, when $X_3$ is T and $X_4$ is L, $X_5$ can be A.

In some embodiments, $X_4$, $X_5$, $X_6$, $X_7$, $X_8$, $X_9$, $X_{10}$, and $X_{11}$ are L, A, V, P, F, K, A, and Q, respectively; and $X_3$ is T, S, or N. In some embodiments, it is advantageous for $X_3$ to be T. In some embodiments, the amino acid sequence $X_1X_2X_3$ is AQT, DGT, GGT, EGT, DST, EST, QGT, NQT, SGS, SGN, ATT, AVT, or ART.

In some embodiments, $X_1$ is A and $X_2$ is Q; $X_6$, $X_7$, $X_8$, $X_9$, $X_{10}$, and $X_{11}$ are V, P, F, K, A, Q, respectively; and $X_3$ is T and $X_4$ is L. In some embodiments, the amino acid sequence $X_3X_4X_5$ is TLA.

In some embodiments, $X_1$ is A, $X_2$ is Q, $X_3$ is T, $X_4$ is L, $X_8$ is F, $X_9$ is K, $X_{10}$ is A, and $X_{11}$ is Q, and the amino acid sequence $X_5X_6X_7$ is AVP, ATP, AQP, QQP, PQP, SNP, STP, SQP, QLP, TMP, or TTP.

In some embodiments, the sequence of 11 contiguous amino acids is AQTLAVPFKAQ (SEQ ID NO: 1).

In some embodiments, $X_1$ is A, $X_2$ is Q, $X_3$ is T, $X_4$ is L, $X_5$ is A, $X_6$ is V, $X_7$ is P, and $X_8$ is F, and the amino acid sequence $X_9X_{10}X_{11}$ is KAQ, KAP, or SNP.

A targeting peptide can also comprise, or consists of, at least 4 contiguous amino acids of any one of the targeting peptides disclosed herein, for example, the targeting peptide of SEQ ID NOs: 1-44, 48-53 and 65-68. In some embodiments, the targeting peptide comprises, or consists of, 4, 5, or 6 of contiguous amino acids of one of SEQ ID NO: 37-44 and 65-68. In some embodiments, the targeting peptide comprises, or consists of, 4, 5, 6, 7, 8, 9, or 10 of contiguous amino acids of one of SEQ ID NO: 1-36.

The targeting peptide can also comprise, or consists of, at least 4 contiguous amino acids of the sequence QAVRTSL (SEQ ID NO: 37). In some embodiments, the targeting peptide comprises, or consists of, 4, 5, or 6 of contiguous amino acids of the sequence QAVRTSL (SEQ ID NO: 37). For example, the targeting peptide can comprise or consist of an amino acid sequence selected from QAVR (SEQ ID NO: 85), AVRT (SEQ ID NO: 86), VRTS (SEQ ID NO: 87), RTSL (SEQ ID NO: 88), QAVRT (SEQ ID NO: 89), AVRTS (SEQ ID NO: 90), VRTSL (SEQ ID NO: 91), QAVRTS (SEQ ID NO: 92), and AVRTSL (SEQ ID NO: 93). In some embodiments, the targeting peptide can also comprise, or consiste of, an amino acid sequence that has one or two mismatch with SEQ ID NO: 37. For example, the targeting peptide can comprise, or consist of, the amino acid sequence of QAB$_3$B$_4$TSL, wherein B$_3$ and B$_4$ can independently be any of the standard amino acids. In some embodiments, B$_3$ is not V, B$_4$ is not R, or both. As another example, the targeting peptide can comprise, or consist of, the amino acid sequence of QAVRB$_5$SL, wherein B$_5$ can be any of the standard amino acids. In some embodiments, B$_5$ is not T.

The targeting peptide disclosed herein can be a standalone peptide, or can be conjugated to or part of a nanoparticle, a second molecule, a viral capsid protein, or a combination thereof. In some embodiments, the targeting peptide is inserted between amino acids 588 and 589 of AAV9 capsid sequence (SEQ ID NO: 45).

In some embodiments, the targeting peptide comprises or consists of four or more contiguous amino acids of one of SEQ ID NOs: 1-44, 48-53 and 65-68. In some embodiments, the CNS targeting peptide comprises or consists of 4, 5 or 6 amino acids of any of SEQ ID NOs: 1-44, 48-53 and 65-68. In some embodiments, 2 or fewer amino acids can be altered of any of the SEQ ID NOs: 1-44, 48-53 and 65-68. In some embodiments, the alteration is a conservative alteration (within any of the targeting sequences provided herein). In some embodiments, the alteration is a deletion or insertion of one or two amino acids (within any of the targeting sequences provided herein). In some embodiments, the targeting peptide can have at least 75%, 80%, 85%, 90%, 95%, 98%, 99%, or higher sequence identity to one of the targeting sequences provided herein. In some embodiments, the targeting peptide may be different from one of the targeting sequence disclosed herein by one, two, three, four, five, six, or more amino acids.

In some embodiments, the targeting peptide comprises, consists, or consists essentially of any one or more of the above sequences. In some embodiments, the targeting peptide is inserted into a longer peptide, as described herein. Table 1 provides non-limiting examples of targeting peptides.

TABLE 1

Exemplary examples of targeting peptides disclosed herein (X can be any of the standard amino acids)

| Targeting peptides | SEQ ID NO. |
|---|---|
| AQTLAVPFKAQ | SEQ ID NO: 1 |
| AQSVSKPFLAQ | SEQ ID NO: 2 |
| AQFTLTTPKAQ | SEQ ID NO: 3 |
| DGTLAVPFKAQ | SEQ ID NO: 4 |
| ESTLAVPFKAQ | SEQ ID NO: 5 |
| GGTLAVPFKAQ | SEQ ID NO: 6 |
| AQTLATPFKAQ | SEQ ID NO: 7 |
| ATTLATPFKAQ | SEQ ID NO: 8 |
| DGTLATPFKAQ | SEQ ID NO: 9 |
| GGTLATPFKAQ | SEQ ID NO: 10 |
| SGSLAVPFKAQ | SEQ ID NO: 11 |
| AQTLAQPFKAQ | SEQ ID NO: 12 |
| AQTLQQPFKAQ | SEQ ID NO: 13 |

TABLE 1-continued

Exemplary examples of targeting peptides disclosed herein (X can be any of the standard amino acids)

| Targeting peptides | SEQ ID NO. |
|---|---|
| AQTLSNPFKAQ | SEQ ID NO: 14 |
| AQTLAVPFSNP | SEQ ID NO: 15 |
| QGTLAVPFKAQ | SEQ ID NO: 16 |
| NQTLAVPFKAQ | SEQ ID NO: 17 |
| EGSLAVPFKAQ | SEQ ID NO: 18 |
| SGNLAVPFKAQ | SEQ ID NO: 19 |
| EGTLAVPFKAQ | SEQ ID NO: 20 |
| DSTLAVPFKAQ | SEQ ID NO: 21 |
| AVTLAVPFKAQ | SEQ ID NO: 22 |
| AQTLSTPFKAQ | SEQ ID NO: 23 |
| AQTLPQPFKAQ | SEQ ID NO: 24 |
| AQTLSQPFKAQ | SEQ ID NO: 25 |
| AQTLQLPFKAQ | SEQ ID NO: 26 |
| AQTLTMPFKAQ | SEQ ID NO: 27 |
| AQTLTTPFKAQ | SEQ ID NO: 28 |
| AQYTLSQGWAQ | SEQ ID NO: 29 |
| AQMNATKNVAQ | SEQ ID NO: 30 |
| AQVSGGHHSAQ | SEQ ID NO: 31 |
| AQTLPQPFKAQ | SEQ ID NO: 32 |
| AQTLATPFKAQ | SEQ ID NO: 33 |
| AQTLTMPFKAQ | SEQ ID NO: 34 |
| AQTLTAPFKAQ | SEQ ID NO: 35 |
| AQTLSKPFKAQ | SEQ ID NO: 36 |
| QAVRTSL | SEQ ID NO: 37 |
| YTLSQGW | SEQ ID NO: 38 |
| LAKERLS | SEQ ID NO: 39 |
| TLAVPFK | SEQ ID NO: 40 |
| SVSKPFL | SEQ ID NO: 41 |
| FTLTTPK | SEQ ID NO: 42 |
| MNSTKNV | SEQ ID NO: 43 |
| VSGGHHS | SEQ ID NO: 44 |
| SAQTLAVPFKAQAQ | SEQ ID NO: 48 |
| SXXXLAVPFKAQAQ | SEQ ID NO: 49 |
| SAQXXXVPFKAQAQ | SEQ ID NO: 50 |
| SAQTLXXXFKAQAQ | SEQ ID NO: 51 |
| SAQTLAVXXXAQAQ | SEQ ID NO: 52 |
| SAQTLAVPFXXXAQ | SEQ ID NO: 53 |

Also disclosed herein are nucleic acids comprising the nucleotide sequences that encode one or more of the targeting peptides disclosed herein.

In some embodiments, the targeting peptide is part of an AAV, for example part of an AAV capsid protein (SEQ ID NO: 45). Provided herein are AAV capsid proteins comprising one or more of the targeting peptides disclosed herein. For example, the AAV capsid protein can comprise a targeting peptide portion comprising at least 4 contiguous amino acids of the sequence QAVRTSL (SEQ ID NO: 37). In some embodiments, the AAV capsid protein comprises a targeting peptide portion comprising, or consisting of, 4, 5, or 6 of contiguous amino acids of the sequence QAVRTSL (SEQ ID NO: 37).

Also disclosed herein are AAV capsid proteins comprising a targeting peptide portion that comprises a sequence of 11 contiguous amino acids $X_1X_2X_3X_4X_5X_6X_7X_8X_9X_{10}X_{11}$, wherein $X_1$ is D, A, E, Q, N, G, or S;
$X_2$ is G, N, S, T, Q, or V;
$X_3$ is T, S or N;
$X_4$ is L or V;
$X_5$ is A, S, Q, P, or T;
$X_6$ is V, T, Q, N, L, or M;
$X_7$ is P;
$X_8$ is F, Y, V, L, C, or 5;
$X_9$ is K, R or S; and
each of $X_{10}$ and $X_{11}$ is independently any amino acid.

In some embodiments, the targeting peptide is not, or does not comprise, amino acid sequence AQTLAVPFKAQ (SEQ ID NO: 1). In some embodiments, the AAV capsid protein does not comprise, amino acid sequence AQTLAVPFKAQ (SEQ ID NO: 1). As described herein, $X_{10}$ and $X_{11}$ can independently be any amino acids, for example any of the standard amino acids. In some embodiments, $X_{10}$ is A or N. In some embodiments, $X_{11}$ is Q or P. In some embodiments, $X_1$ is D. In some embodiments, $X_2$ is G. In some embodiments, $X_3$ is T. In some embodiments, $X_4$ is L. In some embodiments, $X_6$ is V or T. In some embodiments, $X_8$ is F. In some embodiments, the amino acid sequence $X_4X_5X_6X_7X_8X_9X_{10}X_{11}$ is LAVPFKAQ (SEQ ID NO: 80). In some embodiments, the amino acid sequence $X_1X_2X_3$ is DGT, GGT, EGT, DST, EST, QGT, NQT, SGS, SGN, ATT, AVT, or ART. In some embodiments, $X_1$ is A, $X_2$ is Q, and the amino acid sequence $X_6X_7X_8X_9X_{10}X_{11}$ is VPFKAQ (SEQ ID NO: 81). In some embodiments, $X_3$ is T and $X_4$ is L. In some embodiments, $X_5$ is A. In some embodiments, $X_1$ is A, $X_2$ is Q, $X_3$ is T, $X_4$ is L, and the amino acid sequence $X_8X_9X_{10}X_{11}$ is FKAQ (SEQ ID NO: 82). In some embodiments, the amino acid sequence $X_5X_6X_7$ is AVP, ATP, AQP, QQP, PQP, SNP, STP, SQP, QLP, TMP, or TTP. In some embodiments, the amino acid sequence $X_1X_2X_3X_4X_5X_6$ is AQTLAV (SEQ ID NO: 83), $X_{10}$ is A, and $X_{11}$ is Q. In some embodiments, the amino acid sequence $X_7X_8X_9$ is PFK. In some embodiments, the amino acid sequence $X_1X_2X_3X_4X_5X_6X_7X_8$ is AQTLAVPF (SEQ ID NO: 84). In some embodiments, the amino acid sequence $X_9X_{10}X_{11}$ is KAQ, KAP, or SNP. In some embodiments, the sequence of 11 contiguous amino acids $X_1X_2X_3X_4X_5X_6X_7X_8X_9X_{10}X_{11}$ is DGTLATPFKXX (X can be any amino acid, SEQ ID NO: 68). In some embodiments, the sequence of 11 contiguous amino acids $X_1X_2X_3X_4X_5X_6X_7X_8X_9X_{10}X_{11}$ is GGTLATPFKAQ (SEQ ID NO: 10). Various combinations of the embodiments described herein are encompassed in the scope of the present disclosure. For example, when $X_{10}$ is A, $X_{11}$ can be Q or P; and when $X_1$ is D, $X_2$ can be any one of G, N, S, T, and V. As another example, when $X_3$ is T and $X_4$ is L, $X_5$ can be A.

In some embodiments, $X_4$, $X_5$, $X_6$, $X_7$, $X_8$, $X_9$, $X_{10}$, and $X_{11}$ are L, A, V, P, F, K, A, and Q, respectively; and $X_3$ is T, S, or N. In some embodiments, it is advantageous for $X_3$ to be T. In some embodiments, the amino acid sequence $X_1X_2X_3$ is AQT, DGT, GGT, EGT, DST, EST, QGT, NQT, SGS, SGN, ATT, AVT, or ART.

In some embodiments, $X_1$ is A and $X_2$ is Q; $X_6$, $X_7$, $X_8$, $X_9$, $X_{10}$, and $X_{11}$ are V, P, F, K, A, Q, respectively, and $X_3$ is T and $X_4$ is L. In some embodiments, the amino acid sequence $X_3X_4X_5$ is TLA.

In some embodiments, $X_1$ is A, $X_2$ is Q, $X_3$ is T, $X_4$ is L, $X_8$ is F, $X_9$ is K, $X_{10}$ is A, and $X_{11}$ is Q, and the amino acid sequence $X_5X_6X_7$ is AVP, ATP, AQP, QQP, PQP, SNP, STP, SQP, QLP, TMP, or TTP.

In some embodiments, the sequence of 11 contiguous amino acids is AQTLAVPFKAQ (SEQ ID NO: 1).

In some embodiments, $X_1$ is A, $X_2$ is Q, $X_3$ is T, $X_4$ is L, $X_5$ is A, $X_6$ is V, $X_7$ is P, and $X_8$ is F, and the amino acid sequence $X_9X_{10}X_{11}$ is KAQ, KAP, or SNP.

The targeting peptide portion of the capsid protein can comprise, or consist of, the sequence of any one of the targeting peptides disclosed herein, or at least 4 contiguous amino acids of any one of the targeting peptides disclosed herein. In some embodiments, the AAV capsid protein comprises a targeting peptide portion that comprises, or consists of, at least 4 contiguous amino acids of any one of SEQ ID NOs: 1-44, 48-53 and 65-68. In some embodiments, the AAV capsid protein comprises a targeting peptide portion that comprises, or consists of, 4, 5, or 6 of contiguous amino acids of SEQ ID NO: 37-44 and 65-68. In some embodiments, the AAV capsid protein comprises a targeting peptide portion that comprises, or consists of, 4, 5, 6, 7, 8, 9, or 10 of contiguous amino acids of SEQ ID NO: 1-36.

In some embodiments, the targeting peptide is part of an AAV9 capsid sequence SEQ ID NO: 45. In some embodiments, the targeting peptide can be linked to any molecule that should be targeted as desired. In some embodiments, the targeting peptide can be linked or conjugated, without limitation, to a recombinant protein, an antibody, a cell, a diagnostic, a therapeutic, a nanomolecule, or a combination thereof. In some embodiments, the capsid protein comprises, or consists of, the sequence of SEQ ID NO: 46 or SEQ ID NO: 47.

In some embodiments, the targeting peptide can be inserted into any desired section of a protein. In some embodiments, the targeting peptide can be inserted into a capsid protein. In some embodiments, the targeting peptide is inserted on a surface of the desired protein. In some embodiments, the targeting peptide is inserted into the primary sequence of the protein. In some embodiments, the targeting peptide is linked to the protein. In some embodiments, the targeting peptide is covalently linked to the protein. In some embodiments, the targeting peptide is inserted into an unstructured loop of the desired protein. In some embodiments, the unstructured loop can be one identified via a structural model of the protein.

Also provided herein are nucleic acids comprising nucleotide sequences that encode one or more of the AAV capsid proteins disclosed herein.

Adeno-Associated Virus (AAV) Vectors and Recombinant AAVs

Adeno-associated virus (AAV) is a replication-deficient parvovirus, the single-stranded DNA genome of which is about 4.7 kb in length including 145 nucleotide inverted terminal repeat (ITRs). The ITRs play a role in integration of the AAV DNA into the host cell genome. When AAV infects a host cell, the viral genome integrates into the host's chromosome resulting in latent infection of the cell. In a natural system, a helper virus (for example, adenovirus or herpesvirus) provides genes that allow for production of AAV virus in the infected cell. In the case of adenovirus, genes E1A, E1B, E2A, E4 and VA provide helper functions. Upon infection with a helper virus, the AAV provirus is rescued and amplified, and both AAV and adenovirus are produced. In the instances of recombinant AAV vectors having no Rep and/or Cap genes, the AAV can be non-integrating.

AAV vectors that comprise coding regions of one or more proteins of interest are provided. The AAV vector can include a 5' inverted terminal repeat (ITR) of AAV, a 3' AAV ITR, a promoter, and a restriction site downstream of the promoter to allow insertion of a polynucleotide encoding one or more proteins of interest, wherein the promoter and the restriction site are located downstream of the 5' AAV ITR and upstream of the 3' AAV ITR. In some embodiments, the AAV vector includes a posttranscriptional regulatory element downstream of the restriction site and upstream of the 3' AAV ITR. In some embodiments, the AAV vectors disclosed herein can be used as AAV transfer vectors carrying a transgene encoding a protein of interest for producing recombinant AAV viruses that can express the protein of interest in a host cell.

rAAV genomes are provided herein. The genome can, for example, comprise at least one inverted terminal repeat configured to allow packaging into a vector and a cap gene. In some embodiments, it can further include a sequence within a rep gene required for expression and splicing of the cap gene. In some embodiments, the genome can further include a sequence capable of expressing VP3. In some embodiments, the only protein that is expressed is VP3 (the smallest of the capsid structural proteins that makes up most of the assembled capsid—the assembled capsid is composed of 60 units of VP proteins, ~50 of which are VP3). In some embodiments, VP3 expression alone is adequate to allow the method of screening to be adequate.

Generation of the viral vector can be accomplished using any suitable genetic engineering techniques well known in the art, including, without limitation, the standard techniques of restriction endonuclease digestion, ligation, transformation, plasmid purification, and DNA sequencing, for example as described in Sambrook et al. (Molecular Cloning: A Laboratory Manual. Cold Spring Harbor Laboratory Press, N.Y. (1989)).

The viral vector can incorporate sequences from the genome of any known organism. The sequences can be incorporated in their native form or can be modified in any way to obtain a desired activity. For example, the sequences can comprise insertions, deletions or substitutions.

In some embodiments, the viral vectors can include additional sequences that make the vectors suitable for replication and integration in eukaryotes. In other embodiments, the viral vectors disclosed herein can include a shuttle element that makes the vectors suitable for replication and integration in both prokaryotes and eukaryotes. In some embodiments, the viral vectors can include additional transcription and translation initiation sequences, such as promoters and enhancers; and additional transcription and translation terminators, such as polyadenylation signals. Various regulatory elements that can be included in an AAV vector have been described in details in US Patent Publication 2012/0232133 which is hereby incorporated by reference in its entirety.

Disclosed herein are AAV vectors that comprise targeting peptides capable of directing the AAVs to target environments (e.g., CNS, PNS, and the heart) in a subject. In some embodiments, the targeting peptide is part of the capsid protein of the AAV vector. The AAV vector can, in some embodiments, comprise a protein comprising comprises at least 4 contiguous amino acids of the sequence QAVRTSL (SEQ ID NO: 37). In some embodiments, the capsid of the AAV can comprise an amino acid sequence that comprises at least 4 contiguous amino acids of the sequence QAVRTSL (SEQ ID NO: 37). In some embodiments, the amino acid sequence is a part of a capsid protein of the AAV vector. In some embodiments, the sequence QAVRTSL (SEQ ID NO: 37) is inserted between AA588-589 of an AAV sequence of the vector (SEQ ID NO: 45). In some embodiments, the sequence QAVRTSL (SEQ ID NO: 37) is inserted between AA586-592 of an AAV sequence of the vector (SEQ ID NO: 45). In some embodiments, the sequence QAVRTSL (SEQ ID NO: 37) further comprises at least two of amino acids 587, 588, 589, and 590 of SEQ ID NO: 45.

In some embodiments, the AAV vector, for example the capsid protein of the AAV vector, comprises a sequence of 11 contiguous amino acids $X_1X_2X_3X_4X_5X_6X_7X_8X_9X_{10}X_{11}$, wherein
$X_1$ is D, A, E, Q, N, G, or S;
$X_2$ is G, N, S, T, Q, or V;
$X_3$ is T, S or N;
$X_4$ is L or V;
$X_5$ is A, S, Q, P, or T;
$X_6$ is V, T, Q, N, L, or M;
$X_7$ is P;
$X_8$ is F, Y, V, L, C, or S;
$X_9$ is K, R or S; and
each of $X_{10}$ and $X_{11}$ is independently any amino acid.

In some embodiments, the sequence of 11 contiguous amino acids is not, or does not comprise, amino acid sequence AQTLAVPFKAQ (SEQ ID NO: 1). In some embodiments, the capsid protein does not comprise, amino acid sequence AQTLAVPFKAQ (SEQ ID NO: 1). As described herein, $X_{10}$ and $X_{11}$ can independently be any amino acids, for example any of the standard amino acids. In some embodiments, $X_{10}$ is A or N. In some embodiments, $X_{11}$ is Q or P. In some embodiments, $X_1$ is D. In some embodiments, $X_2$ is G. In some embodiments, $X_3$ is T. In some embodiments, $X_4$ is L. In some embodiments, $X_6$ is V or T. In some embodiments, $X_8$ is F. In some embodiments, amino acids $X_4X_5X_6X_7X_8X_9X_{10}X_{11}$ are LAVPFKAQ (SEQ ID NO: 80). In some embodiments, the amino acid sequence $X_1X_2X_3$ is DGT, GGT, EGT, DST, EST, QGT, NQT, SGS, SGN, ATT, AVT, or ART. In some embodiments, $X_1$ is A, $X_2$ is Q, and the amino acid sequence $X_6X_7X_8X_9X_{10}X_{11}$ is VPFKAQ. In some embodiments, $X_3$ is T and $X_4$ is L. In some embodiments, $X_5$ is A. In some embodiments, $X_1$ is A, $X_2$ is Q, $X_3$ is T, $X_4$ is L, and the amino acid sequence $X_8X_9X_{10}X_{11}$ is FKAQ. In some embodiments, the amino acid sequence $X_5X_6X_7$ is AVP, ATP, AQP, QQP, PQP, SNP, STP, SQP, QLP, TMP, or TTP. In some embodiments, the amino acid sequence $X_1X_2X_3X_4X_5X_6$ is AQTLAV (SEQ ID NO: 83), $X_{10}$ is A, and $X_{11}$ is Q. In some embodiments, the amino acid sequence $X_7X_8X_9$ is PFK. In some embodiments, the amino acid sequence $X_1X_2X_3X_4X_5X_6X_7X_8$ is AQTLAVPF (SEQ ID NO: 84). In some embodiments, the amino acid sequence $X_9X_{10}X_{11}$ is KAQ, KAP, or SNP. In some embodiments, the sequence of 11 contiguous amino acids $X_1X_2X_3X_4X_5X_6X_7X_8X_9X_{10}X_{11}$ is DGTLATPFKXX (X can be any amino acid, SEQ ID NO: 68). In some embodiments, the sequence of 11 contiguous amino acids $X_1X_2X_3X_4X_5X_6X_7X_8X_9X_{10}X_{11}$ is GGTLATPFKAQ (SEQ ID NO: 10). Various combinations of the embodiments described herein are encompassed in the scope of the present disclosure. For example, when $X_{10}$ is A, $X_{11}$ can be Q or P; and when $X_1$ is D, $X_2$ can be any one of G, N, S, T, and V. As another example, when $X_3$ is T and $X_4$ is L, $X_5$ can be A.

In some embodiments, $X_4$, $X_5$, $X_6$, $X_7$, $X_8$, $X_9$, $X_{10}$, and $X_{11}$ are L, A, V, P, F, K, A, and Q, respectively; and $X_3$ is T, S, or N. In some embodiments, it is advantageous for $X_3$ to be T. In some embodiments, the amino acid sequence $X_1X_2X_3$ is AQT, DGT, GGT, EGT, DST, EST, QGT, NQT, SGS, SGN, ATT, AVT, or ART.

In some embodiments, $X_1$ is A and $X_2$ is Q; $X_6$, $X_7$, $X_8$, $X_9$, $X_{10}$, and $X_{11}$ are V, P, F, K, A, Q, respectively; and $X_3$ is T and $X_4$ is L. In some embodiments, the amino acid sequence $X_3X_4X_5$ is TLA.

In some embodiments, $X_1$ is A, $X_2$ is Q, $X_3$ is T, $X_4$ is L, $X_8$ is F, $X_9$ is K, $X_{10}$ is A, and $X_{11}$ is Q, and the amino acid sequence $X_5X_6X_7$ is AVP, ATP, AQP, QQP, PQP, SNP, STP, SQP, QLP, TMP, or TTP.

In some embodiments, the sequence of 11 contiguous amino acids is AQTLAVPFKAQ (SEQ ID NO: 1).

$X_1$ is A, $X_2$ is Q, $X_3$ is T, $X_4$ is L, $X_5$ is A, $X_6$ is V, $X_7$ is P, and $X_8$ is F, and the amino acid sequence $X_9X_{10}X_{11}$ is KAQ, KAP, or SNP.

In some embodiments, the amino acid sequence is part of a capsid protein of the AAV vector. In some embodiments, the sequence of 11 contiguous amino acids is inserted between AA586 and 589 of an AAV capsid protein sequence SEQ ID NO: 45 of the vector. In some embodiments, the sequence of 11 continuous amino acids further comprises at least two of amino acids 587, 588, 589, or 590 of SEQ ID NO: 45. In some embodiments, the sequence of 11 contiguous amino acids is one of SEQ ID NOs: 1-36. In some embodiments, the AAV vector comprises at least 4 contiguous amino acids of one of SEQ ID NO: 1-44, 48-53 and 65-68.

As described herein, the rAAVs can be identified from libraries of capsids comprised of variants made by inserting 7 amino acids (AA) of randomized sequence between AA588 and AA589 of an AAV capsid protein. The AAV capsid protein can, in some embodiments, has various substitutions as compared to the wildtype AAV capsid protein, including but not limited to, K449R substitution, A587D substitution, Q588G substitution, A587G substitution, Q588G substitution, V592T substitution, K595S substitution, A595N substitution, Q597P substitution, and any combination thereof. In some embodiments, the AAV capsid protein has a sequence identical to the wildtype AAV9 capsid but with a K449R substitution. In some embodiments, the AAV9 capsid protein comprises the amino acid substitutions A587D and Q588G. In some embodiments, the AAV9 capsid protein comprises the amino acid substitutions A587G and Q588G. In some embodiments, the AAV9 capsid protein comprises the amino acid substitution V592T. In some embodiments the AAV9 capsid protein comprises the amino acid substitutions K595S, A595N, and Q597P.

In some embodiments, one or more targeting ptptides can be employed in a single system (e.g., in a single AAV vector, a single AAV capsid protein, or a single rAAV). For example one can employ one or more targeting sequences and also modify other sites to reduce the recognition of the AAVs by the pre-existing antibodies present in a subject, such as a human. In some embodiments, the AAV vector can include a capsid, which influences the tropism/targeting, speed of expression and possible immune response. The vector can also include the rAAV, which genome carries the transgene/therapeutic aspects (e.g., sequences) along with regulatory sequences. In some embodiments, the vector can include the targeting sequence within/on a substrate that is or transports the desired molecule (therapeutic molecule, diagnostic molecule, etc.).

The targeting peptides disclosed herein, in some embodiments, can increase transduction efficiency of rAAV to a target environment (e.g., the CNS, the PNS, the heart, or a combination thereof) in the subject as compared to an AAV that does not contain the targeting peptides. For example, the inclusion of one or more of the targeting peptides disclosed herein in a rAAV can result in an increase in transduction efficiency by, or by at least, 10%, 20%, 30%, 40%, 50%, 60%, 70%, 80%, 90%, 100%, 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 10-fold, 20-fold, 30-fold, 40-fold, 50-fold, 60-fold, 70-fold, 80-fold, 90-fold, 100-fold, or a range between any two of these values, as compared to an AAV that does not comprise the targeting peptide. In some embodiments, the increase is at least 2-fold. In some embodiments, the increase is a 40-90 fold increase. In some embodiments, the transduction efficiency is increases for transducing rAAV to the CNS. In some embodiments, the transduction efficiency is increases for transducing rAAV to the PNS. In some embodiments, the transduction efficiency is increases for transducing rAAV to the heart. In some embodiments, the transduction efficiency is increases for transducing rAAV to cardiomyocytes, sensory neurons, dorsal root ganglia, visceral organs, or any combination thereof.

In some embodiments, a capsid library is provided that comprises AAV genomes that contain both the full rep and cap sequence that have been modified so as to not prevent the replication of the virus under conditions in which it could normally replicate (co-infection of a mammalian cell along with a helper virus such as adenovirus). A pseudo wildtype ("wt") genome can be one that has an engineered cap gene within a "wt" AAV genome.

In some embodiments, the capsid library is made within a "pseudo-wild type" AAV genome containing the viral replication gene (rep) and capsid gene (cap) flanked by inverted terminal repeats (ITRs). In some embodiments, the capsid library is not made within a "pseudo-wild type" AAV genome containing the viral replication gene (rep) and capsid gene (cap) flanked by inverted terminal repeats (ITRs).

In some embodiments, the rAAV genome contains the cap gene and only those sequences within the rep gene required for the expression and splicing of the cap gene products. In some embodiments, a capsid gene recombinase recognition sequence is provided with inverted terminal repeats flanking these sequences.

In some embodiments, the system could be used to develop capsids that exhibit enhanced targeting of specific cells/organs, select for capsids that evade immunity, select for genomes that are more at homologous recombination, select for genome elements that increase the efficiency of conversion of the single stranded AAV genome to a double stranded DNA genome within a cell and/or select for genome elements that increase the conversion of AAV genome to a persistent, circularized form within the cell.

Uses of the AAV Vectors and RAAVs

The AAV vectors disclosed herein can be effectively transduced to a target environment (e.g., the CNS, the PNS, the heart, any combination thereof, and other desired system(s)) of a subject, for example, for delivering nucleic acids. In some embodiments, a method of delivering a nucleic acid sequence to the nervous system is provided. The method can include providing a protein comprising any one or more of the targeting sequences provided herein. The protein can be part of a capsid of an AAV. The AAV can comprise a nucleic acid sequence to be delivered to a nervous system. One can then administer the AAV to the subject.

In some embodiments, the nucleic acid sequence to be delivered to a target environment (e.g, nervous system) comprises one or more sequences that would be of some use or benefit to the nervous system and/or the local of delivery or surrounding tissue or environment. In some embodiments, it can be a nucleic acid that encodes a protein of interest, including but not limited to a trophic factor, a growth factor, or other soluble factors that might be released from the transduced cells and affect the survival or function of that cell and/or surrounding cells. In some embodiments, it can be a cDNA that restores protein function to humans or animals harboring a genetic mutation(s) in that gene. In some embodiments, it can be a cDNA that encodes a protein that can be used to control or alter the activity or state of a cell. In some embodiments, it can be a cDNA that encodes a protein or a nucleic acid used for assessing the state of a cell. In some embodiments, it can be a cDNA and/or associated RNA for performing genomic engineering. In some embodiments, it can be a sequence for genome editing via homologous recombination. In some embodiments, it can be a DNA sequence encoding a therapeutic RNA. In some embodiments, it can be a shRNA or an artificial miRNA delivery system. In some embodiments, it can be a DNA sequence that influences the splicing of an endogenous gene.

As used herein, a "protein of interest" can be any protein, including naturally-occurring and non-naturally occurring proteins. In some embodiments, a polynucleotide encoding one or more proteins of interest can be present in one of the AAV vectors disclosed herein, wherein the polynucleotide is operably linked with a promoter. In some instances, the promoter can drive the expression of the protein(s) of interest in a host cell (e.g., a human neuron). In some embodiments, the protein of interest is an anti-tau antibody, an anti-AB antibody, an ApoE isoform.

Examples of protein of interest include, but are not limited to, luciferases; fluorescent proteins (e.g., GFP); growth hormones (GHs) and variants thereof; insulin-like growth factors (IGFs) and variants thereof; granulocyte colony-stimulating factors (G-CSFs) and variants thereof; erythropoietin (EPO) and variants thereof; insulin, such as proinsulin, preproinsulin, insulin, insulin analogs, and the like; antibodies and variants thereof, such as hybrid antibodies, chimeric antibodies, humanized antibodies, monoclonal antibodies; antigen binding fragments of an antibody (Fab fragments), single-chain variable fragments of an antibody (scFV fragments); dystrophin and variants thereof; clotting factors and variants thereof; cystic fibrosis transmembrane conductance regulator (CFTR) and variants thereof; and interferons and variants thereof.

In some embodiments, the protein of interest is a therapeutic protein or variant thereof. Non-limiting examples of therapeutic proteins include blood factors, such as β-globin, hemoglobin, tissue plasminogen activator, and coagulation factors; colony stimulating factors (CSF); interleukins, such as IL-1, IL-2, IL-3, IL-4, IL-5, IL-6, IL-7, IL-8, IL-9, etc.; growth factors, such as keratinocyte growth factor (KGF), stem cell factor (SCF), fibroblast growth factor (FGF, such as basic FGF and acidic FGF), hepatocyte growth factor (HGF), insulin-like growth factors (IGFs), bone morphogenetic protein (BMP), epidermal growth factor (EGF), growth differentiation factor-9 (GDF-9), hepatoma derived growth factor (HDGF), myostatin (GDF-8), nerve growth factor (NGF), neurotrophins, platelet-derived growth factor (PDGF), thrombopoietin (TPO), transforming growth factor alpha (TGF-α), transforming growth factor beta (TGF-β), and the like; soluble receptors, such as soluble TNF-α receptors, soluble VEGF receptors, soluble interleukin receptors (e.g., soluble IL-1 receptors and soluble type II IL-1 receptors), soluble γ/δ T cell receptors, ligand-binding fragments of a soluble receptor, and the like; enzymes, such as α-glucosidase, imiglucarase, β-glucocerebrosidase, and alglucerase; enzyme activators, such as tissue plasminogen activator; chemokines, such as IP-10, monokine induced by interferon-gamma (Mig), Groa/IL-8, RANTES, MIP-1α, MIP-1β, MCP-1, PF-4, and the like; angiogenic agents, such as vascular endothelial growth factors (VEGFs, e.g., VEGF121, VEGF165, VEGF-C, VEGF-2), transforming growth factor-beta, basic fibroblast growth factor, glioma-derived growth factor, angiogenin, angiogenin-2; and the like; anti-angiogenic agents, such as a soluble VEGF receptor; protein vaccine; neuroactive peptides, such as nerve growth factor (NGF), bradykinin, cholecystokinin, gastin, secretin, oxytocin, gonadotropin-releasing hormone, beta-endorphin, enkephalin, substance P, somatostatin, prolactin, galanin, growth hormone-releasing hormone, bombesin, dynorphin, warfarin, neurotensin, motilin, thyrotropin, neuropeptide Y, luteinizing hormone, calcitonin, insulin, glucagons, vasopressin, angiotensin II, thyrotropin-releasing hormone, vasoactive intestinal peptide, a sleep peptide, and the like; thrombolytic agents; atrial natriuretic peptide; relaxin; glial fibrillary acidic protein; follicle stimulating hormone (FSH); human alpha-1 antitry sin; leukemia inhibitory factor (LIF); transforming growth factors (TGFs); tissue factors, luteinizing hormone; macrophage activating factors; tumor necrosis factor (TNF); neutrophil chemotactic factor (NCF); nerve growth factor; tissue inhibitors of metalloproteinases; vasoactive intestinal peptide; angiogenin; angiotropin; fibrin; hirudin; IL-1 receptor antagonists; and the like. Some other non-limiting examples of protein of interest include ciliary neurotrophic factor (CNTF); brain-derived neurotrophic factor (BDNF); neurotrophins 3 and 4/5 (NT-3 and 4/5); glial cell derived neurotrophic factor (GDNF); aromatic amino acid decarboxylase (AADC); hemophilia related clotting proteins, such as Factor VIII, Factor IX, Factor X; dystrophin or nini-dystrophin; lysosomal acid lipase; phenylalanine hydroxylase (PAH); glycogen storage disease-related enzymes, such as glucose-6-phosphatase, acid maltase, glycogen debranching enzyme, muscle glycogen phosphorylase, liver glycogen phosphorylase, muscle phosphofructokinase, phosphorylase kinase (e.g., PHKA2), glucose transporter (e.g., GLUT2), aldolase A, β-enolase, and glycogen synthase; lysosomal enzymes (e.g., beta-N-acetylhexosaminidase A); and any variants thereof.

In some embodiments, the protein of interest is an active fragment of a protein, such as any of the aforementioned proteins. In some embodiments, the protein of interest is a fusion protein comprising some or all of two or more proteins. In some embodiments a fusion protein can comprise all or a portion of any of the aforementioned proteins.

In some embodiments, the viral vector comprises a polynucleotide comprising coding regions for two or more proteins of interest. The two or more proteins of interest can be the same or different from each other. In some embodiments, the two or more proteins of interest are related polypeptides, for example light chain(s) and heavy chain(s) of the same antibody.

In some embodiments, the protein of interest is a multi-subunit protein. For examples, the protein of interest can comprise two or more subunits, or two or more independent polypeptide chains. In some embodiments, the protein of interest can be an antibody. Examples of antibodies include, but are not limited to, antibodies of various isotypes (for example, IgG1, IgG2, IgG3, IgG4, IgA, IgD, IgE, and IgM); monoclonal antibodies produced by any means known to those skilled in the art, including an antigen-binding fragment of a monoclonal antibody; humanized antibodies; chimeric antibodies; single-chain antibodies; antibody fragments such as Fv, F(ab')2, Fab', Fab, Facb, scFv and the like; provided that the antibody is capable of binding to antigen. In some embodiments, the antibody is a full-length antibody. In some embodiments, the protein of interest is not an immunoadhesin.

In some embodiments, the resulting targeting molecules can be employed in methods and/or therapies relating to in vivo gene transfer applications to long-lived cell populations. In some embodiments, these can be applied to any rAAV-based gene therapy, including, for example: spinal muscular atrophy (SMA), amyotrophic lateral sclerosis (ALS), Parkinson's disease, Friedreich's ataxia, Pompe disease, Huntington's disease, Alzheimer's disease, Battens disease, lysosomal storage disorders, glioblastoma multiforme, Rett syndrome, Leber's congenital amaurosis, chronic pain, stroke, spinal cord injury, traumatic brain injury and lysosomal storage disorders. In addition, rAAVs can also be employed for in vivo delivery of transgenes for non-therapeutic scientific studies such as optogenetics, gene overexpression, gene knock-down with shRNA or miRNAs, modulation of endogenous miRNAs using miRNA sponges or decoys, recombinase delivery for conditional gene deletion, conditional (recombinase-dependent) expression, or gene editing with CRISPRs, TALENs, and zinc finger nucleases.

Provided herein are methods for treating and/or preventing Huntington's disease using the methods and compositions described herein. The method of treating and/or preventing Huntington's disease can include identifying the subject(s), providing a vector for delivery of a polynucleotide to the nervous system of the subject as provided herein, administering the vector in an effective dose to the subject thereby treating and/or preventing Huntington's disease in the subject. In some embodiments, the methods for treating a subject with Huntington's disease involve compositions where the vector delivers the polynucleotide composition comprising a Zinc finger protein (ZFP) engineered to represses the transcription of the Huntingtin (HTT) gene. In some embodiments, the ZFP selectively represses the transcription of the HTT gene allele responsible for causing the Huntington's disease in the subject by binding to the CAG repeat region of the HTT gene in a CAG repeat length-dependent manner. In some embodiments, the ZNFTR selectively represses transcription of both alleles of the HTT gene.

In some embodiments, the therapeutic item to be administered to the subject comprises a short hairpin RNA (shRNA) or microRNA (miRNA) that knocks down Huntingtin expression by inducing the selective degradation of, or inhibiting translation from, RNA molecules transcribed from the disease causing HTT allele by binding to the CAG repeat. In some embodiments a method to treat patients with Huntington's Disease comprises incorporating Huntingtin-specific micro RNA expression cassette within an rAVV genome. This could then be packaged into one of the sequence variants disclosed for delivery through the vasculature.

In some embodiments, the therapeutic item to be administered to the subject comprises a short hairpin RNA (shRNA) or microRNA (miRNA) that knocks down Huntingtin expression by inducing the degradation of, or inhibiting translation from, RNA molecules transcribed from one or both alleles of the HTT gene. In some embodiments, the therapeutic item to be administered to the subject comprises a short hairpin RNA (shRNA) or microRNA (miRNA) that knocks down Huntingtin expression by inducing the selective degradation of, or inhibiting translation from, RNA molecules transcribed from the disease causing HTT allele through the selective recognition of one or more nucleotide polymorphisms present within the disease causing allele. The nucleotide polymorphisms can be used by one skilled in the art to differentiate between the normal and disease causing allele.

In some embodiments, the therapeutic item to be administered to the subject comprises a polynucleotide that encodes an RNA or protein that alters the splicing or production of the HTT RNA. In some embodiments, the therapeutic item to be administered to the subject comprises a polynucleotide that encodes one or more polypeptides and/or RNAs for genome editing using a Transcription activator-like effector nuclease (TALEN), zinc finger nuclease or clustered regularly interspaced short palindromic repeats—cas9 gene (CRISPR/Cap9) system engineered by one skilled in the art to induce a DNA nick or double-stranded DNA break within or adjacent to the HTT gene to cause an alteration in the HTT gene sequence. In some embodiments, the therapeutic item to be administered to the subject comprises a polynucleotide encoding a polypeptide that binds to a polypeptide from the HTT gene, alters the conformation of a polypeptide from the HTT gene or alters the assembly of a polypeptide from the HTT gene into aggregates or alters the half-life of a polypeptide from the HTT gene. In some embodiments, the therapeutic item to be administered to the subject comprises a polynucleotide that encodes a RNA or polypeptide that causes or prevents a post-transcriptional modification of a polypeptide from the HTT gene. In some embodiments, the therapeutic item to be administered to the subject comprises a polynucleotide that encodes a polypeptide from a chaperone protein known to those skilled in the art to influence the conformation and/or stability of a polypeptide from the HTT gene.

In some embodiments, the therapeutic item to be administered to the subject comprises regulatory elements known to one skilled in the art to influence the expression of the RNA and/or protein products encoded by the polynucleotide within desired cells of the subject.

In some embodiments, the therapeutic item to be administered to the subject comprises a therapeutic item applicable for any disease or disorder of choice. In some embodiments, this can include compositions for treating and/or preventing Alzheimers disease using the methods and compositions described herein, for example, ApoE2 or ApoE3 for Alzheimer's disease; SMN for the treatment of SMA; frataxin delivery for the treatment of Friedreich's ataxia; and/or shRNA or miRNA for the treatment of ALS.

In some embodiments the variants herein can be used as an effective means of gene transfer to cardiac muscle. Doing so may be useful in studying and treating many different diseases and injuries including Friedreich's ataxia, heart failure, ischemic heart disease, cardiac hypertrophy, chronic pain, and peripheral nerve injury. In some embodiments the variants herein can be used to transduce peripheral nerves when administered through the vasculature.

In some embodiments, the therapeutic item for delivery is a protein (encodes a protein) or RNA based strategy for reducing synuclein aggregation for the treatment of Parkinson's. For example delivering a polynucleotide that encodes a synuclein variant that is resistant to aggregation and thus disrupts the aggregation of the endogenous synuclein.

In some embodiments, a transgene encoding a trophic factor for the treatment of AD, PD, ALS, SMA, or HD can be the therapeutic item involved. In some embodiments, a trophic factor can be employed and can include, for example, BDNF, GDNF, NGF, LW, and/or CNTF.

Dosages of a viral vector can depend primarily on factors such as the condition being treated, the age, weight and health of the patient, and may thus vary among patients. For example, a therapeutically effective human dosage of the viral vector is generally in the range of from about 0.1 ml to about 100 ml of solution containing concentrations of from about $1 \times 10^9$ to $1 \times 10^{16}$ genomes virus vector. A preferred human dosage can be about $1 \times 10^{13}$ to $1 \times 10^{16}$ AAV genomes. The dosage will be adjusted to balance the therapeutic benefit against any side effects and such dosages may vary depending upon the therapeutic application for which the recombinant vector is employed. The levels of expression of the transgene can be monitored to determine the frequency of dosage resulting from the vector.

In some embodiments, the vector can also comprise regulatory control elements known to one of skill in the art to influence the expression of the RNA and/or protein products encoded by the polynucleotide within desired cells of the subject.

In some embodiments, functionally, expression of the polynucleotide is at least in part controllable by the operably linked regulatory elements such that the element(s) modulates transcription of the polynucleotide, transport, processing and stability of the RNA encoded by the polynucleotide and, as appropriate, translation of the transcript. A specific example of an expression control element is a promoter, which is usually located 5' of the transcribed sequence. Another example of an expression control element is an enhancer, which can be located 5' or 3' of the transcribed sequence, or within the transcribed sequence. Another example of a regulatory element is a recognition sequence for a microRNA. Another example of a regulatory element is an intron and the splice donor and splice acceptor sequences that regulate the splicing of said intron. Another example of a regulatory element is a transcription termination signal and/or a polyadenylation sequences.

Expression control elements and promoters include those active in a particular tissue or cell type, referred to herein as a "tissue-specific expression control elements/promoters." Tissue-specific expression control elements are typically active in specific cell or tissue (for example in the liver, brain, central nervous system, spinal cord, eye, retina or lung). Expression control elements are typically active in these cells, tissues or organs because they are recognized by transcriptional activator proteins, or other regulators of transcription, that are unique to a specific cell, tissue or organ type.

Expression control elements also include ubiquitous or promiscuous promoters/enhancers which are capable of driving expression of a polynucleotide in many different cell types. Such elements include, but are not limited to the cytomegalovirus (CMV) immediate early promoter/enhancer sequences, the Rous sarcoma virus (RSV) promoter/enhancer sequences and the other viral promoters/enhancers active in a variety of mammalian cell types; promoter/enhancer sequences from ubiquitously or promiscuously expressed mammalian genes including, but not limited to, beta actin, ubiquitin or EF1alpha; or synthetic elements that are not present in nature.

Expression control elements also can confer expression in a manner that is regulatable, that is, a signal or stimuli increases or decreases expression of the operably linked polynucleotide. A regulatable element that increases expression of the operably linked polynucleotide in response to a signal or stimuli is also referred to as an "inducible element" (that is, it is induced by a signal). Particular examples include, but are not limited to, a hormone (for example, steroid) inducible promoter. A regulatable element that decreases expression of the operably linked polynucleotide in response to a signal or stimuli is referred to as a "repressible element" (that is, the signal decreases expression such that when the signal, is removed or absent, expression is increased). Typically, the amount of increase or decrease conferred by such elements is proportional to the amount of signal or stimuli present; the greater the amount of signal or stimuli, the greater the increase or decrease in expression.

In some embodiments, the rAAV having a capsid protein comprising one or more targeting peptides disclosed herein can be used to effectively transduce nervous systems. This makes the rAAV useful for delivery of therapeutics to treat, for example Huntington's disease (HD), Alzheimer's disease, Parkinson's disease, Amyotrophic lateral sclerosis, spinal muscular atrophy, types I and II, Friedreich's Ataxia, Spinocerebellar ataxia and any of the lysosomal storage disorders that involve cells with CNS, which includes but is not limited to Krabbe disease, Sandhoff disease, Tay-Sachs, Gaucher disease (Type I, II, or III Niemann-Pick disease (NPC1 or NPC2 deficiency), Hurler syndrome, Pompe disease, and/or Batten disease.

In some embodiments, the rAAV having a capsid protein comprising one or more targeting peptides disclosed herein can be used to effectively transduce cardiac muscles, peripheral nerves, or any combination thereof. This makes the rAAV useful for delivery of therapeutics to treat, for example Friedreich's ataxia, heart failure, ischemic heart disease, cardiac hypertrophy, chronic pain, and/or peripheral nerve injury.

In some embodiments, the rAAV having a capsid protein comprising one or more targeting peptides disclosed herein can be used to deliver genes to specific cell types in the target environment of a subject. For example, the rAAV can be used for delivering genes to neurons and glia in the nervous system (including PNS, CNS, or both) of a subject (e.g., a mammal). The targeting peptide can be, for example, AAV-PHP.N (SEQ ID NO: 46). The compositions and methods disclosed herien can be used in, for example, (i) reducing the expression of mutant Huntingtin in patients with Huntington's Disease by, for example, incorporatin a Huntingtin-specific microRNA expression cassette within a rAAV genome and packaging the rAAV genome into a variant rAAV (e.g., AAV-PHP.N) for delivery through, for example the vasculature, (ii) delivering a functional copy of the Frataxin gene to patients with Friedreich's ataxia, (iii) restoring expression of an enzyme critical for normal lysosomal function in patients lacking expression of the enzyme due to genetic mutation (e.g., patients with Neimann-Pick disease, mucopolysaccharidosis III, and/or Gaucher's disease), (iv) using the rAAV (e.g., AAV-PHP.N) to generate animal models of disease, or a combination thereof.

Pharmaceutical Compositions and Methods of Administration

Also disclosed herein are pharmaceutical compositions comprising one or more of the rAAV viruses disclosed herein and one or more pharmaceutically acceptable carriers. The compositions can also comprise additional ingredients such as diluents, stabilizers, excipients, and adjuvants. As used herein, "pharmaceutically acceptable" carriers, excipients, diluents, adjuvants, or stabilizers are the ones nontoxic to the cell or subject being exposed thereto (preferably inert) at the dosages and concentrations employed or that have an acceptable level of toxicity as determined by the skilled practitioners.

The carriers, diluents and adjuvants can include buffers such as phosphate, citrate, or other organic acids; antioxidants such as ascorbic acid; low molecular weight polypeptides (e.g., less than about 10 residues); proteins such as serum albumin, gelatin or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween™, Pluronics™ or polyethylene glycol (PEG). In some embodiments, the physiologically acceptable carrier is an aqueous pH buffered solution.

Titers of the rAAV to be administered will vary depending, for example, on the particular rAAV, the mode of administration, the treatment goal, the individual, and the cell type(s) being targeted, and can be determined by methods standard in the art.

As will be readily apparent to one skilled in the art, the useful in vivo dosage of the recombinant virus to be administered and the particular mode of administration will vary depending upon the age, weight, the severity of the affliction, and animal species treated, the particular recombinant virus expressing the protein of interest that is used, and the specific use for which the recombinant virus is employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

Although the exact dosage will be determined on a drug-by-drug basis, in most cases, some generalizations regarding the dosage can be made. In some embodiments, the rAAV for delivery a nucleic acid to the nervous system (e.g., CNS) of a subject can be administered, for example via injection, to a subject at a dose of between $1\times10^{10}$ genome copies (GC) of the recombinant virus per kg of the subject and $2\times10^{14}$ GC per kg, for example between $5\times10^{11}$ GC/kg and $5\times10^{12}$ GC/kg. In some embodiments, the dose of the rAAV administered to the subject is no more than $2\times10^{14}$ GC per kg. In some embodiments, the dose of the rAAV administered to the subject is no more than $5\times10^{12}$ GC per kg. In some embodiments, the dose of the rAAV administered to the subject is no more than $5\times10^{11}$ GC per kg.

The recombinant viruses disclosed herein can be administered to a subject (e.g., a human) in need thereof. The route of the administration is not particularly limited. For example, a therapeutically effective amount of the recombinant viruses can be administered to the subject by via routes standard in the art. Non-limiting examples of the route include intramuscular, intravaginal, intravenous, intraperitoneal, subcutaneous, epicutaneous, intradermal, rectal, intraocular, pulmonary, intracranial, intraosseous, oral, buccal, systematic, or nasal. In some embodiments, the recombinant virus is administered to the subject by systematic transduction. In some embodiments, the recombinant virus is administered to the subject by intramuscular injection. In some embodiments, the recombinant virus is administered to the subject by intravaginal injection. In some embodiments, the rAAV is administered to the subject by the parenteral route (e.g., by intravenous, intramuscular or subcutaneous injection), by surface scarification or by inoculation into a body cavity of the subject. Route(s) of administration and serotype(s) of AAV components of the rAAV virus can be readily determined by one skilled in the art taking into account the infection and/or disease state being treated and the target cells/tissue(s) that are to express the protein of interest. In some embodiments, it can be advantageous to administer the rAAV via intravenous administration.

Actual administration of the rAAV can be accomplished by using any physical method that will transport the rAAV into the target tissue of the subject. For example, the rAAV can be administered intravenously. As disclosed herein, capsid proteins of the rAAV can be modified so that the rAAV is targeted to a particular target environment of interest such as central nervous system, and to enhance tropism to the target environment of interest (e.g, CNS tropism). In some embodiments, the rAAV delivers a nucleic acid to the heart, peripheral nerves, or a combination thereof. Pharmaceutical compositions can be prepared, for example, as injectable formulations.

The recombinant virus to be used can be utilized in liquid or freeze-dried form (in combination with one or more suitable preservatives and/or protective agents to protect the virus during the freeze-drying process). For gene therapy (e.g., of neurological disorders which may be ameliorated by a specific gene product) a therapeutically effective dose of the recombinant virus expressing the therapeutic protein is administered to a host in need of such treatment. The use of the recombinant virus disclosed herein in the manufacture of a medicament for inducing immunity in, or providing gene therapy to, a host is within the scope of the present application.

In instances where human dosages for the rAAV have been established for at least some condition, those same dosages, or dosages that are between about 0.1% and 500%, more preferably between about 25% and 250% of the established human dosage can be used. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

A therapeutically effective amount of the rAAV can be administered to a subject at various points of time. For example, the rAAV can be administered to the subject prior to, during, or after the subject has developed a disease or disorder. The rAAV can also be administered to the subject prior to, during, or after the occurrence of a disease or disorder (e.g., Huntington's disease (HD), Alzheimter's disease, Parkinson's disease, Amyotrophic lateral sclerosis, spinal muscular atrophy, types I and II, Friedreich's Ataxia, Spinocerebellar ataxia and any of the lysosomal storage disorders that involve cells with CNS, which includes but is not limited to Krabbe disease, Sandhoff disease, Tay-Sachs, Gaucher disease (Type I, II, or III), Niemann-Pick disease (NPC1 or NPC2 deficiency), Hurler syndrome, Pompe disease, Batten disease, or any combination thereof), chronic pain, cardiac failture, cardac arrhythmias, or a combination thereof. In some embodiments, the rAAV is administered to the subject during remission of the disease or disorder. In some embodiments, the rAAV is administered prior to the onset of the disease or disorder in the subject. In some embodiments, the rAAV is administered to a subject at a risk of developing the disease or disorder.

The dosing frequency of the rAAV virus can vary. For example, the rAAV virus can be administered to the subject about once every week, about once every two weeks, about once every month, about one every six months, about once every year, about once every two years, about once every three years, about once every four years, about once every five years, about once every six years, about once every seven years, about once every eight years, about once every nine years, about once every ten years, or about once every fifteen years. In some embodiments, the rAAV virus is administered to the subject at most about once every week, at most about once every two weeks, at most about once every month, at most about one every six months, at most about once every year, at most about once every two years, at most about once every three years, at most about once every four years, at most about once every five years, at most about once every six years, at most about once every seven years, at most about once every eight years, at most about once every nine years, at most about once every ten years, or at most about once every fifteen years.

EXAMPLES

Some aspects of the embodiments discussed above are disclosed in further detail in the following examples, which are not in any way intended to limit the scope of the present disclosure.

Example 1

Evolving AAV-PHP.B to Create Variants

To evolve variants of AAV-PHP.B that provide greater CNS transduction and more selective transduction of neurons, the AAV-PHP.B 7-mer sequence (SEQ ID NO: 40) described in U.S. Patent Publication No. 2015/0079038 (the content of which is incorporated herein by reference in its entirety) was partially randomized through overlapping replacement of 3 amino acids of the 7-mer sequence and the 2 amino acids flanking the 7-mer with random amino acids. An overview of this strategy for evolving AAV-PHP.B is shown in FIG. 1 (X presents any one of the 20 standard amino acids).

AAV-PHP.N

After two rounds of selection, numerous variants were found to be enriched in the sequences recovered from one or more of the Cre lines. One of those sequences, AAV-PHP.N (DGTLAVPFKAQ (SEQ ID NO: 4)) was chosen for characterization as an individual variant.

The DGTLAVPFKAQ sequence represented 8.1% of the total sequences recovered from Vgat-IRES-Cre mice, 4.4% of the sequences recovered from the Vglut2-IRES-Cre mice, 0% of the sequences recovered from GFAP-Cre mice and 0% of sequences recovered from the liver (non-cre dependent recovery). Based on these data, it was believed that DGTLAVPFKAQ (SEQ ID NO: 4) would be selectively more efficient at transducing neurons over astrocytes. The DGTLAVPFKAQ (SEQ ID NO: 4) amino acid sequence was independently selected from 2 different nucleotide sequences: (i) GAT GGG ACT TTG GCG GTG CCT TTT AAG GCA CAG (SEQ ID NO: 54), (ii) GAT GGG ACG TTG GCG GTG CCT TTT AAG GCA CAG (SEQ ID NO: 55). Together sequences with the consensus D/E-S/G-TLAVPFK (SEQ ID NO: 40) accounted for 18.9% of the total sequences recovered from Vgat-IRES-Cre mice, 15.6% of the sequences recovered from the Vglut2-IRES-Cre mice, 8.3% of the sequences recovered from GFAP-Cre mice, and 0% of sequences recovered from the liver (non-cre dependent recovery) after two rounds of selection.

Figure 2:
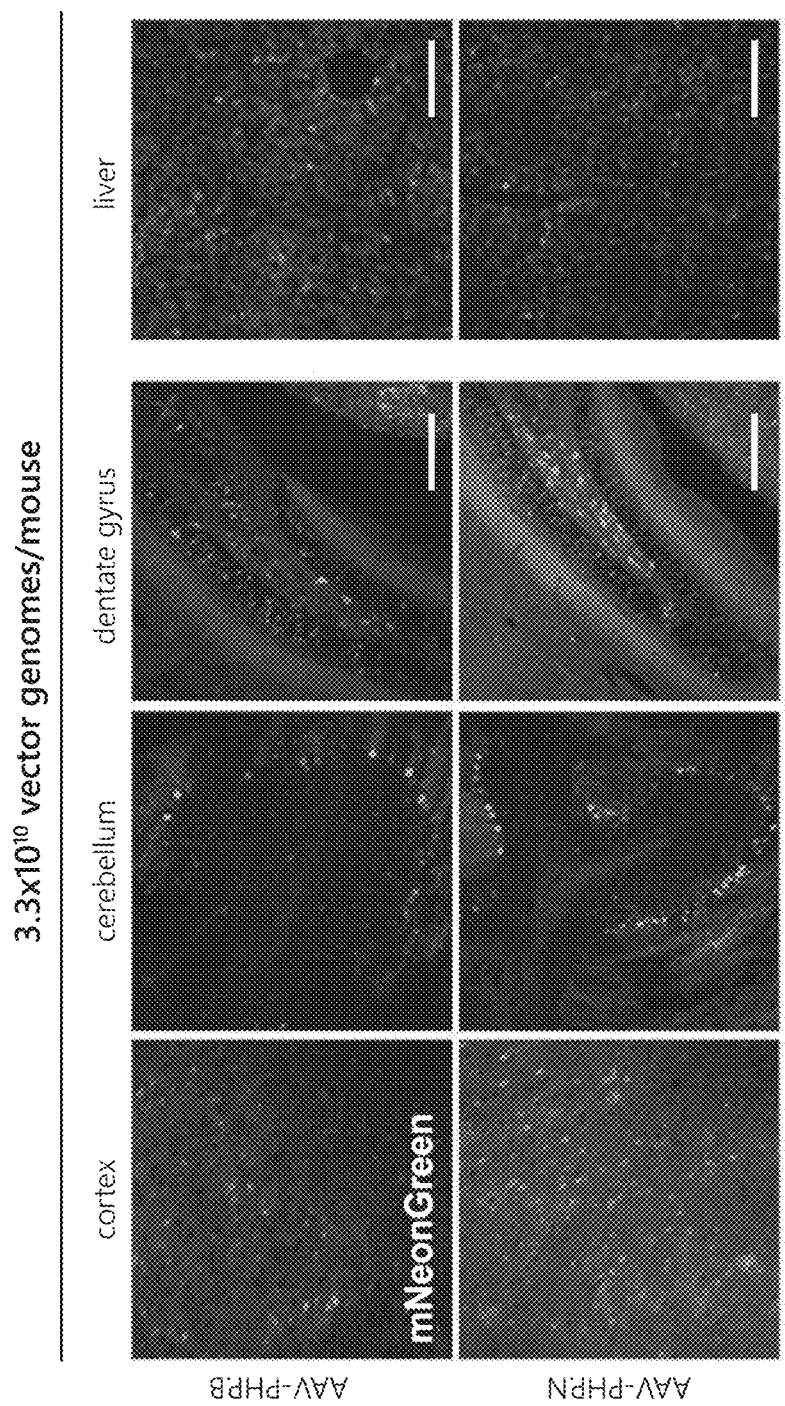
FIG. 2 depicts AAV-PHP.N transducing CNS neurons more efficiently than AAV-PHP.B. Images were taken 2 weeks after intravenous injection of a low dose ($3.3 \times 10^{10}$ vg/mouse) of AAV-CAG-mNeonGreen packaged into AAV-PHP.B (top) or AAV-PHP.N (bottom). Bright spots indicate expression of mNeonGreen protein (and thus transduction of AAV). Images show higher AAV-PHP.N expression in the cortex, cerebellum, and gentate gyrus compared to AAV-PHP.B expression. Thus, compared with AAV-PHP.B, AAV-PHP.N provides greater transduction of cells with the morphology of neurons in several brain regions. Scale bars are 200 µm.

Data for AAV-PHP.N (DGTLAVPFKAQ (SEQ ID NO: 4)) is presented in FIG. 2. The identification of the capsid comprising AAV-PHP.N sequence (SEQ ID NO: 46) was possible through the use of the CREATE method disclosed herein to perform simultaneous selections in multiple Cre transgenic mouse lines. Taken together, the findings that (i) the AAV-PHP.N sequence (SEQ ID NO: 46) was selectively recovered from CNS neurons but not from CNS astrocytes or the liver and that (ii) the AAV-PHP.N capsid provides selectively enhanced transduction of neurons but not glia and liver (as compared with AAV-PHP.B) demonstrates the usefulness of performing in vivo selections in multiple cell types to engineer novel vectors with more desirable transduction characteristics.

AAV-PHP.S

The AAV-PHP.S variant (SEQ ID NO: 47) was discovered by selecting for AAV capsids that more efficiently target GFAP-Cre expressing cells. The variant was identified from a library in which 7AA (7-mer) of randomized sequence was inserted between the amino acids 588-589 of the capsid protein (VP1 numbering). The AAV-PHP.S has the 7-mer sequence of QAVRTSL (SEQ ID NO: 37) which is encoded by the nucleic acid sequence of CAG GCG GTT AGG ACG TCT TTG (SEQ ID NO: 56).

AAV9 is a leading candidate vector for gene transfer to the cardiac muscle and also provides transduction of peripheral nerves when administered through the vasculature. Data shown in FIGS. 3A-3D demonstrate that systemically delivered AAV-PHP.S (SEQ ID NO: 47) provides markedly more expression in the heart and sensory nerves than AAV9 (SEQ ID NO: 45) comprising no AAV-PHP.S targeting peptide.

Example 2

Recovering Novel AAV Capsid Sequences Using Cre-Recombination-Based AAV Targeted Evolution (CREATE)

Directed evolution has been used to generate AAVs that evade neutralizing antibodies (Maheshri et al 2006) and better target glioma cells (McGuire et al. 2010), airway epithelium (Excoffon et al. 2009) and photoreceptors in the retina after intravitreal injection (Dalkara et al 2013). In addition, using a human/mouse chimeric liver model, Lisowski et al. developed a rAAV that specifically and efficiently targeted the human hepatocytes (2013). Some of the embodiments described herein provide methods for the enrichment and selective recovery of sequences with desirable traits from libraries of sequence variants using a recombination-dependent recovery strategy.

One approach that has been used to develop rAAVs with improved tissue/cell type targeting is to perform directed evolution on the AAV capsid gene. Typically this is done by making a library of replication competent AAVs that are modified to introduce random mutations into the AAV cap gene, which codes for the capsid proteins that determines the tissue tropism. The AAV capsid virus library is then injected in an animal or delivered to cells in culture. After a certain time, capsid sequences that are present in the cells/tissue of interest are recovered. These recovered sequences are then used to generate a new pool of viruses and then the process is repeated. Through repeated rounds of selection/sequence recovery, sequences that generate capsids that function better (i.e., those repeatedly pass the selection process) will be enriched. The capsids that exhibit an improved ability to transduce the target can then be recovered and assessed as individual clones or mutated further and subjected to additional rounds of selection.

This example describes the methods and materials used in a selection strategy called Cre-recombination-based AAV targeted evolution (CREATE) which enables the development of AAV capsids that more efficiently transduce defined Cre-expressing cell populations in vivo. As described herein, CREATE was used to generate AAV variants that efficiently and widely transduce the adult mouse central nervous system (CNS) after intravenous injection. Variants generated using this method can transfer genes throughout the CNS with an efficiency that is sometimes 40-fold greater than that of the current standard, AAV914-17, and transduces the majority of astrocytes and neurons across multiple CNS regions. In in vitro applications, the variants can transduce human neurons and astrocytes more efficiently than does AAV9, demonstrating the potential of CREATE to produce customized AAV vectors for biomedical applications.

Experimental Materials and Methods

Method of Modifying the RAAV-Cap-In-Cis-Lox Genome Plasmid

The rAAV-Cap-in-cis-lox genome plasmid contains three main elements flanked by AAV2 ITRs: (i) an mCherry expression cassette, which is comprised of a 398 bp fragment of the human UBC gene upstream of the mCherry cDNA followed by a synthetic polyadenylation sequence40; (ii) the AAV9 capsid gene and regulatory sequences, which are comprised of the AAV5 p41 promoter sequence (1680-1974 of GenBank AF085716.1) and splicing sequences taken from the AAV2 rep gene; and (iii) a Cre-dependent switch, which is comprised of the SV40 polyadenylation sequence (pA) flanked by inverted lox71 and lox66 sites. The rAAV-Cap-in-cis-lox genome plasmid was further modified to introduce two unique restriction sites, XbaI and AgeI, within the capsid sequence. These sites flank the region (AA450-592) that is replaced by the randomized library fragment. The introduction of the XbaI site introduces a K449R mutation, which does not have an overt effect on vector production or transduction. The mutations required to insert the AgeI site are silent. For the rAAV-ΔCap-in-cis acceptor plasmid used for the capsid library cloning, the coding region between the XbaI and AgeI sites was removed to prevent virus production from the acceptor plasmid lacking the library fragment.

As a template for the library fragment, the region spanning the XbaI and AgeI sites of the modified AAV9 was PCR amplified. This sequence was modified to remove a unique EarI restriction site and insert a unique KpnI site (both silent mutations) to create the xE fragment. The modified xE fragment was TA cloned into pCRII (Life Technologies) to generate pCRII-9Cap-xE Eliminating the EarI site provided a second method that could be used, if necessary, to selectively digest contaminating (AAV9) capsid sequences recovered by PCR, but not digest the library-derived sequences. Using the rAAV-ΔCap-in-cis acceptor for cloning the libraries and taking standard PCR precautions (e.g., UV treating reagents and pipettors) was sufficient to prevent contamination.

The AAV2/9 REP-AAP helper plasmid was constructed by introducing five stop codons into the coding sequence of the VP reading frame of the AAV9 gene at VP1 AAs: 6, 10, 142, 148 and 216. The stop codon at AA216 was designed not to disrupt the coding sequence of the AAP protein, which is encoded within an alternative reading frame.

Several rAAV genomes were used in this study. Each is constructed within a single stranded (ss) rAAV genome with a reporter driven by the ubiquitous CMV-β-Actin-intron-β-Globin hybrid promoter (CAG). For simplicity, the vector descriptions have been abbreviated in the text. ssAAV-CAG-GFP refers to ssAAV-CAG-eGFP-2A-Luc-WPRE-SV40 polyA. ssAAV-CAG-NLS-GFP refers to ssAAV-CAG-NLSGFP-WPRE-SV40 polyA, which was constructed by inserting the nuclear localization sequence PKKKRKV at both the N- and C-termini of GFP. ssAAV-CAG-mNeGreen-f refers to ssAAV-CAGmNeonGreen-f-WPRE with a human growth hormone polyA signal. The mNeonGreen was modified with the membrane targeting (farnesylation and palmitoylation signals) sequence from c-Ha-Ras.

Method of Capsid Library Generation

Figure 8A:
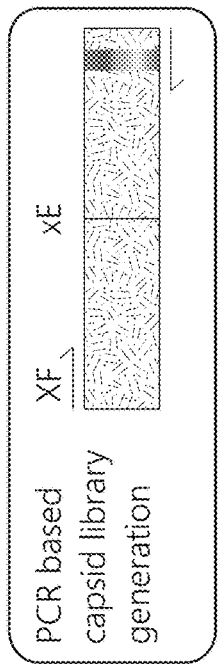
FIGS. 8A-8B show schematic illustrations of PCR products and the rAAV-Cap-in-cis genome.
Figure 8B:
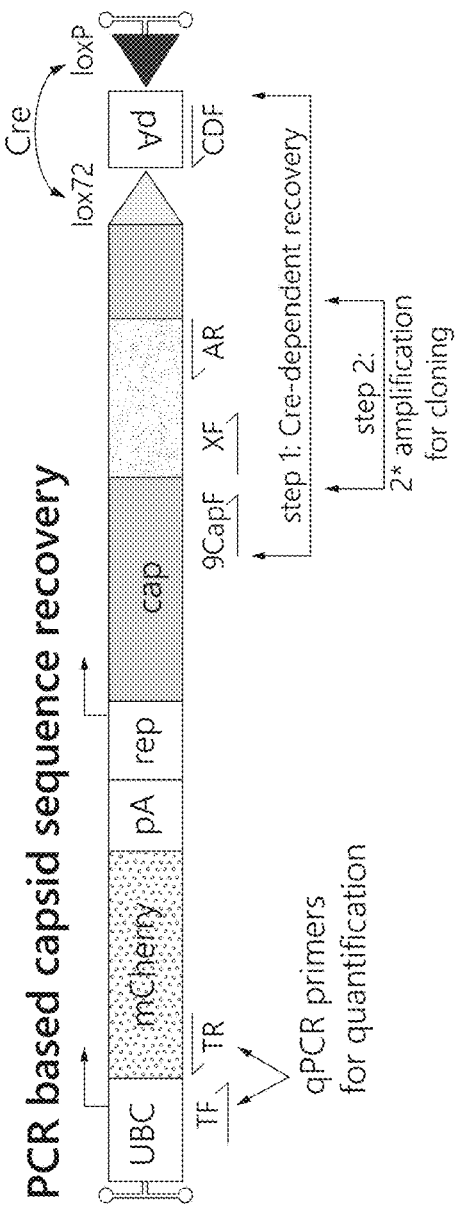

The random 7-mer library fragment (inserted between amino acids 588 and 589) was generated by PCR using Q5 Hot Start High-Fidelity DNA Polymerase (NEB; M0493), primers XF and 7xMNN and pCRII-9Cap-xE as a template. Schematics showing the approximate primer binding sites are shown in FIGS. 8A-8B and the primer sequences are provided in Table 1. To generate the rAAV-based library, the PCR products containing the library and the XbaI- and AgeI-digested rAAV-ΔCap-in-cis acceptor plasmid were assembled using Gibson Assembly (NEB; E2611). The reaction products were then treated with Plasmid Safe (PS) DNase (Epicentre; E3105K) to digest any unassembled fragments and purified using a QIAquick PCR Purification Kit (Qiagen). This reaction typically yielded over 100 ng of assembled plasmid (as defined by the amount of DNA remaining after the PS DNase digestion step). 100 ng is sufficient to transfect ten 150 mm tissue culture dishes at 10 ng/dish. Note, the libraries can also be constructed by ligation or Gibson Assembly and then amplified in E. coli, but bacterial transformation reduces the library diversity. By directly transfecting the assembled reaction products, the library diversity is limited instead by the number of successfully transfected HEK293 producer cells.

TABLE 2

| | Primer sequences | |
|---|---|---|
| Primer | Purpose | Sequence |
| 9CapF | Step 1: forward | CAGGTCTTCACGGAC TCAGACTATCAG (SEQ ID NO: 57) |
| CDF | Step 1: reversed by Cre | CAAGTAAAACCTCTA CAAATGTGGTAAAAT CG (SEQ ID NO: 58) |
| XE | Step 2: forward | ACTCATCGACCAATA CTTGTACTATCTCTC TAGAAC (SEQ ID NO: 59) |
| AR | Step 2: reverse | GGAAGTATTCCTTGG TTTTGAACCA (SEQ ID NO: 60) |

TABLE 2-continued

Primer sequences

| Primer | Purpose | Sequence |
|---|---|---|
| TF | qPCR forward | GGTCGCGGTTCTTGT TTGTGGAT (SEQ ID NO: 61) |
| TR | qPCR reverse | GCACCCTTGAAGCGC ATGAACTCCT (SEQ ID NO: 62) |
| 7 × MNNN | 588i library generation reverse | GTATTCCTTGGTTTT GAACCCAACCGGTCT GCGCCTGTGCMNNMN NMNNMNNMNNMNNMN NTTGGGCACTCTGGT GGTTTGTC (SEQ ID NO: 63) |

Method of Virus Production and Purification

Recombinant AAVs were generated by triple transfection of 293T cells (ATCC) using polyethylenimine (PEI). Viral particles were harvested from the media at 72 hrs post transfection and from the cells and media at 120 hrs. Cell pellets were resuspended in 10 mM Tris with 2 mM $MgCl_2$, pH 8, freeze-thawed three times, and treated with 100 U/mL Benzonase (Epicentre) at 37° C. for at least 1 hr. Viral media was concentrated by precipitation with 8% polyethylene glycol 8000 (Sigma-Aldrich) with 500 mM sodium chloride, resuspended in Tris-$MgCl_2$, and then added to the lysates. The combined stocks were then adjusted to 500 mM NaCl, incubated at 37° C. for 30 minutes, and clarified by centrifugation at 2000× g. The clarified stocks were then purified over iodixanol (Optiprep, Sigma; D1556) step gradients (15%, 25%, 40% and 60%). Viruses were concentrated and formulated in phosphate buffered saline (PBS). Virus titers were determined by measuring the number of DNaseI resistant vg using qPCR with linearized genome plasmid as a standard.

For capsid library virus generation, two modifications were made to the above virus production protocol to reduce the production of mosaic capsids that could arise from the presence of multiple capsid sequences in the same cell. First, only 10 ng of the rAAV-Cap-in-cis library plasmid was transfected (per 150 mm dish) to increase the likelihood that most transfected cells only received one capsid variant sequence. Second, the virus was collected at 48 hrs (media) and 60 hrs (cells and media), rather than at 72 hrs and 120 hrs as described above, to minimize the secondary transduction of producer cells with Raav library virus released into the medium.

Animals

GFAP-Cre mice expressing Cre under the control of the mouse GFAP promoter (012886) and C57Bl/6J mice (000664) were purchased from the Jackson Laboratory (JAX). Intravenous administration of rAAV vectors was performed by injecting the virus into the retroorbital sinus. Mice were randomly assigned to groups of predetermined sample size. No mice were excluded from these analyses. Experimenters were not blinded to sample groups.

In Vivo Selection

For the selections in GFAP-Cre mice, $1 \times 10^{11}$ vg of the capsid libraries were injected intravenously into adult Cre+ mice of either sex. Seven to eight days post-injection, mice were euthanized and the brain and spinal cord were collected. Vector DNA was recovered from one hemisphere of the brain and half of the spinal cord using 4-5 ml of Trizol (Life Technologies; 15596). To purify viral DNA, the upper aqueous fraction was collected according to the manufacturer's extraction protocol. We found that the aqueous fraction contains a significant portion of the viral DNA genomes as well as RNA. RNA was then digested by treatment with 1 uL of RNase A (Qiagen) at 37° C. overnight. Next, a two-step PCR amplification strategy was used to selectively recover Cap sequences from Cre-recombined genomes. The first amplification step preferentially amplifies Cre-recombined rAAV-Cap-in-cis-lox sequences using the primers 9CapF and CDF (see FIGS. 8A-8B). The PCR was performed for 20-26 cycles of 95° C. for 20 sec, 60° C. for 20 sec and 72° C. for 30 sec using Q5 Hot Start High-fidelity DNA Polymerase. The PCR product was then diluted 1:10 or 1:100 and then used as a template for a second Cre-independent PCR reaction using primers XF and AR (FIGS. 8A-8B and Table 2). The second PCR generated the fragment that was cloned back into the rAAV-ΔCap-in-cis acceptor plasmid as described above. 1 µL of the Gibson Assembly reactions were then diluted 1:10 and transformed into SURE2 competent cells (Agilent; 200152) to generate individual clones for sequencing.

Variants that showed evidence of enrichment were cloned into an AAV Rep-Cap plasmid and transformed into DH5a competent cells (NEB). The novel AAV Rep-Cap variants, or AAV2/9 Rep-Cap as a control, were then evaluated using one of the reporter genomes described above.

Vector Biodistribution

Six-week-old mice female C57Bl/6 mice were injected intravenously with $1 \times 10^{11}$ vg of the ssAAV-CAG-GFP vector packaged into the indicated AAV capsid. Animals were randomly assigned to groups. 25 days after injection, the mice were euthanized and tissues and indicated brain regions were collected and frozen at −80° C. DNA was isolated from the tissue samples using Qiagen DNeasy Blood and Tissue kit. Vector genomes were detected using PCR primers that bind to the WPRE element and were normalized to mouse genomes using primers specific to the mouse glucagon gene. Absolute quantification was performed using serial dilutions of linearized plasmid standards of known concentration46. One randomly chosen animal injected with AAV-PHP.B was removed from the biodistribution study for histological analysis.

Tissue Preparation, Immunohistochemistry and Imaging

Mice were anesthetized with Nembutal and transcardially perfused with 0.1 M phosphate buffer (PB) at room temperature (RT) at pH 7.4 and then with freshly prepared, ice-cold 4% paraformaldehyde (PFA) in PB. Brains were post-fixed in 4% PFA overnight and then sectioned by vibratome or cryoprotected and sectioned by cryostat. IHC was performed on floating sections with primary and secondary antibodies in PBS containing 10% goat or donkey serum and 0.5% Triton X-100 (no detergent was used for GAD67 staining). Primary antibodies used were mouse anti-AAV capsid (1:20; American Research Products, 03-65158, clone B1), rabbit anti-GFP (1:1000; Invitrogen, A11122), chicken anti-GFP (1:1000; Abcam, ab13970), mouse anti-CC1 (1:200; Calbiochem, OP80), rabbit anti-GFAP(1:1000; Dako, Z0334), mouse anti-NeuN (1:500; Millipore, MAB377), rabbit anti-Iba1 (1:500; Biocare Medical, CP290), mouse anti-Calbindin D28K (1:200; Sigma, CB-955), rabbit anti-Calretinin (1:1000; Chemicon, AB5054), mouse anti-GAD67 (1:1000; Millipore, MAB5406), guinea pig anti-MAP2 (1:1000; Synaptic Systems, 188004), mouse anti-Parvalbumin (1:1000; Sigma), Tyrosine Hydroxlyase (1:1000; Ayes) and rabbit anti-CD31 (1:50; Abcam, ab28364). Primary antibodies incubations were performed for 16-24 hrs at RT. The sections were then washed and incubated with secondary Alexa-conjugated antibodies (1:1000; Invitrogen) for 2-16 hrs. For capsid detection with the B1 antibody that recognizes an internal epitope, floating sections were treated with 2M HCl for 15 minutes at 37° C. and then washed extensively with PBS prior to incubation with the primary antibody. For some images, the 16-bit green channel (GFP) gamma was adjusted to enable visualization (without oversaturation) of both low and high GFP-expressing cells present within the same field of view. In all cases, changes to gamma or contrast as well as microscope and laser settings remained consistent across sets of images. Images were taken with a Zeiss LSM 780 confocal microscope fitted with the following objectives: Fluar 5×/0.25 M27 Plan-Apochromat 10×/0.45 M27 (working distance 2.0 mm), Plan-Apochromat 25×/0.8 Imm Corr DIC M27 multi-immersion and LD CApochromat 40×/1.1 W Korr and Plan-Apochromat 100×/1.46 Oil DIC objectives. 3D MIP images and Supplementary Movies were generated with Imaris (Bitplane).

Quantification of Cell Type-Specific Transduction

Six-week-old female mice were randomly assigned to groups and injected intravenously with $2\times10^{12}$ vg of ssAAV-CAG-NLS-GFP packaged into AAV9, AAV-PHP.B or AAV-PHP.A. Three weeks later, the mice were perfused and the brains were processed and immunostained for the indicated antigen as described above. The number of animals per group was pre-established; no animals were excluded from the analysis. Confocal single-plane images of the cell type-specific immunostaining and native NLS-GFP fluorescence were taken. To prevent bias, images were taken from the indicated matched regions identified by viewing only the cell type-specific immunostaining channel, rather than from GFP expression, prior to image acquisition. Likewise, cell counting was performed by first counting and marking each cell stained by the cell-specific antigen by viewing the MC channel. Next those marked IHC+ cells that were positive for native GFP fluorescence were counted. Due to the stark transduction efficiency differences between capsids, the counting was not blinded by group.

Tissue Clearing

Mice were perfused as above with 60-80 mL of ice-cold 4% PFA in PB at a flow rate of 14 mL per minute. The flow rate was then reduced to 2-3 mL/min and continued for 2 hrs at RT. The mice were then placed in individual custom-built chambers and perfused with 200 mL of recycling RT 4% acrylamide in PB at 2-3 mL/min overnight followed by a 2-hr perfusion flush with PB to remove residual polymers/monomers from the vasculature. The polymerization process was initiated by placing the chambers in a 42° C. water bath and delivering, by perfusion (2-3 mL/min), of 200 mL of recycling, degassed PB containing 0.25% VA-044 initiator for 2-4 hrs. The mice were then perfused with 8% SDS in PB, pH 7.5 for 7 days. The SDS containing solution was refreshed two times during the 7 days and then flushed out by perfusion of 2 L of non-recirculating PB overnight. Cleared tissue samples were mounted in RIMS solution (refractive index of 1.46) for imaging.

Generation of Cortical Spheroids from Human iPSC

Human cortical spheroids were generated from iPSC as previously described. Briefly, iPSC lines derived from two healthy control individuals were grown on inactivated mouse embryonic fibroblast feeders in the following medium: DMEM/F12, Knockout Serum 20%, 1 mM non-essential amino acids (1:100), GlutaMax (1:200), β-mercaptoethanol (0.1 mM), penicillin and streptomycin (1:100) (Life Technologies). Cultures were regularly tested and maintained mycoplasma free. Colonies of iPSCs were detached intact with dispase (0.35 mg/ml, Invitrogen) and transferred into low-attachment plates in iPSC medium supplemented with dorsomorphin (5 μM, Sigma) and SB-431542 (10 μM, Tocris), and the medium was changed daily. On day six of in vitro differentiation, neural spheroids were transferred to NPC medium (Neurobasal A, B27 without vitamin A, GlutaMax (1:100), penicillin and streptomycin; Life Technologies), which was supplemented with EGF (20 ng/ml) and FGF2 (20 ng/ml) until day 24, and then supplemented with BDNF (20 ng/ml) and NT3 (20 ng/ml) from day 25 to 42. From day 43 onwards, cortical spheroids were maintained in NPC medium, which was changed every 4 days.

Dissociation and Viral Infection of Cortical Spheroids

For enzymatic dissociation and culture in monolayer, cortical spheroids at day 170-200 of in vitro differentiation (two independent neural differentiations of one iPSC line from one individual and one differentiation of an iPSC line from another individual) were incubated with Accutase (Innovative Cell Technologies) for 25 min at 37° C., washed three times with NPC media and gently triturated with a P-200 pipette. Cells were plated on poly-ornithine and laminin coated glass coverslip (15 mm) at ~300,000 cells/well and maintained in NPC media supplemented with BDNF (20 ng/ml) and NT3 (20 ng/ml) for the first 24 hrs, and then maintained in NPC media without growth factors.

Cultures grown on coverslips were infected with each of the viruses at a titer of $1\times10^9$ vg/well and fixed 5 days later with 4% paraformaldehyde (PFA) for 10 min. For immunocytochemistry, cells were permeabilized with 0.2% Triton X-100 for 10 min and blocked with 10% goat serum in PBS for 1 hr. Coverslips were then incubated with antibodies diluted in blocking solution for 2 hr. Nuclei were visualized with Hoechst 33258 (Life Technologies, 1:10,000).

Cells were imaged with a Zeiss M1 Axioscope using a 40× objective. The proportion of GFP+ cells colabeled with either GFAP or MAP2 was quantified in images of 10 random fields per coverslip for each experimental condition. Results presented are the average of two separate dissociation and infection experiments.

To infect intact 3D cultures with AAVs, single human cortical spheroids at day 197 days of in vitro differentiation were transferred overnight into 1.5 ml Eppendorf tubes containing $6\times10^9$ vg/400 μl in NPC media, and were fixed 7 days later in 4% PFA overnight. Fixed spheroids were then transferred into 30% sucrose for 24 hrs, embedded in O.C.T. (Fisher Scientific) and cut at 14 μm sections. For immunohistochemistry, sections were blocked with 10% goat serum in PBS containing 0.3% Triton-X100 for 1 hr. Images were collected with a Leica TCS SP8 confocal microscope.

Generation of RAAV Variants using CREATE

CREATE uses an rAAV capsid genome (rAAV-Cap-in-cis-lox) that couples a full-length AAV Cap gene, controlled by regulatory elements from the AAV Rep gene (FIG. 4B), with a Cre invertible switch (FIG. 4B). By building capsid libraries within the rAAV-Cap-in-cis-lox backbone and delivering the virus libraries to animals with Cre expression in a defined cell population, the system enables the selective amplification and recovery of sequences that have transduced the target population (FIG. 4C). Because the rAAV-Cap-in-cis-lox genome lacks a functional Rep gene, Rep must be provided in trans for virus production. For this purpose, the AAV2/9 rep-cap plasmid can be modified to eliminate capsid protein expression by inserting in-frame stop codons within the reading frame for each capsid protein, VP1-3 (FIG. 4D). These stop codons do not alter the amino acid sequence of the assembly activating protein (AAP), which is expressed from an alternative reading frame within the Cap gene22. This split rAAV-Cap-in-cis-lox genome and Rep-AAP AAV helper system efficiently generates rAAV (FIG. 4E) and is the foundation of the CREATE selection platform, which enables capsid sequence recovery from genetically defined Cre-expressing cell populations within heterogeneous tissue samples (see FIGS. 8A-8B).

Figure 9A:
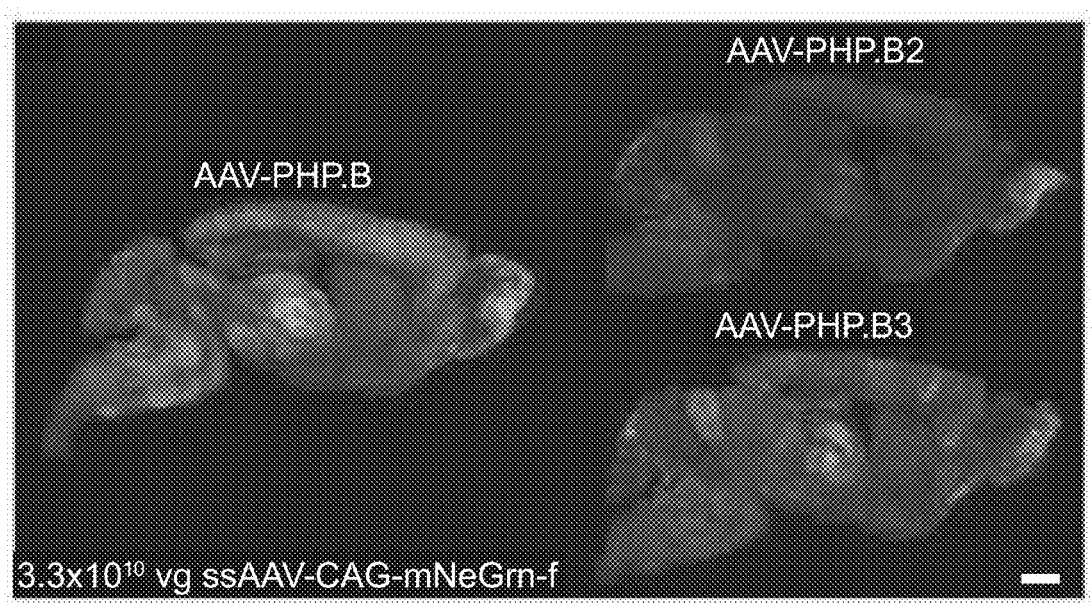
FIGS. 9A-9B depict capsid characteristics and production efficiencies of the three most enriched variants (i.e., AAV-PHP.B, AAV-PHP.B2 and AAV-PHP.B3) from each selection.

Within the rAAV-Cap-in-cis-lox acceptor genome a library was generated of AAV variants through inserting 7 amino acids (AA) of randomized sequence (7-mer) between AA588-589 (VP1 position) of the AAV9 capsid (FIGS. 4F-4G). To select for vectors that crossed the BBB and transduced cells throughout the CNS, the capsid library was administered intravenously into adult GFAP-Cre mice, which express Cre in astrocytes. One week later, DNA was isolated from brain and spinal cord tissue and recovered capsid sequences by PCR from viral genomes that had undergone Cre-mediated recombination. The entire library of recovered Cap sequences was cloned back into the rAAV-Cap-in-cis-lox acceptor genome to generate the library GFAP1 and randomly chose 13 clones for sequencing. All tested sequences recovered from the GFAP1 library were unique, and therefore the GFAP1 plasmid library was used to generate a second virus library and performed an additional round of selection in GFAP-Cre mice. After the second selection, several variants were enriched (see Table 3) and showed enhanced CNS transduction (FIG. 9A). The most enriched variant, AAV-PHP.B, was chosen for further tropism evaluation in vivo. AAV-PHP.B represented 25% of recovered library sequences and encodes the 7-mer sequence TLAVPFK (SEQ ID NO: 40).

Figure 5E:
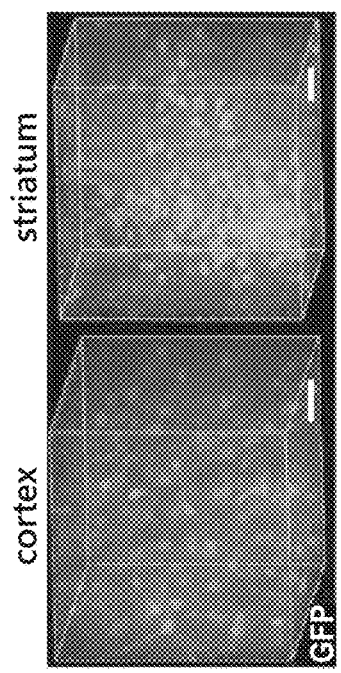
Figure 5F:
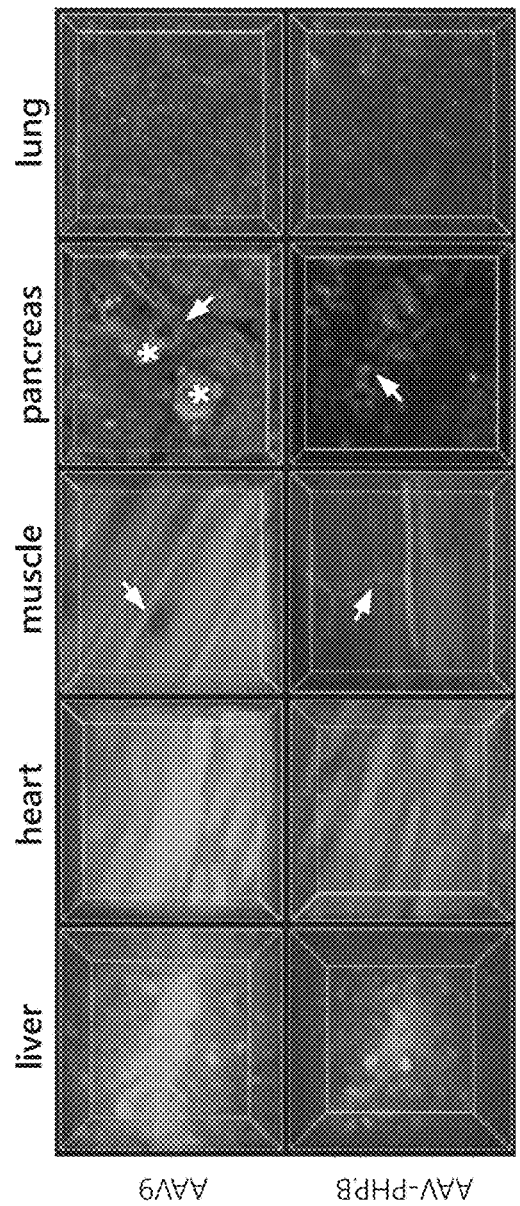
Figure 9B:
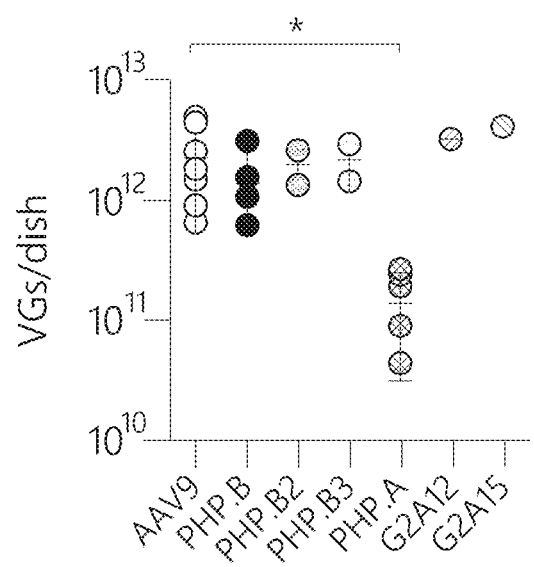

AAV-PHP.B and AAV9 capsids were used to package a single-stranded (ss) GFP reporter vector driven by the ubiquitous CAG promoter (ssAAV-CAG-GFP). Both AAV-PHP.B and AAV9 produced virus with similar efficiencies (FIG. 9B). Vector genomes (vg) of either vector in the amount of $1\times10^{12}$ were administered to six-week-old mice by intravenous injection. Transduction was assessed by GFP expression three weeks later. The data show that AAV-PHP.B transduced the entire adult CNS with high efficiency as indicated by imaging GFP immunohistochemistry (IHC) (FIG. 5A) or native eGFP fluorescence in several brain regions (FIG. 5B), the spinal cord (FIG. 5C) and retina (FIG. 5D). Using PARS-based CLARITY for whole body tissue clearing24, native eGFP fluorescence was detected through cleared sections of tissue from the spinal cord (FIG. 5C), cortex and striatum (FIG. 5E). These 3D renderings demonstrate the broad and efficient CNS transduction with the AAV-PHP.B vector. Outside the CNS, the cellular level tropism of AAV-PHP.B and AAV9 appeared similar in several organs, with the exception of the pancreas where the efficiency of transduction by AAV-PHP.B was reduced as compared with AAV9 (FIG. 5f).

Figure 5G:
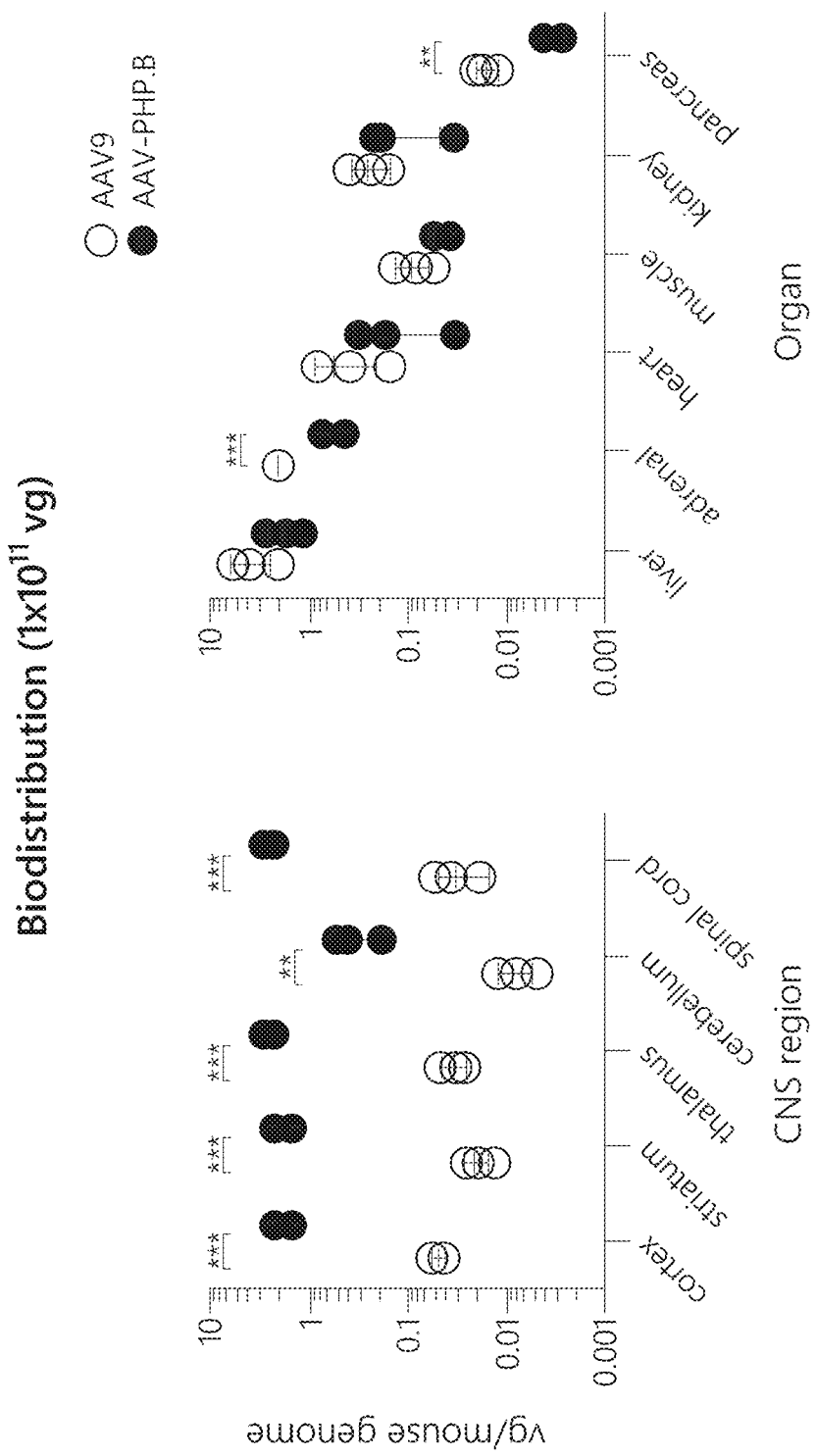

To quantify the efficiency of gene transfer to the CNS and peripheral organs by AAV-PHP.B as compared with AAV9, the number of viral genomes present was measured in several brain regions and organs 25 days post-injection (FIG. 5G). AAV-PHP.B provided significantly greater gene transfer than AAV9 to each of the CNS regions examined: cortex (40-fold), striatum (92-fold), thalamus (76-fold), cerebellum (41-fold) and spinal cord (75-fold). Vector genome biodistribution outside the CNS showed that AAV-PHP.B transferred genes to the pancreas and adrenal gland less efficiently than AAV9 (FIG. 5G). No significant differences were found between the two vectors in the liver, heart, skeletal muscle and kidneys. When considered together with the CNS biodistribution data, in all CNS areas except the cerebellum, the number of viral genomes detected in mice treated with AAV-PHP.B was similar to that measured in the liver, an organ efficiently transduced by AAV921,25, and greater than that observed in other organs. In contrast, AAV9-mediated gene transfer to each of the examined CNS regions was at least 120-fold lower than in the liver. Therefore, although the tropism of AAV-PHP.B is not CNS specific, the enhanced gene transfer characteristics of this vector are CNS specific.

Figure 6A:
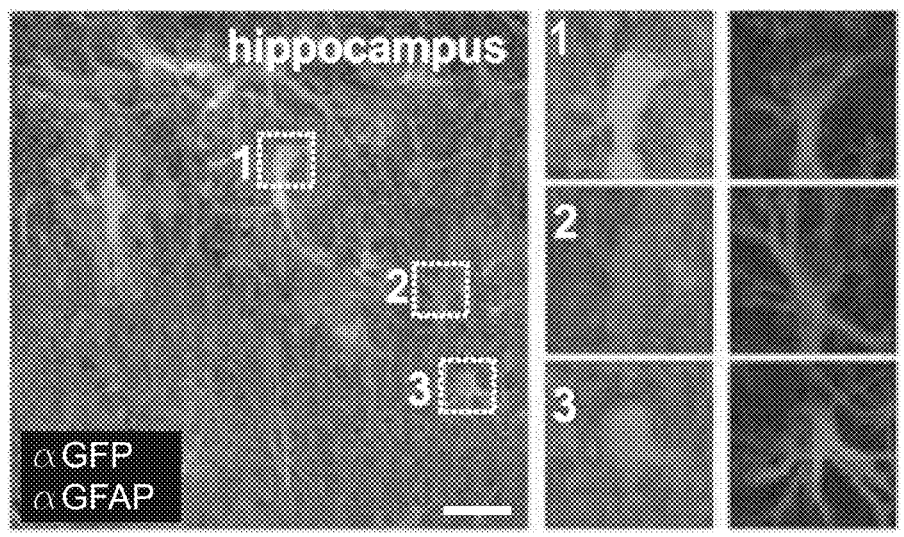
FIGS. 6A-6I depict AAV-PHP.B transducing multiple CNS cell types more efficiently than AAV9.
Figure 6B:
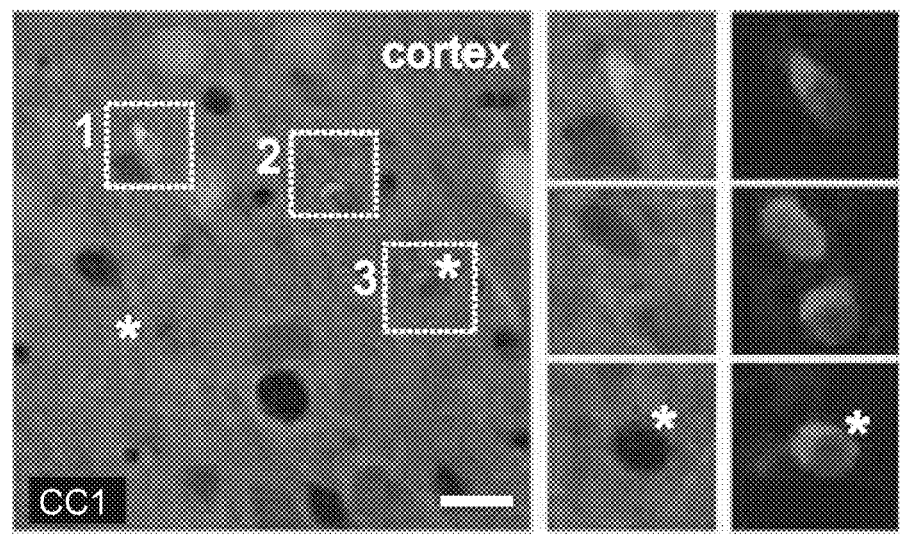
Figure 6C:
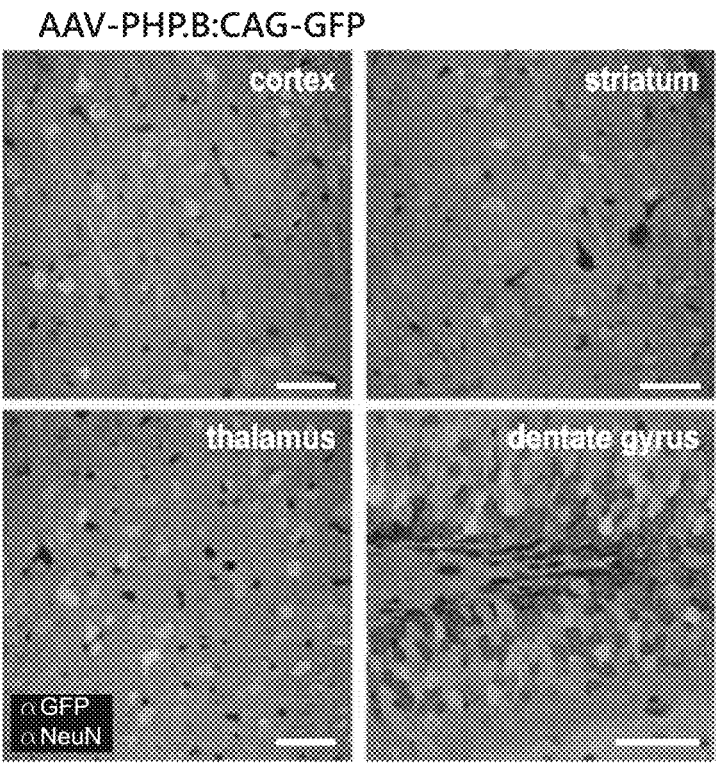
Figure 6D:
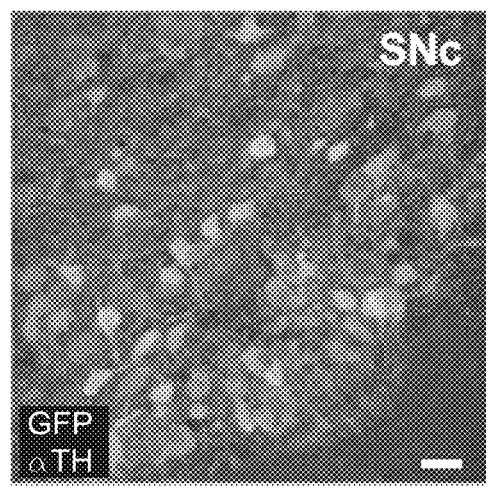
Figure 6E:
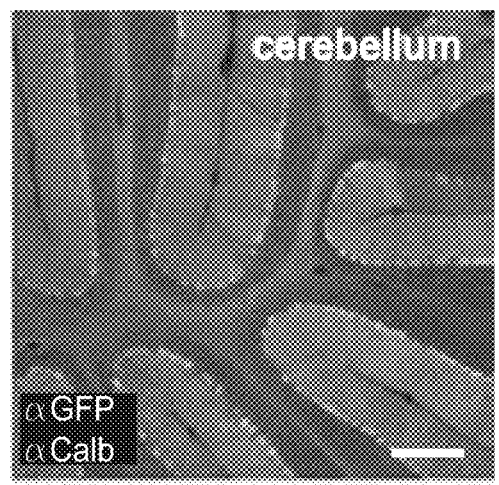
Figure 10A:
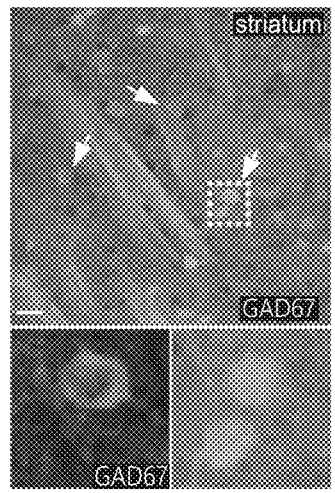
FIGS. 10A-10G are images showing that AAV-PHP.B transduces several interneuron cell types and endothelial cells but does not transduce microglia.
Figure 10B:
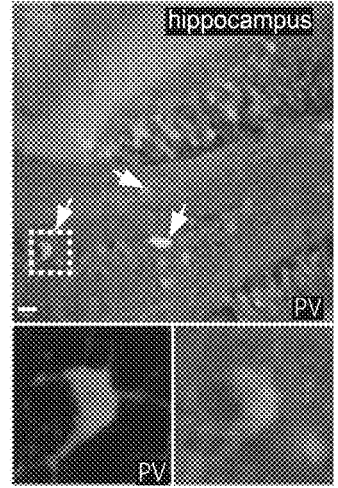
Figure 10C:
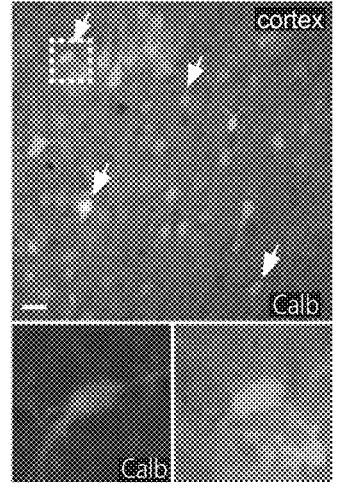
Figure 10D:
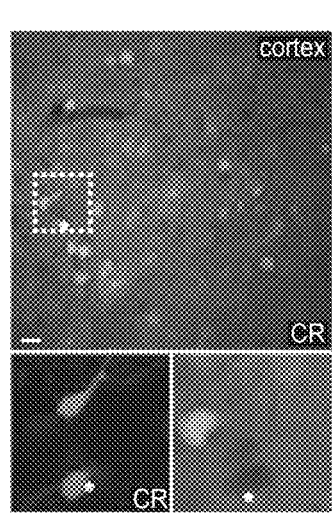
Figure 10E:
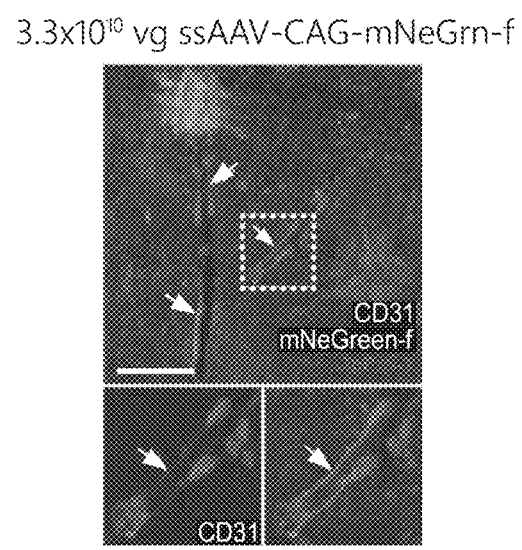
Figure 10F:
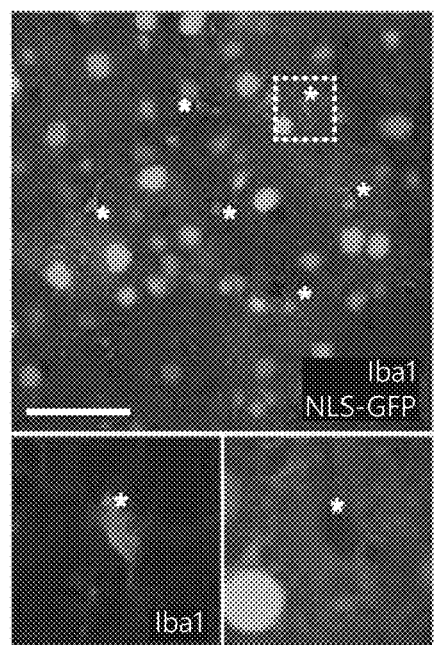
Figure 10G:
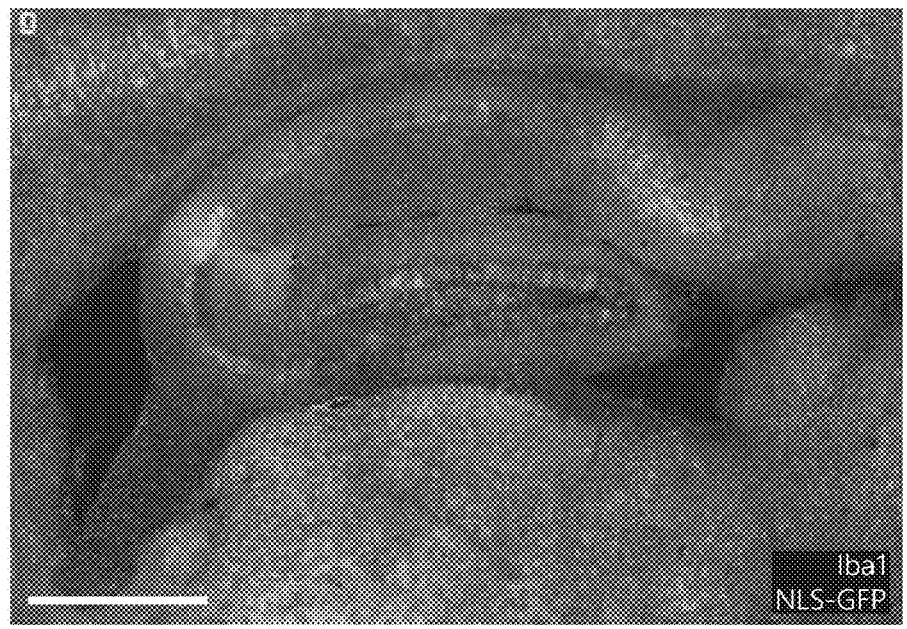
Figure 11:
FIG. 11 depicts long-term AAV-PHP.B expression in the brain following gene transfer with AAV-PHP.B. Adult mice were intravenously injected with the indicated dose of ssAAV-CAG-GFP packaged into AAV9 or AAV-PHP.B and were assessed for native eGFP fluorescence 377 days later. Bright signals indicate eGFP expression. N=1 per vector/ dose.

AAV9 preferentially transduces astrocytes when delivered intravenously to adult mice and nonhuman primates, but it also transduces neurons in several regions. To examine the cell types transduced by AAV-PHP.B, the co-localization of GFP with several cell-type markers was analyzed. Owing to the highly efficient transduction, individual GFP expressing astrocytes were difficult to discern in mice that received $1\times10^{12}$ vg AAV-PHP.B (FIG. 5A), but could be more easily identified morphologically by their compact, highly ramified processes in animals that received 10-fold less virus (FIGS. 5A-5B) and by co-localization with IHC for GFAP (FIG. 6A). In addition to astrocytes, AAV-PHP.B transduced CC1+ oligodendrocytes (FIG. 6B) and all neuronal subtypes examined, including NeuN+ throughout the brain (FIG. 6C) as well as midbrain tyrosine hydroxylase (TH)$^+$ dopaminergic neurons (FIG. 6D), Calbindin+ cerebellar Purkinje cells (FIG. 6E), and several interneuron populations (FIGS. 10A-10D). AAV-PHP.B also transduced CD30+ endothelial cells (FIG. 10E) but did not appear to transduce Iba1+ microglia (FIGS. 10F-10G). The paucity of GFP+ microglia seen after intravenous AAV-PHP.B delivery is consistent with previous reports of rare or nonexistent AAVmediated gene expression in this cell population14,27-30. Native GFP fluorescence from GFP protein expression was observed throughout the brain over a year after administration of AAV-PHP.B, suggesting that AAV-PHP.B can provide long-term, CNS-directed transgene expression (FIG. 11).

Figure 6G:
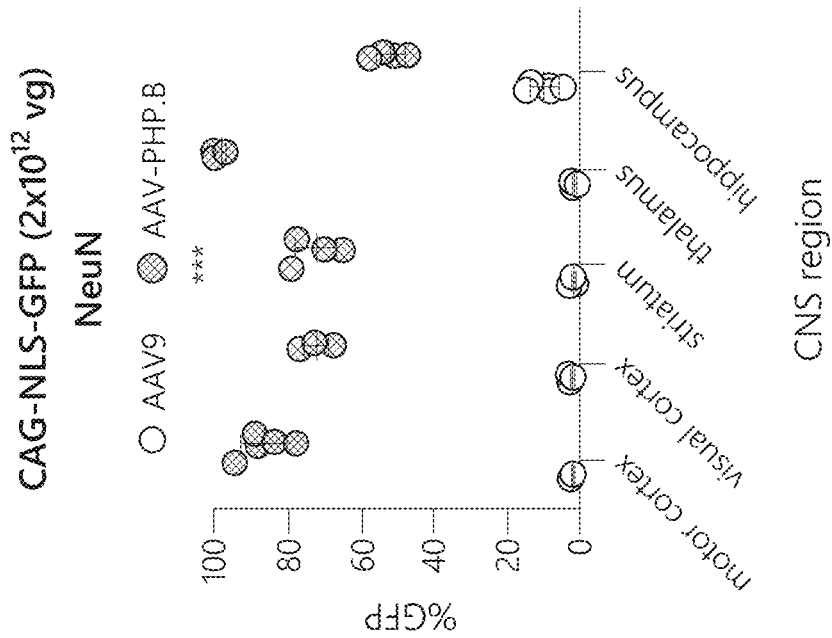
Figure 6F:
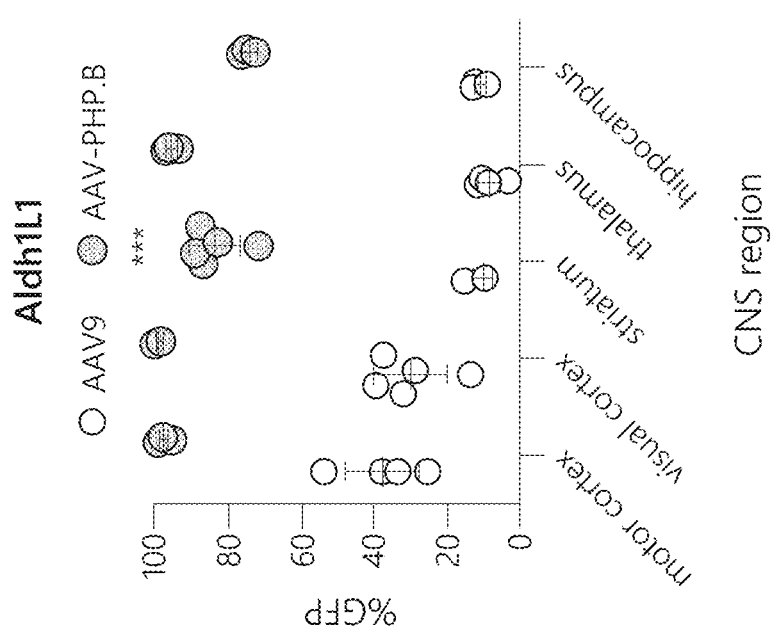
Figure 6H:
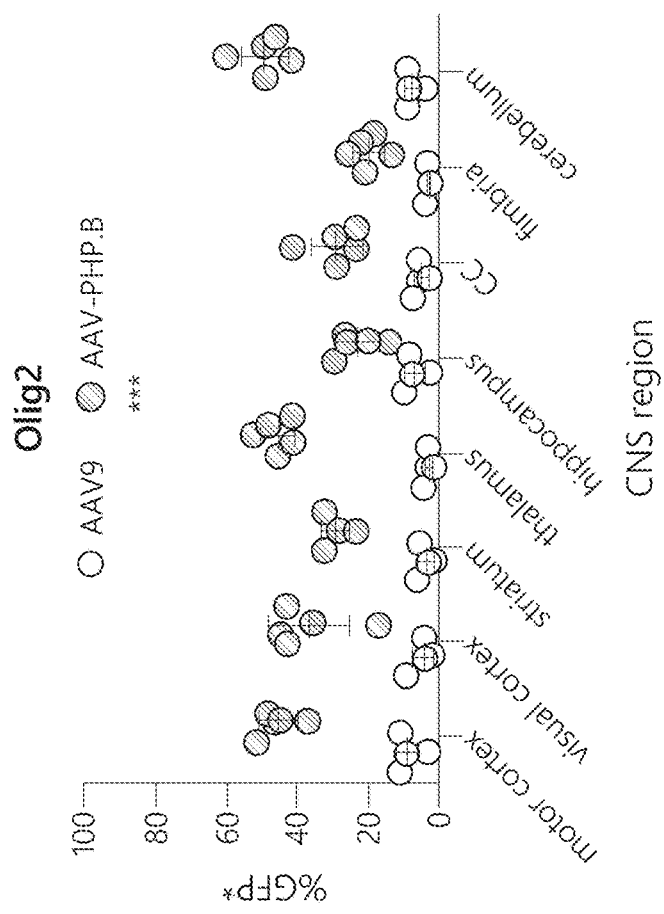
Figure 6I:
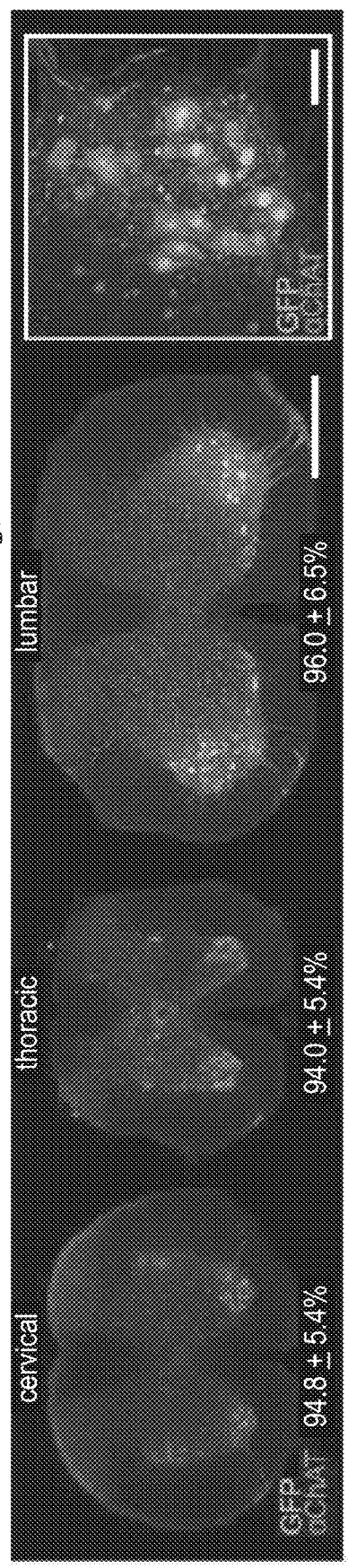
Figure 12A:
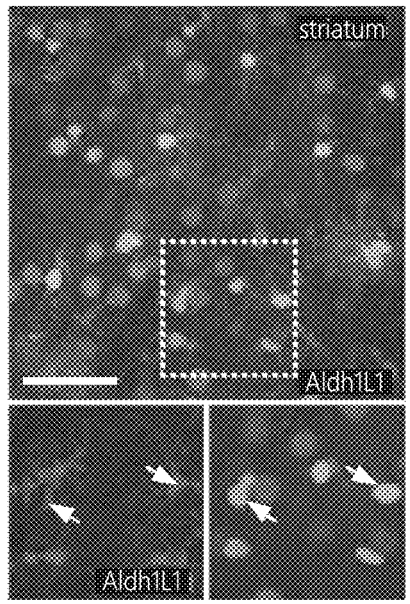
FIGS. 12A-12D are representative images of native fluorescence from GFP protein expression and IHC for several neuron and glial cell types following transduction by AAV-PHP.B:CAG-NLS-GFP.
Figure 12B:
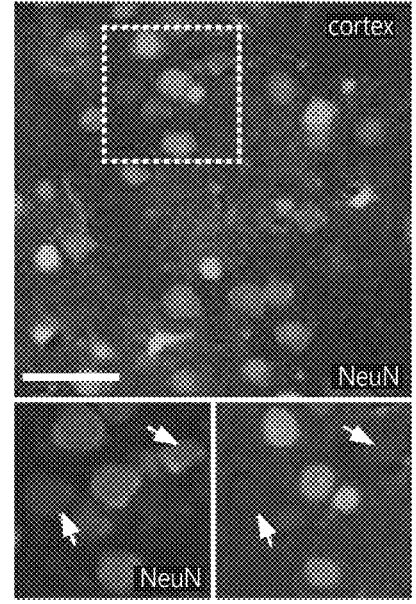
Figure 12C:
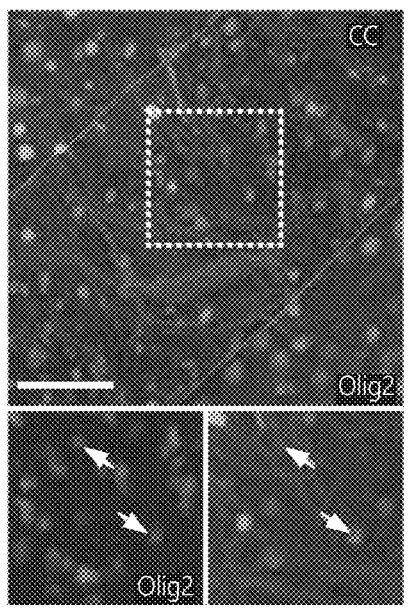
Figure 12D:
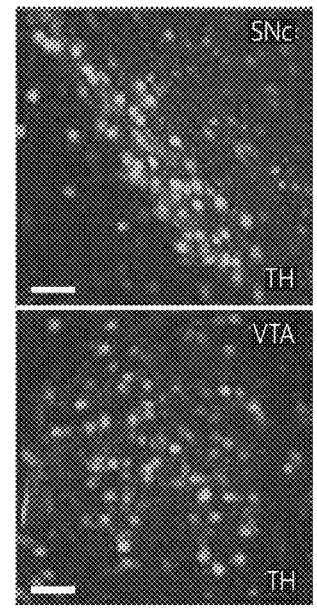

Next, the fraction of several cell types transduced by AAV-PHP.B was quantified and compared to AAV9. To facilitate reliable individual cell counting, a vector expressing a nuclear localized GFP (NLS-GFP) under the control of the CAG promoter, ssAAV-CAG-NLS-GFP was constructed. A single injection of $2\times10^{12}$ vg/mouse of ssAAV-PHP.B:CAG-NLS-GFP transduced the majority of Aldh1L1+ astrocytes (FIGS. 6F and 12A) and NeuN+ neurons (FIGS. 6G and 12B), as well as a modest fraction of Olig2+ oligodendrocyte lineage cells (FIGS. 6H and 12C) across all brain regions examined. In all cases, AAV-PHP.B provided significantly enhanced transduction as compared to the same dose of AAV9. Notably, AAV-PHP.B also transduced over 94% of Chat+ motor neurons throughout the spinal cord (FIG. 3I), 91.4±1.6% of TH+ midbrain dopaminergicneurons (FIG. 12D) and 91.7±5.8% of Calbindin+ Purkinje cells (n=5). In sum, adult intravenous administration of AAV-PHP.B efficiently targets multiple neuronal and glial cell types in the adult mouse.

Figure 7A:
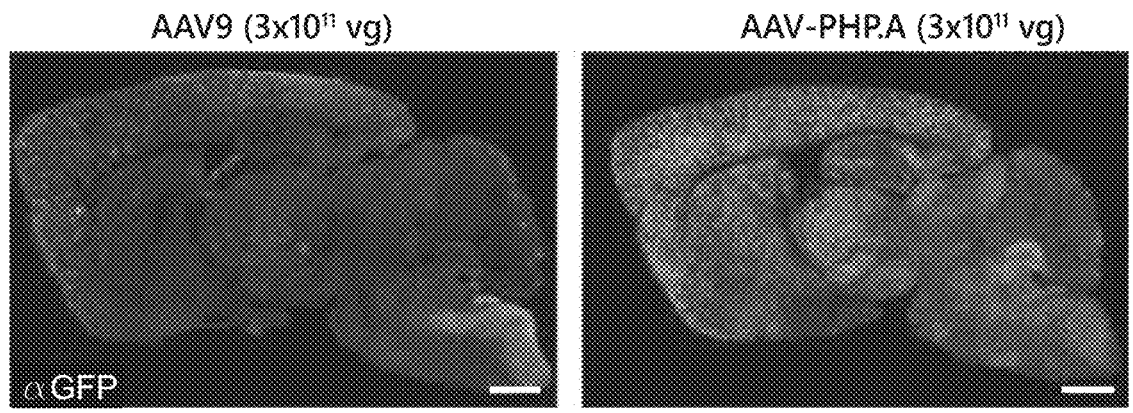
FIGS. 7A-7F depict AAV-PHP.A transduction of CNS astrocytes and reduced tropism for peripheral organs.
Figure 7B:
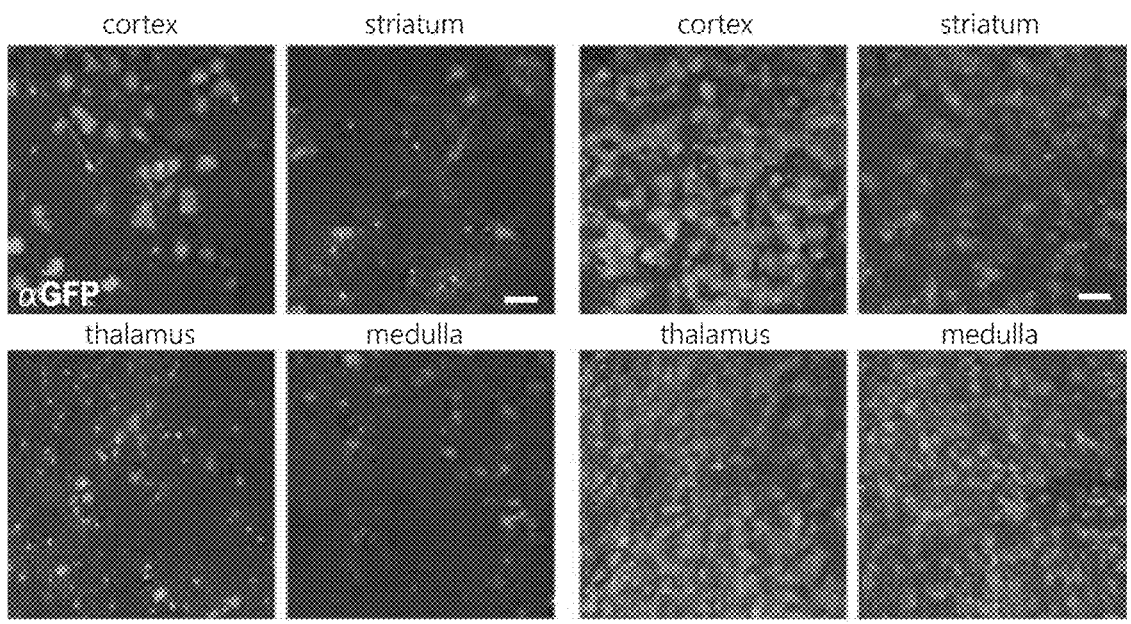
Figure 7C:
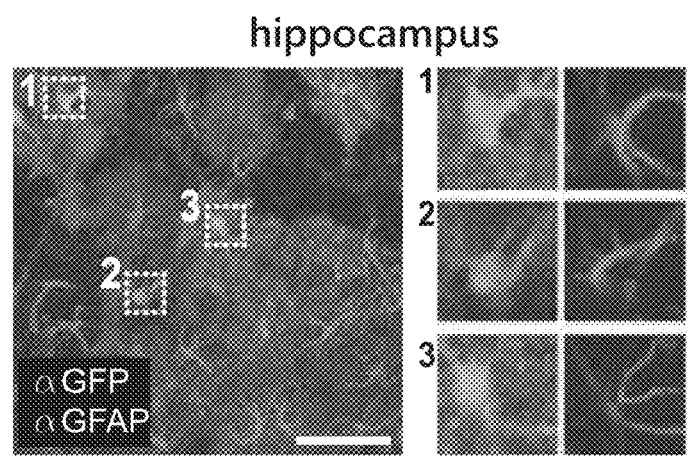
Figure 7D:
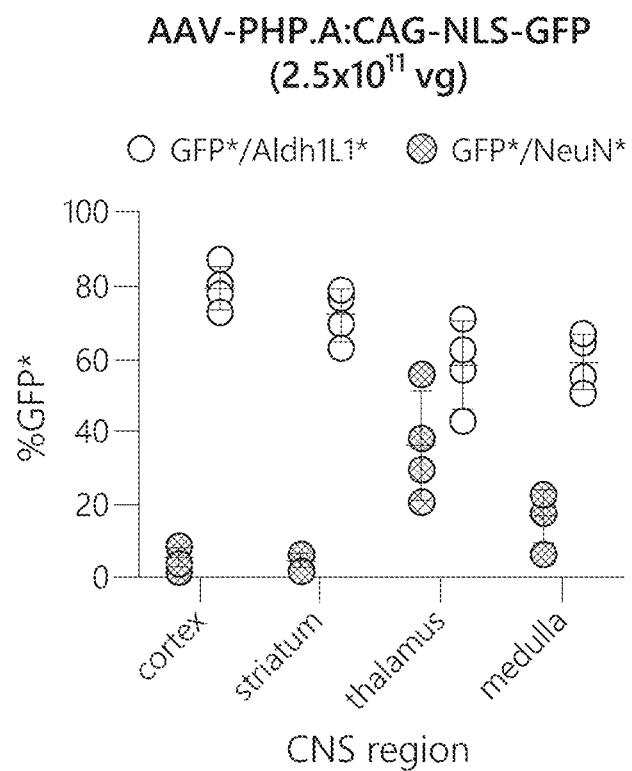
Figure 7E:
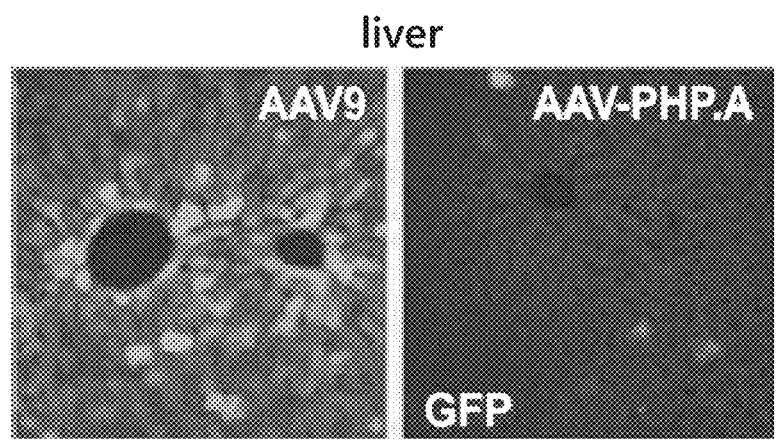
Figure 7F:
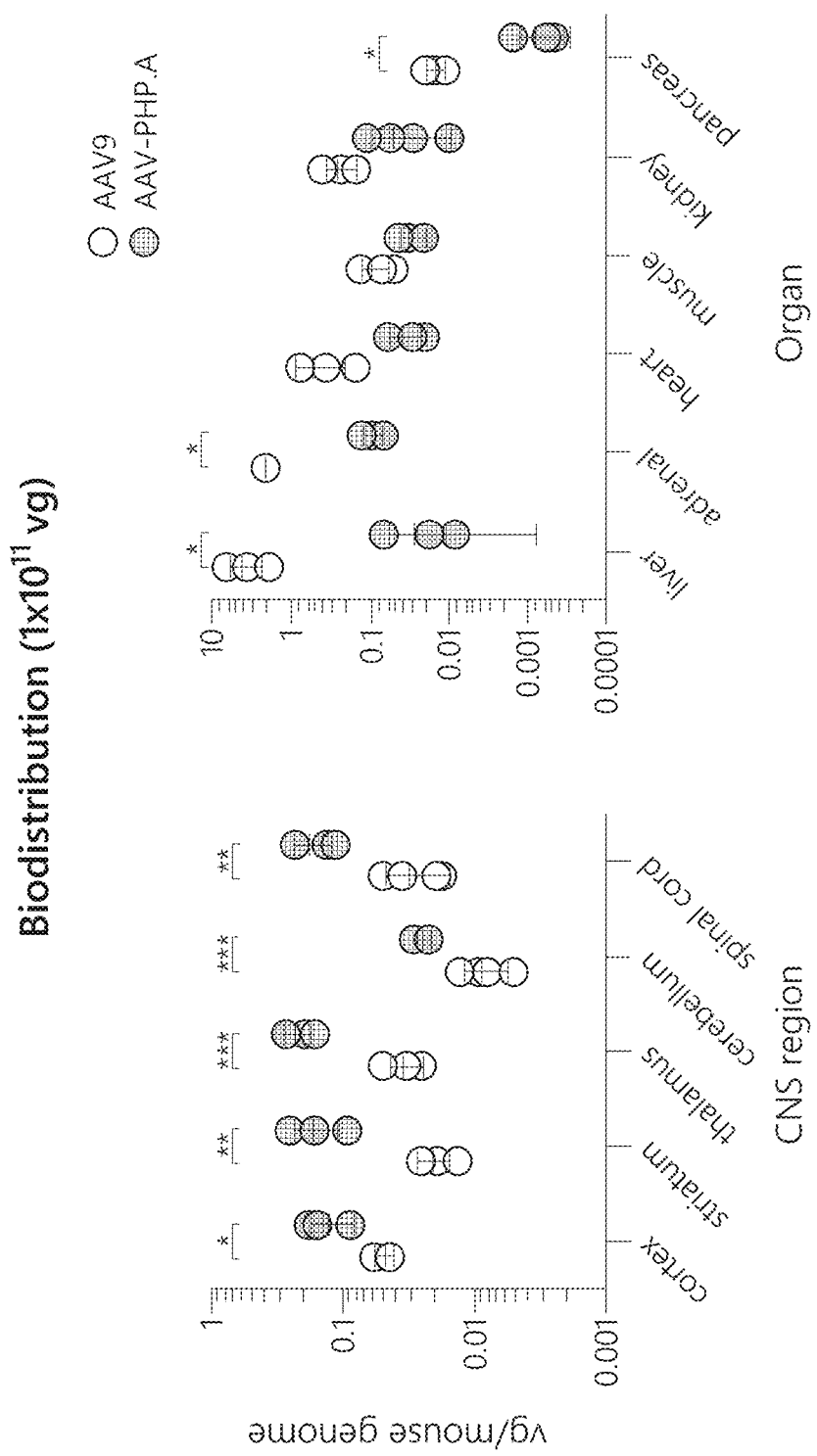

The method used to identify AAV-PHP.B only selects for transduction of the target cell population; it does not necessarily select for specificity. Nevertheless, in a separate trial in GFAP-Cre mice, (after two rounds of in vivo selection) another AAV capsid variant, AAV-PHP.A was identified. AAV-PHP.A contains a 7-mer sequence, YTLSQGW (SEQ ID NO: 38), that exhibits both more efficient and selective CNS astrocyte transduction (FIGS. 7A-7D), as well as reduced tropism for the liver (FIGS. 7E-7F) and other peripheral organs (FIG. 7F), as compared to AAV9. The increase in specificity for gene transfer to the CNS over the liver provided by AAV-PHP.A versus AAV9 is 400- to 1200-fold, resulting from a combination of enhanced adult CNS gene transfer (2.6- to 8-fold more depending on the specific region) and reduced liver gene transfer (152-fold). Two other variants enriched in this trial (FIG. 9A) did not show enhanced GFP expression in CNS neurons or glia as compared with AAV9.

Figure 13A:
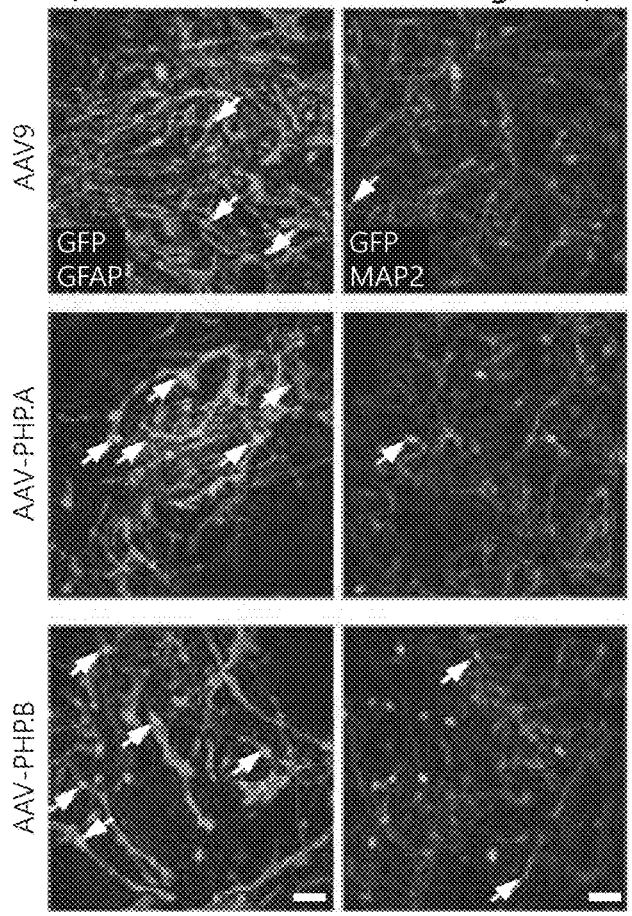
FIGS. 13A-C show AAV-PHP.A and AAV-PHP.B transduction of human iPSC-derived cortical neurons and astrocytes in associated cultures and intact 3D cortical cultures.
Figure 13B:
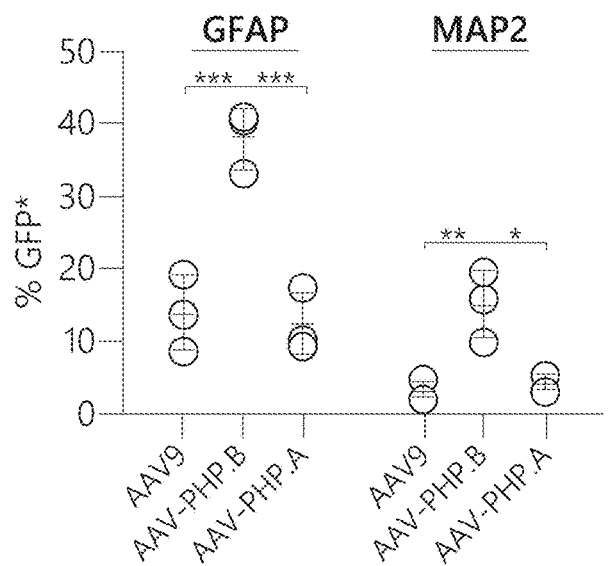
Figure 13C:
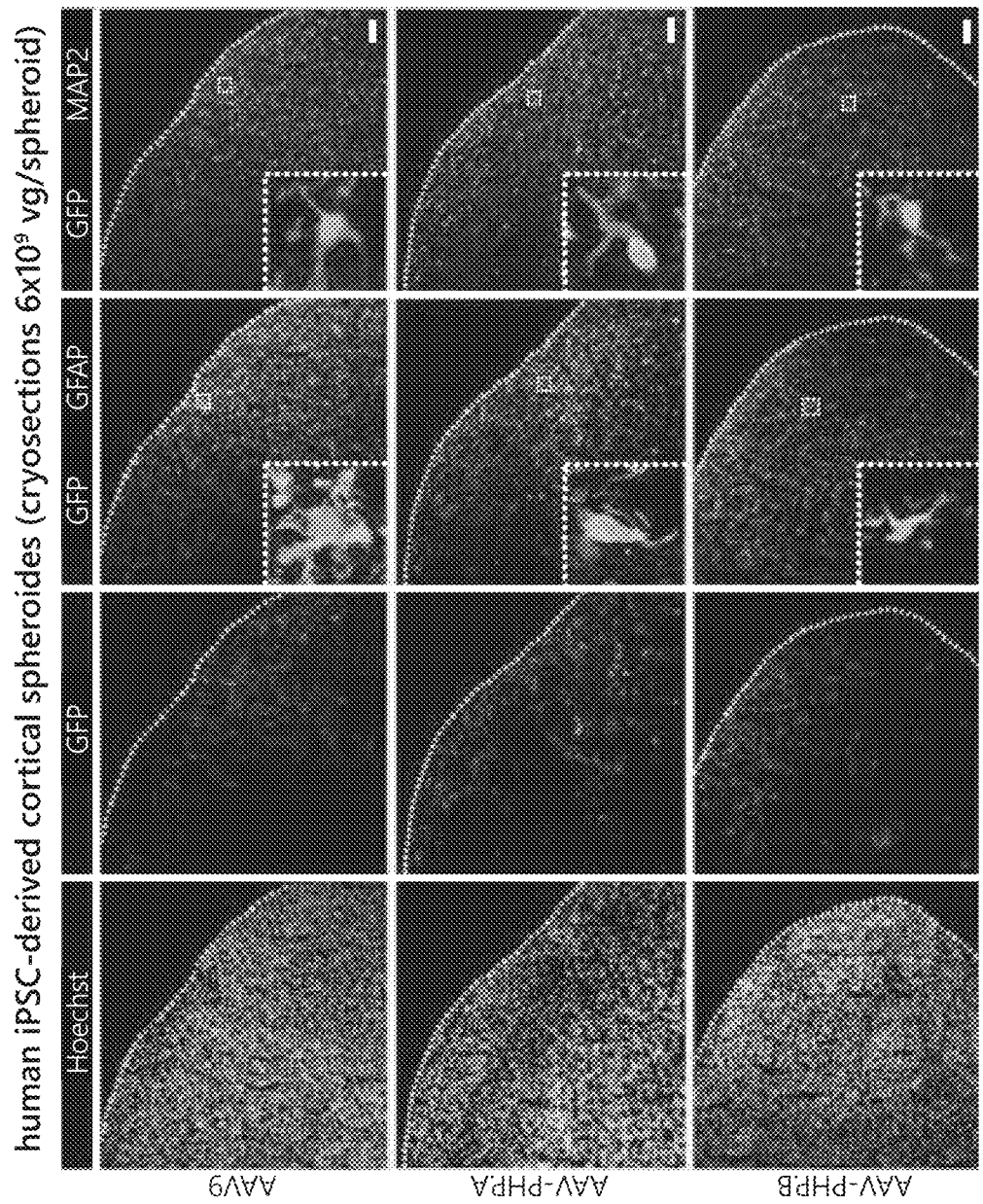
Figure 14A:
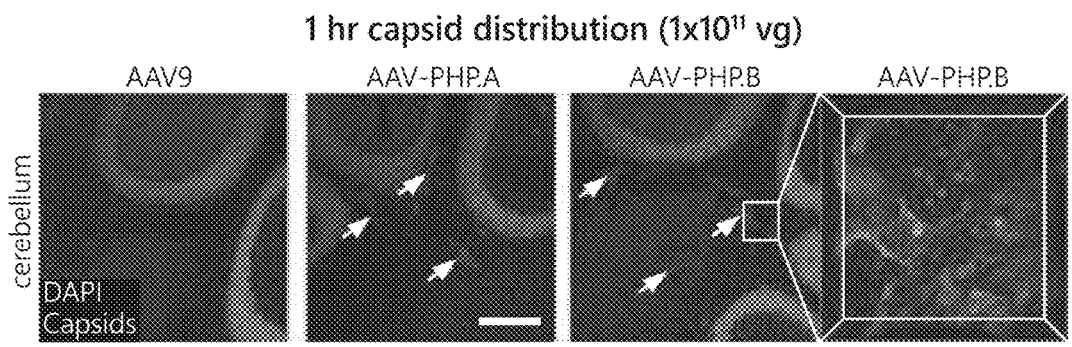
FIGS. 14A-14D depict AAV-PHP.B and AAV-PHP.A capsids localizing to the brain vasculature after intravenous injection and transducing cells along the vasculature by 24 hours post-administration. Adult mice were injected with $1 \times 10^{11}$ vg of ssAAV-CAG-NLS-GFP packaged into AAV9, AAV-PHP.A or AAV-PHP.B as indicated.
Figure 14B:
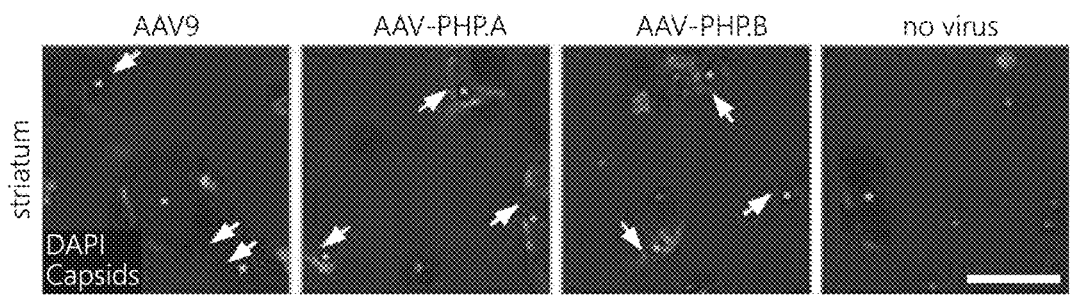
Figure 14C:
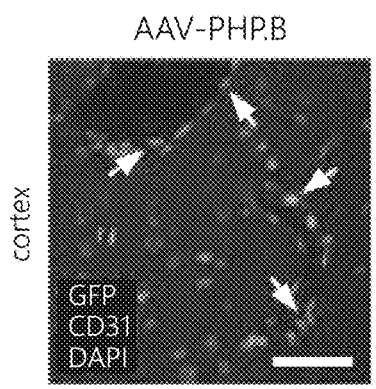
Figure 14D:
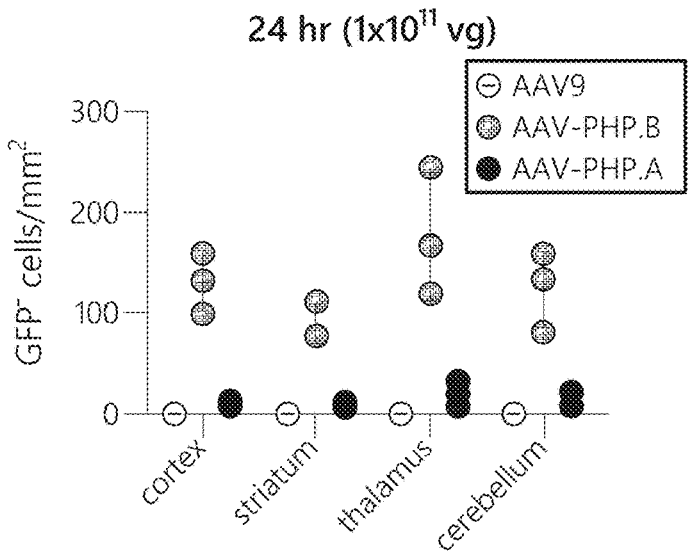
Figure 15A:
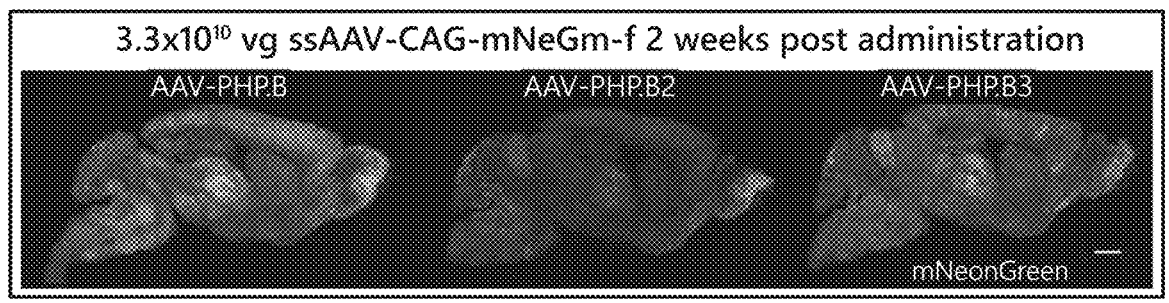
FIGS. 15A-15B show reporter expression from the top three variants recovered from GFAP-Cre mice.
Figure 15B:
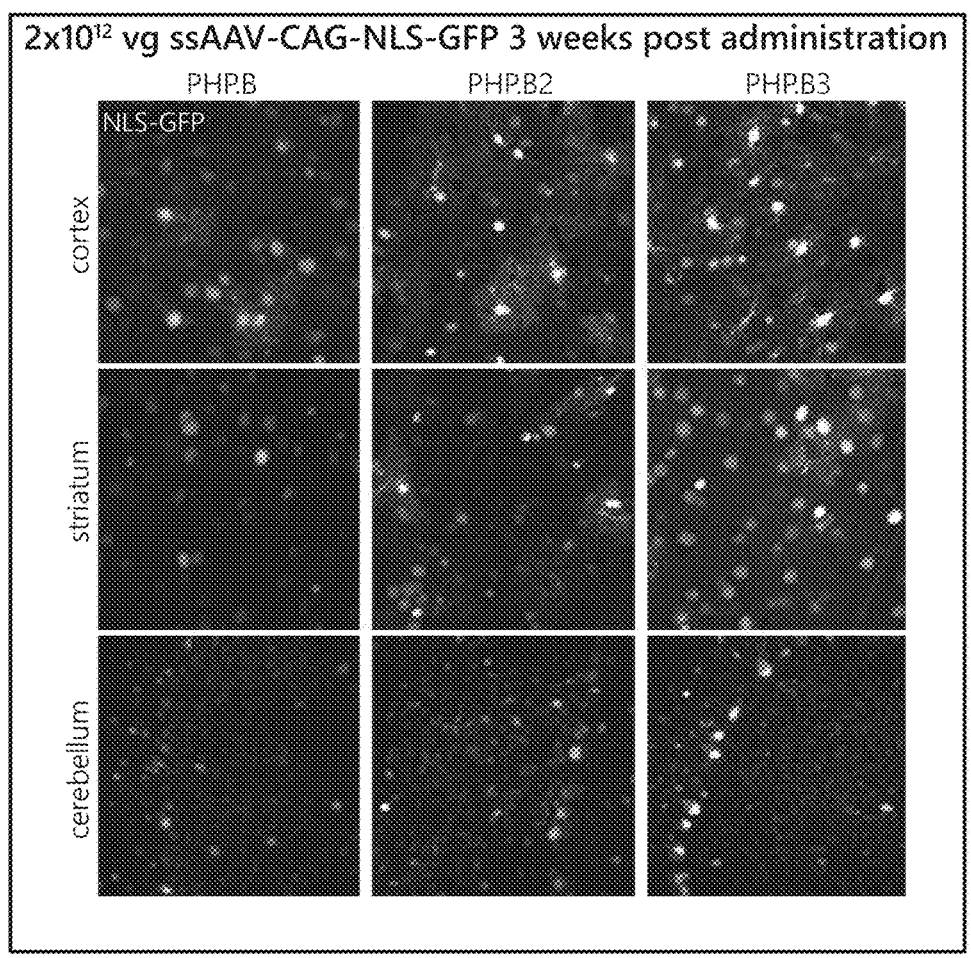
Figure 16:
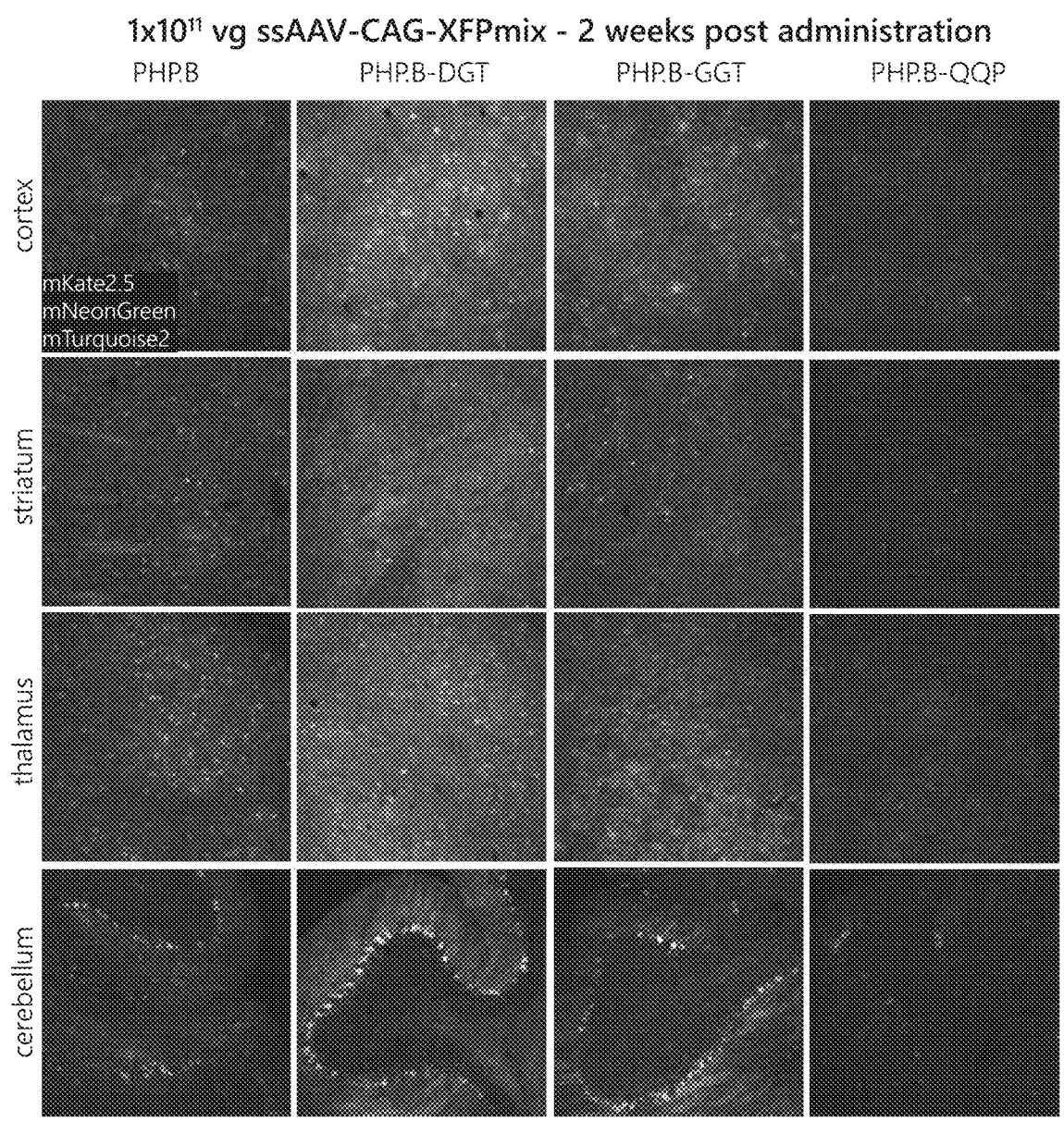
FIG. 16 are images showing reporter expression from AAV-PHP.B variants. Bright spots indicate reporter expression from the AAV-PHP.B variants. Single-plane confocal images of brain sections from mice assessed 2 weeks after IV injection $1 \times 10^{11}$ vg (total)/mouse of AAV-PHP.B or the indicated AAV-PHP.B variant. Each variant was used to package a mix of reporters: ssAAV-CAG-mTurquoise2, mNeonGreen, and mKate 2.5. Note, mKate2.5 appears to aggregate in some cell types, most notably in neurons and endothelial cells.
Figure 17:
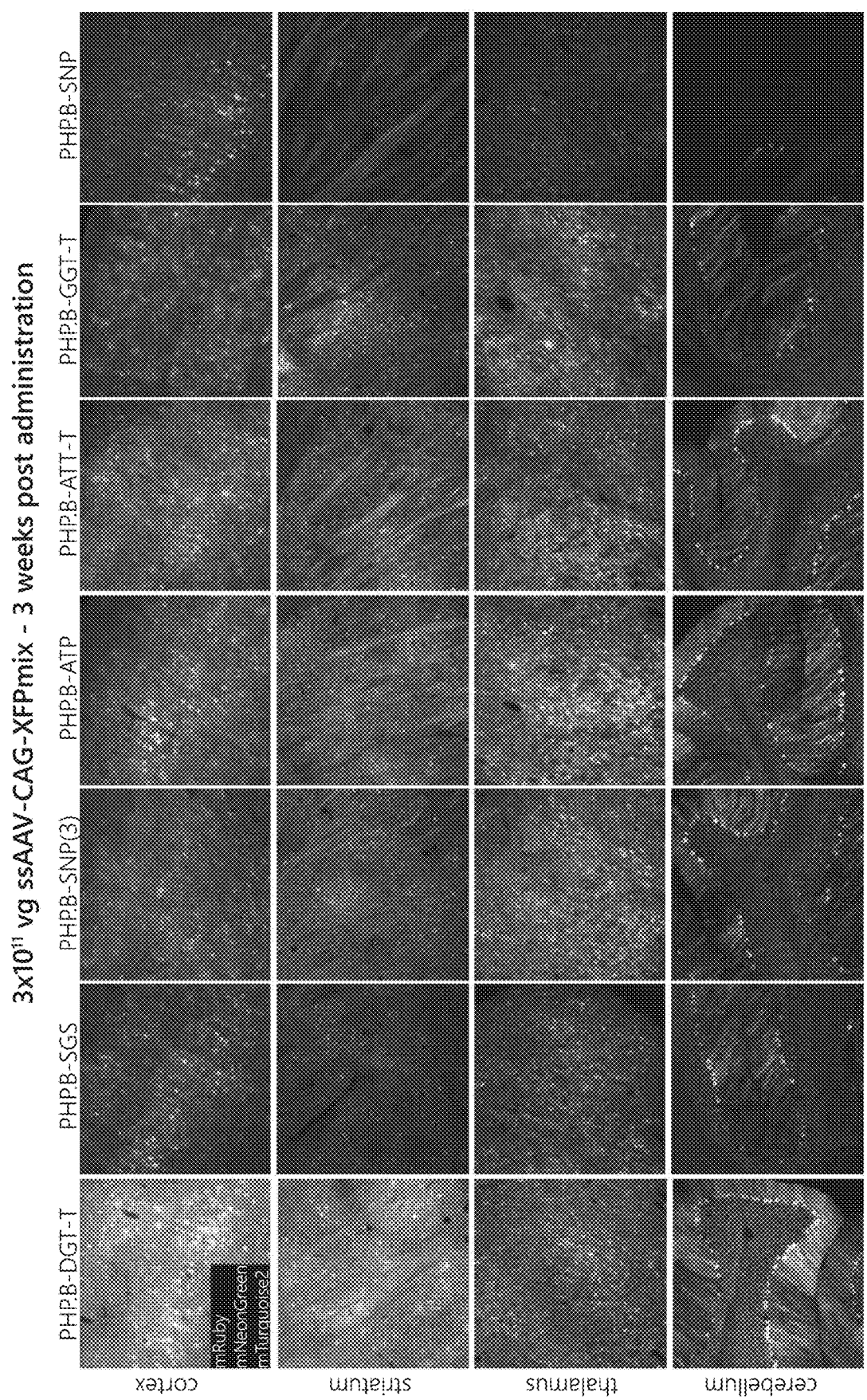
FIG. 17 depicts reporter expression from AAV-PHP.B variants. Bright spots indicate reporter expression from the AAV-PHP.B variants. Single-plane confocal images of brain sections from mice assessed 3 weeks after injection of $3 \times 10^{11}$ vg (total)/mouse of the indicated AAV-PHP.B variant. Each variant was used to package a mix of reporters: ssAAV-CAG-mTurquoise2, mNeonGreen, and mRuby 2.
Figure 18:
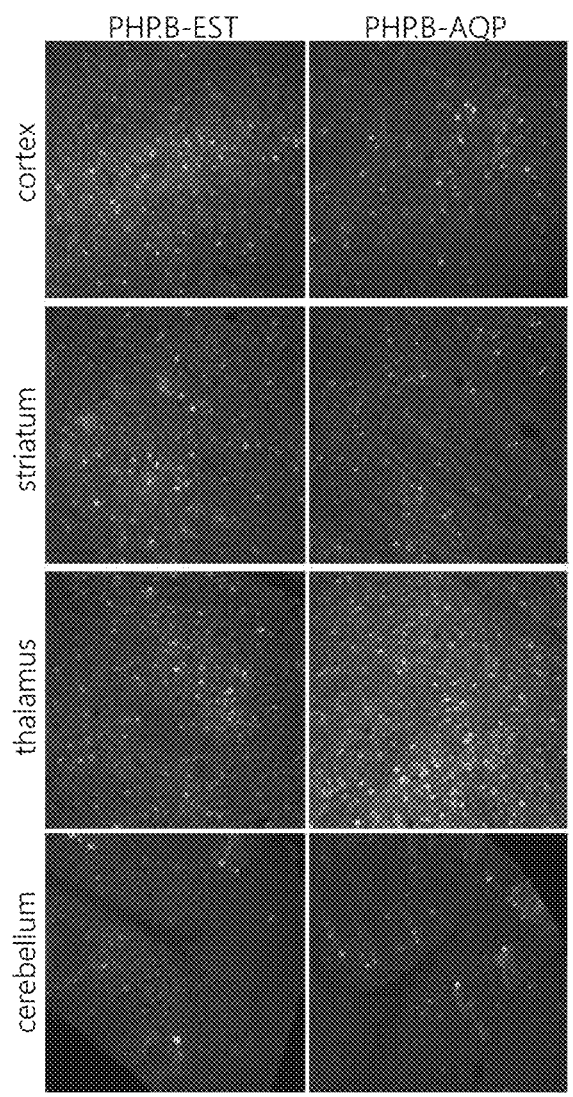
FIG. 18 are images showing reporter expression from AAV-PHP.B variants. Bright spots indicate reporter expression from the AAV-PHP.B variants. Single-plane confocal images of brain sections from mice assessed 11 days after IV injection of $1 \times 10^{11}$ vg (total)/mouse of the indicated AAV-PHP.B variant. Each variant was used to package a mix of reporters: ssAAV-CAG-mTurquoise2, mNeonGreen, and mRuby2.
Figure 23A:
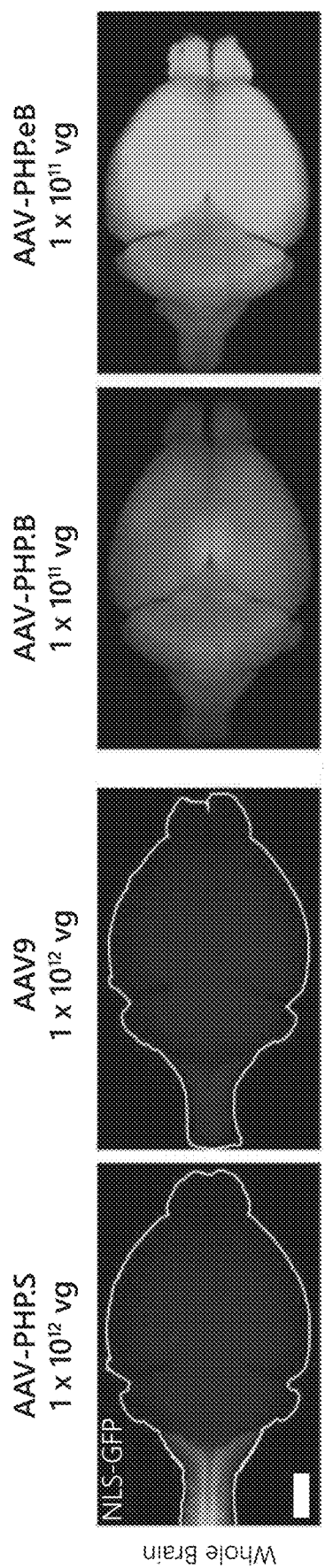
FIGS. 23A-23E show that two AAV capsids, AAV-PHP.S and AAV-PHP.N, efficiently transfer genes to the peripheral and central nervous systems, respectively. Adult mice were intravenously injected with the indicated dose of virus.
Figure 23B:
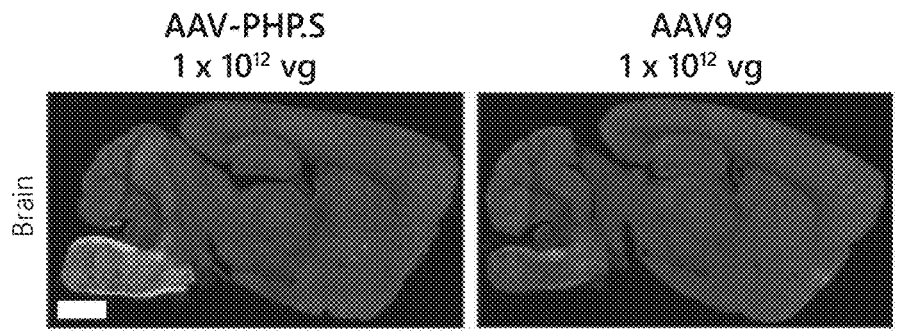
Figure 23C:
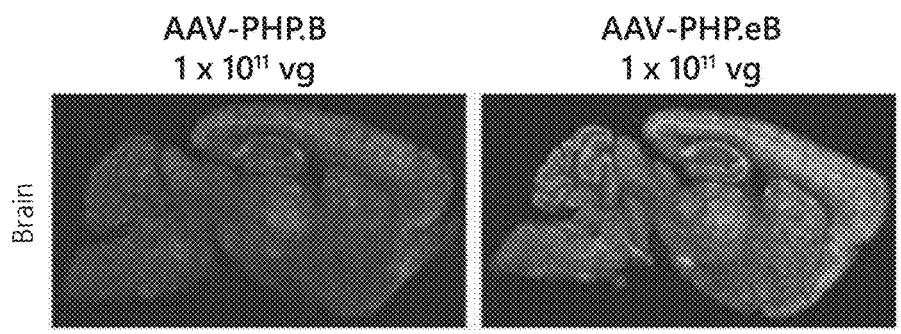
Figure 23D:
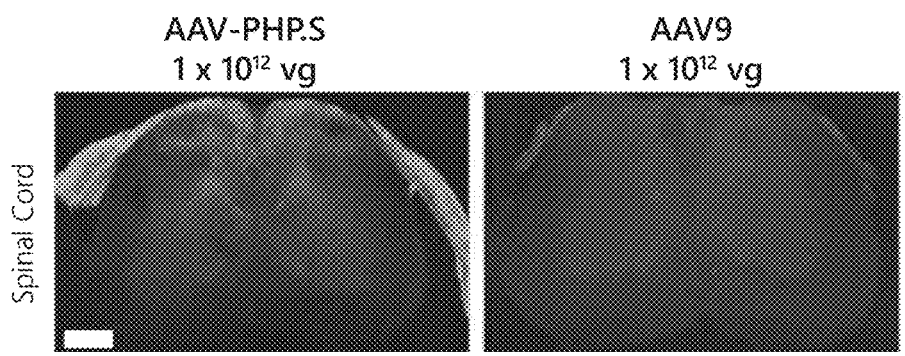
Figure 23E:
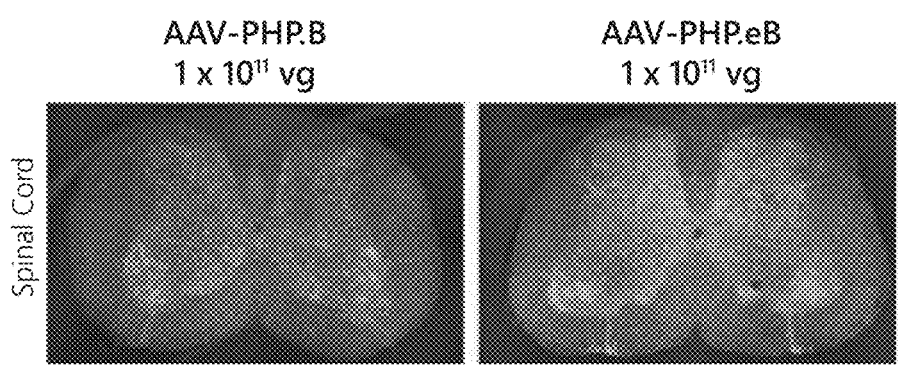

To determine whether AAV-PHP.A and AAV-PHP.B can also transduce human neural cells, these variants were tested on cortical neurons and astrocytes derived from human induced pluripotent stem cells (hiPSCs) using a 3D differtion, significantly more GFP expressing cells were observed along the brain vasculature of mice that received AAV-PHP.B as compared with those that received AAV9 or AAV-PHP.A (FIGS. 14C-14D). Considered together with the transduction characteristics of AAV-PHP.B and AAV-PHP.A in vivo (FIGS. 5A-5G, 6A-6I and 7A-7F) and in human neural cultures (FIGS. 13A-C), these data suggest that while both AAV-PHP vectors more efficiently associate with the brain vasculature, they may differ in subsequent cell type-specific entry or transport step(s).

TABLE 3

| Variant | AA Sequence | Nucleotide Sequence | % of total | in vivo characteristics | production |
|---|---|---|---|---|---|
| AAV-PHP.B | TLAVPFK (SEQ ID NO: 40) | ACTTTGGCGGTGCCT TTTAAG (SEQ ID NO: 74) | 25.00% | Broad CNS transduction | Good |
| AAV-PHP.B2 | SVSKPFL (SEQ ID NO: 41) | AGTGTGAGTAAGCCT TTTTTG (SEQ ID NO: 75) | 11.76% | Broad CNS transduction | Good |
| AAV-PHP.B3 | FTLTTPK (SEQ ID NO: 42) | TTTACGTTGACGACG CCTAAG (SEQ ID NO: 76) | 7.35% | Broad CNS transduction | Good |
| AAV-PHP.A | YTLSQGW (SEQ ID NO: 38) | TATACTTTGTCGCAG GGTTGG (SEQ ID NO: 77) | 40.00% | Increased astrocyte selectivity | Poor |
| G2A12 | QAVRTSL (SEQ ID NO: 37) | CAGGCGGTTAGGACG TCTTTG (SEQ ID NO: 78) | 33.33% | Similar to AAV9 in the brain | Excellent |
| G2A15 | LAKERLS (SEQ ID NO: 39) | CTTGCGAAGGAGCGG CTTTCG (SEQ ID NO: 79) | 20.00% | Similar to AAV9 in the brain | Excellent | entiation method. HiPSC lines from two individuals were differentiated into 3D cerebral cortex-like structures (cortical spheroids), and maintained in vitro for up to 200 days. Aged cortical spheroids contain superficial and deep layer cortical excitatory neurons and up to 20% astrocytes31. In dissociated cortical spheroids that were exposed to the three viruses in monolayer, AAVPHP.B more efficiently transduced both GFAP-expressing astrocytes and MAP2-expressing neurons in comparison with either AAV9 or AAV-PHP.A (FIG. 12; two-way ANOVA p<0.01, n=3). In addition, all three viruses were capable of transducing intact 3D cortical spheroids (FIG. 5C).

In two trials for astrocyte targeting, the variants, AAV-PHP.B, B2, and B3 were identified (FIG. 9). These variants provide broad CNS transduction of both neurons and glia, and AAV-PHP.A that provides selectively more efficient astrocyte transduction. Identification of capsids with distinct properties from the same selection scheme was expected given that the recovery method used selected for astrocyte transduction rather than for any specific intermediate step(s), e.g., brain vascular association, BBB transcytosis or astrocyte binding/internalization. Therefore, capsid variants that are more efficient at any of these intermediate steps should be recovered in the selection process.

Through immunostaining for capsids it was found that the AAV-PHP capsids, unlike the AAV9, readily localized to the brain vasculature shortly after intravenous administration (FIGS. 14A-14B). In addition, by 24 hours post-administra- Using CREATE, new AAV variants were developed that enable efficient widespread gene transfer to the adult mouse CNS after intravenous administration. An important advantage of this system is that it introduces selective pressure for capsids that mediate efficient intracellular trafficking and conversion of the single-stranded viral genome to persistent double-stranded DNA (dsDNA) forms necessary for long-term transduction (only the dsDNA genomes should serve as substrates for Cre). This additional selective pressure for functional capsids may have contributed to the identification of AAVPHP.A and the AAV-PHP.B variants (disclosed herein) in independent trials after only two rounds of in vivo selection. In comparison, many previous in vivo and in vitro AAV capsid selection methods have applied 3-10 rounds of selection to identify capsid variants with enhanced properties.

Without being bound by any particular theory, it is believed that CREATE can be applied to discover AAV capsid variants that target defined, CRE-expressing cell types in any organ. Thus, it can be used not only in transgenic animals, as shown here, but also to develop AAV variants that target (i) specific Cre+ cell types in spheroid cultures or organoid cultures, (ii) cells made Cre+ in non-transgenic animals by, for example, viral injections that achieve population-, projection33-, or activity-based Cre expression or (iii) Cre+ human cells in human/mouse chimeric animals. Given the reported AAV tropism differences between animal models and humans, selection schemes that use human Cre+ cells in vivo, cell-specific Cre expression in three dimensional hiPSC-derived cellular models, or future Cre transgenic marmosets may be desirable for developing improved vectors for clinical applications. In addition, the success of AAV-based gene therapies, especially those requiring systemic delivery, can be hindered by the presence of neutralizing AAV capsid antibodies in the human population. By using CREATE together with exposure of AAV libraries to pooled human sera, one could envision simultaneously selecting for capsids with retained or enhanced transduction characteristics that are also less susceptible to antibody-mediated neutralization.

CREATE can also be used with next-generation sequencing to better predict the characteristics of the recovered sequences prior to testing the variants individually. Sequencing both the entire pool of variants recovered from the Cre-expressing target cells along with the unselected virus library should enable quantification of the relative extent of enrichment of each recovered sequence. Furthermore, sequencing capsids recovered from multiple Cre-expressing or Cre non-expressing populations could provide a means to perform both positive and negative selection in multiple cell types in a single experiment. Such in vivo-in silico selection approaches should increase the power of CREATE to enhance gene transfer to the CNS and other difficult-to-target cell populations.

Disclosed herein are novel CNS targeting sequences that were developed through use of the CREATE method. In some embodiments, DNA libraries that had 7-mer insertion sequences between amino acids 588-599 of AAV9 capsid protein were made. After creating virus libraries from the DNA libraries, the CREATE method was used to select and recover novel AAV capsid sequences that transduced Cre expressing cells one week after administration. Variants recovered from the selection process are shown in Table 4.

TABLE 4

| Name | AA Sequence | % of clones recovered | Phenotype |
| --- | --- | --- | --- |
| PHP.A | YTLSQGW (SEQ ID NO: 38) | 40.0% | Improved astrocyte transduction, poor virus production, reduced peripheral transduction |
| PHP.S | QAVRTSL (SEQ ID NO: 37) | 33.3% | Improved peripheral neuron and cardiac myocyte transduction, similar to AAV9 within the CNS |
| G2A3 | LAKERLS (SEQ ID NO: 39) | 20.0% | Similar AAV9 Improved CNS transduction, broad transduction |
| PHP.B | TLAVPFK (SEQ ID NO: 40) | 25.0% | Outside the CNS (similar to AAV9) |
| PHP.B2 | SVSKPFL (SEQ ID NO: 41) | 10.0% | Improved CNS transduction |
| PHP.B3 | FTLTTPK (SEQ ID NO: 42) | 7.5% | Improved CNS transduction |

TABLE 4-continued

| Name | AA Sequence | % of clones recovered | Phenotype |
| --- | --- | --- | --- |
| G2B4 | MNSTKNV (SEQ ID NO: 43) | 5.0% | Similar to AAV9 |
| G2B5 | VSGGHHS (SEQ ID NO: 44) | 2.5% | Similar to AAV9 |

CREATE was used to determine transduction of three CNS populations: GFAP-Cre (astrocytes), Vgat-IRES-Cre (GAGAergic neurons) and Vglut2-IRES-Cre (a subset of glutamatergice neurons). After DNA was isolated from the brains and spinal cords, recovered variants were assessed by clonal and/or next generation sequencing after 2 rounds of selection. This approach has led to the identification of vectors that exhibit efficient CNS transduction (see Table 5). A number of identified vectors were found to be more effective in CNS transduction than PHP.B, for example PHP.B-DGT (PHP.N), PHP.B-EST, and PHP.B-ATT-T.

TABLE 5

| Name | AA Sequence | SEQ ID NO. | Observation |
| --- | --- | --- | --- |
| PHP.B-DGT (PHP.N) | DGTLAVPFKAQ | SEQ ID NO: 4 | broad CNS tropism, strong CNS transduction |
| PHP.B-EST | ESTLAVPFKAQ | SEQ ID NO: 5 | strong CNS transduction, especially strong in astrocytes and Purkinje cells |
| PHP.B-GGT | GGTLAVPFKAQ | SEQ ID NO: 6 | Strong CNS transduction |
| PHP.B-ATP | AQTLATPFKAQ | SEQ ID NO: 7 | Strong CNS transduction |
| PHP.B-ATT-T | ATTLATPFKAQ | SEQ ID NO: 8 | strong CNS transduction |
| PHP.B-DGT-T | DGTLATPFKAQ | SEQ ID NO: 9 | Strong CNS transduction |
| PHP.B-GGT-T | GGTLATPFKAQ | SEQ ID NO: 10 | Strong CNS transduction |
| PHP.B-SGS | SGSLAVPFKAQ | SEQ ID NO: 11 | Strong CNS transduction |
| PHP.B-AQP | AQTLAQPFKAQ | SEQ ID NO: 12 | Strong CNS transduction |
| PHP.B-QQP | AQTLQQPFKAQ | SEQ ID NO: 13 | Strong CNS transduction |
| PHP.B-SNP(3) | AQTLSNPFKAQ | SEQ ID NO: 14 | Strong CNS transduction |
| PHP.B-SNP | AQTLAVPFSNP | SEQ ID NO: 15 | Strong CNS tropism with high specificity for neurons |

Example 3

Method of Making Variants of AAV-PHP.B for Efficient Transduction of CNS Neurons and Glia The AAV-PHP.B 7-mer peptide and flanking sequences were further evolved through site saturation mutagenesis of three consecutive amino acids (see FIG. 13). The five saturation libraries (XXX1-XXX5) were generated by PCR, mixed in equal amounts and used to generate DNA. The DNA was used to generate the AAV capsid libraries. Using CREATE, selections were run in parallel for transduction of three CNS populations: GFAP-Cre (astrocytes), Vgat-IRES-Cre (GABAergic neurons) and Vglut2-IRES-Cre (a subset of glutamatergic neurons). DNA was isolated from the brains and spinal cords. Recovered variants were assessed by clonal and/or next generation sequencing after 2 rounds of selection. This approach has led to the identification of additional vectors that exhibit efficient CNS transduction (see Tables 3 and 4). Sequences were chosen for individual validation based on one or more of the following criteria (i) the frequency at which each variant is present after two rounds of selection (sequences present at highter frequencies were likely to have been enriched during the in vivo selection), (ii) the presence of multiple nucleic acid sequence variants encoding the same amino acid sequence, and (iii) observed enrichment as compared to the virus library.

Example 4

Making Variants of AAV-PHP.B

AAV-PHP.B 7-mer (SEQ ID NO: 40) was partially randomized to make corresponding variants through overlapping replacement of 3 amino acids of the 7-mer sequence and the 2 amino acids flanking the 7-mer with random amino acids. An overview of the strategy for making variants of AAV-PHP.B is shown in FIG. 21.

After two rounds of selection, the DGTLAVPFKAQ (SEQ ID NO: 4) sequence was chosen for characterization. The DGTLAVPFKAQ (SEQ ID NO: 4) sequence was independently selected from 2 different amino acid sequences: (i) GAT GGG ACT TTG GCG GTG CCT TTT AAG GCA CAG (SEQ ID NO: 54) and (ii) GAT GGG ACG TTG GCG GTG CCT TTT AAG GCA CAG (SEQ ID NO: 55).

In some embodiments, a 7AA (7-mer) sequence was inserted between the amino acids 588-589 of the AAV9 capsid protein. The AAV-PHP.S 7-mer insertion (SEQ ID NO: 37) has the following 7-mer sequence: QAVRTSL (SEQ ID NO. 37). It was selected from the nucleotide sequence: CAG GCG GTT AGG ACG TCT TTG (SEQ ID NO 56).

Example 5

Characterization of AAV-PHP.N (SEQ ID NO: 46) and AAV-PHP.S (SEQ ID NO: 47)

This example provides additional characterization of two AAV variants, AAV-PHP.N (SEQ ID NO: 46) and AAV-PHP.S (SEQ ID NO: 47). AAV-PHP.N differs from AAV-PHP.B by two amino acid substitutions (A587D and Q588G). AAV-PHP.B capsid exihibited increased efficiency of gene delivery to several CNS neuron populations as compared to AAV-PHP.N capsid, which can enable gene transfer to a greater fraction of cells or high rates of transduction with lower doses of virus.

Figure 24A:
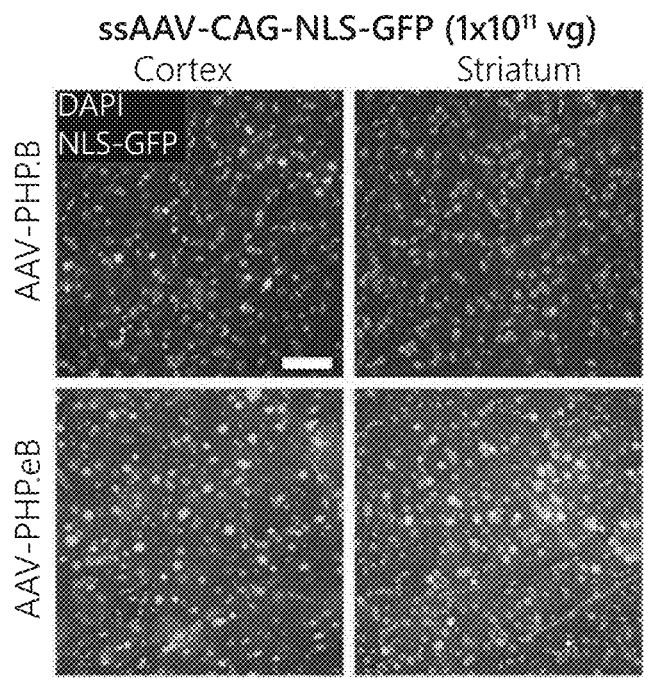
FIGS. 24A-24G show that AAV-PHP.N transduces several neuron populations more efficiently than AAV-PHP.B.
Figures 24B, 24C:
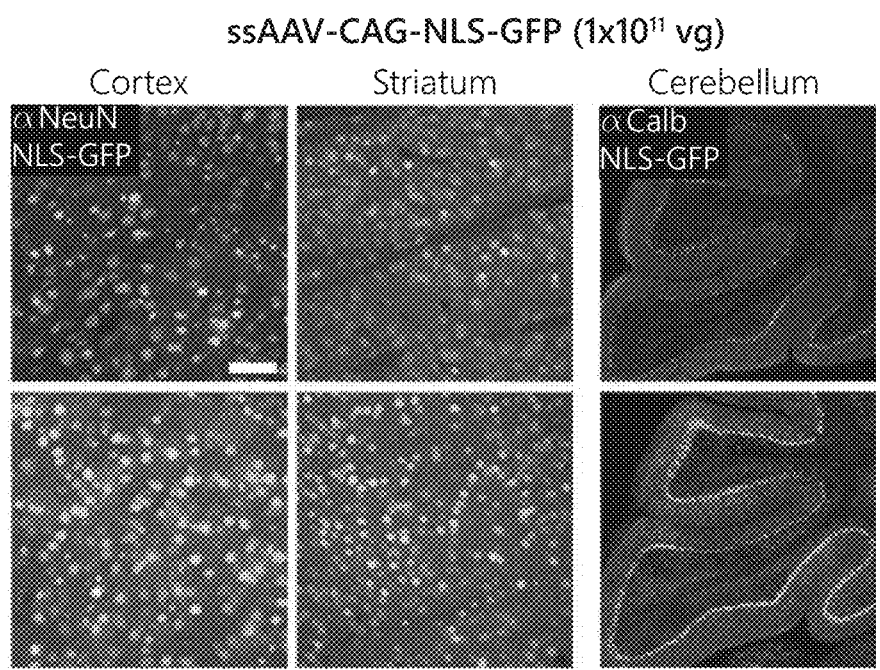
Figures 24D, 24E:
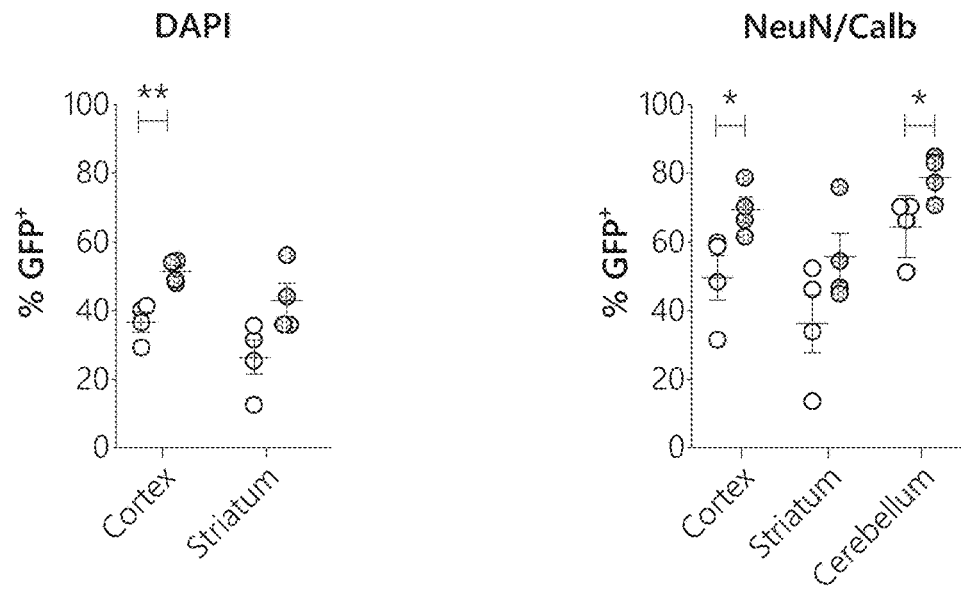
Figures 24F, 24G:
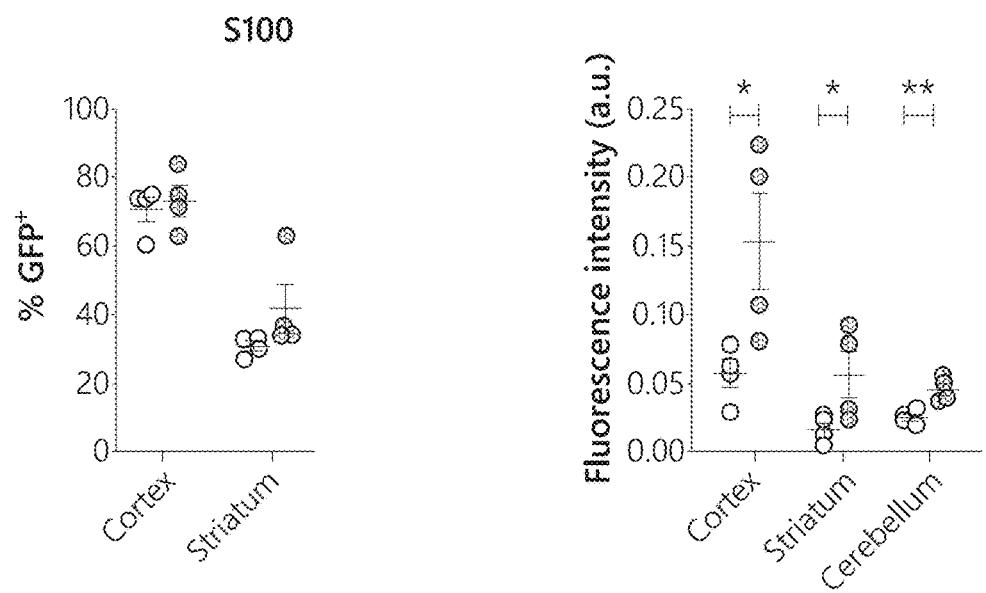
Figure 25A:
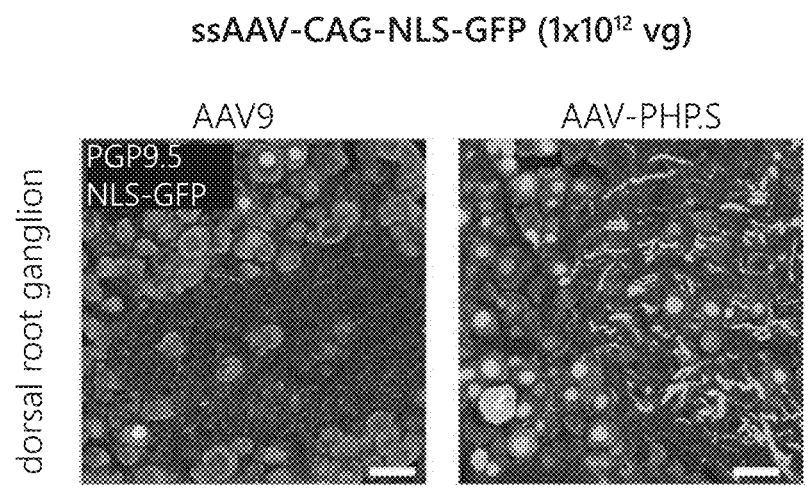
FIGS. 25A-25D show that AAV-PHP.S transduces peripheral sensory neurons more efficiently than AAV9.
Figures 25B, 25C:
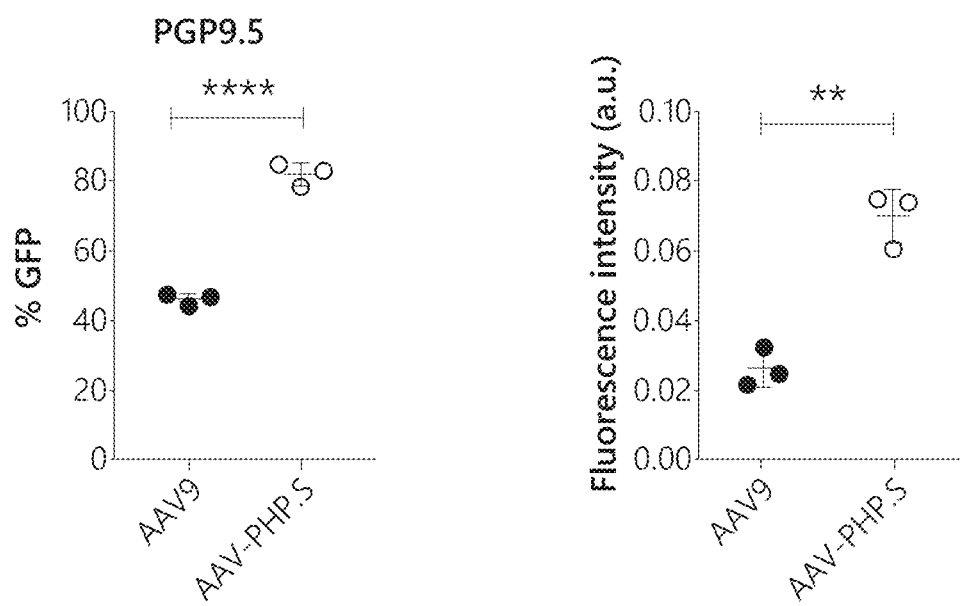
Figure 25D:
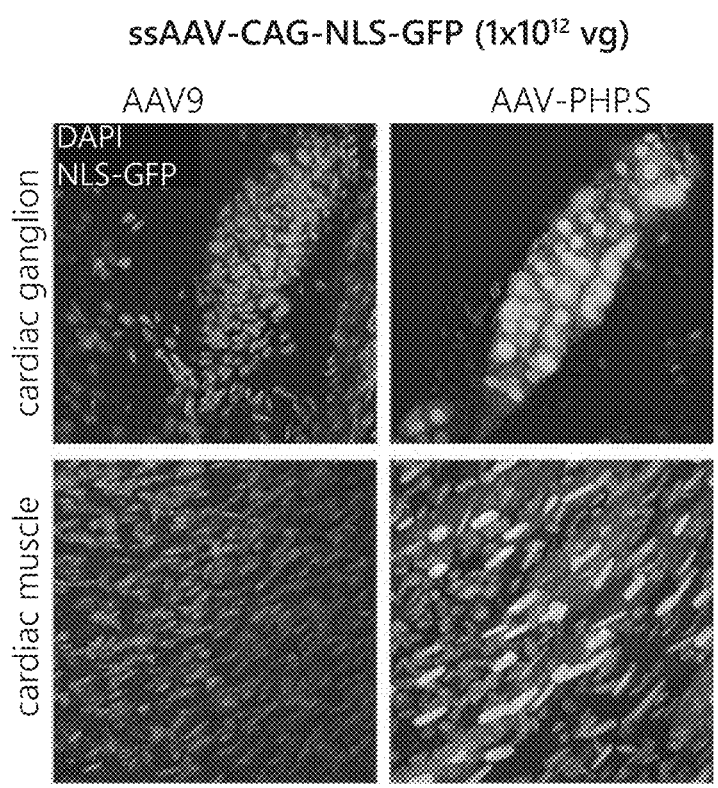

To quantitatively assess the transduction efficiency of AAV-PHP.N (SEQ ID NO: 46) and AAV-PHP.B, young adult mice were intravenously injected with $1\times10^{11}$ vg of single stranded (ss) AAV-CAG-NLS-GFP packaged into either AAV-PHP.N (SEQ ID NO: 46) or AAV-PHP.B (FIGS. 23A-E). Three weeks after administration, the fraction of DAPI$^+$ cells that expressed nuclear localized GFP in the cortex and striatum was assessed. AAV-PHP.N (SEQ ID NO: 46) transduced a significantly greater fraction of DAPI$^+$ cells in the cortex than AAV-PHP.B (FIGS. 24A, 24D). A similar trend was observed in the striatum (p=0.054). Next, the percentage of neurons transduced by each vector in the cortex and striatum (Neun$^+$) and Purkinje neurons in the cerebellum (Calbindin$^+$) (FIGS. 24B, 24E) was determined. AAV-PHP.N provided significantly more efficient transduction of neurons in each region. In further support of the increased efficiency of transduction by AAV-PHP.N as compared with AAV-PHP.B, a significant increase in the per cell GFP fluorescence intensity (mean of the median intensity of GFP fluorescence per nuclei) in the brains of mice that received AAV-PHP.N (SEQ ID NO: 46) (FIG. 24G) was observed.

Example 6

Quantification of Transducition by AAV-PHP.S

The AAV-PHP.S (SEQ ID NO: 47) capsid provides efficient transduction of peripheral sensory neurons in the dorsal root ganglia (DRG) and in the visceral organs including the enteric nervous system. The efficiency of transduction of peripheral neurons with AAV-PHP.S (SEQ ID NO: 47) as compared with AAV9 (SEQ ID NO: 45) was examined. AAV-PHP.S and AAV9 were used to package the same ss AAV-CAG-NLS-GFP genome used above and the viruses were injected intravenously into young adult mice at a dose of $1\times10^{12}$ vg. Three weeks later the percentage of PGP9.5$^+$ DRG neurons transduced by both vectors was determined. In mice that received AAV-PHP.S, a significant increase in both the percentage of the PGP9.5$^+$ cells that expressed nuclear GFP and a significant increase in GFP expression (as measured by fluorescence intensity) per cell was observed. In addition, the mean GFP intensity in cells within cardiac ganglia was also increased relative to AAV9 (FIGS. 24A-G).

Without being bound by any particular theory, it is believed that AAV-PHP.S is useful for studying and treating a variety of diseases and injuries including but not limited to Friedreich's ataxia, heart failure, ischemic heart disease, cardiac hypertrophy, chronic pain, and peripheral nerve injury.

Example 7

Method of Treatment Using Targeting Peptides

A subject having a disorder that can be treated by the application of a nucleic acid to be expressed within a subject is identified. The subject is then administered a first amount of an AAV vector that includes the polynucleotide to be expressed. The polynucleotide encodes for a therapeutic protein. The AAV vector includes a capsid protein that includes a targeting peptide portion comprising, or consisting of, any of SEQ ID NOs: 1-44, 48-53, 65-68, and 74-93, so as to allow proper targeting of the protein to be expressed to the appropriate system within the subject. If needed, the subject is administered a second or third dose of the vector, until a therapeutically effective amount of the protein to be expressed is expressed within the subject in the appropriate system.

Example 8

Method of Treating Huntington's Disease

A subject having Huntington's disease is identified. The subject is then administered a first amount of an AAV vector that includes the polynucleotide to be expressed. The polynucleotide encodes for a therapeutic protein. The AAV vector includes a capsid protein that includes a targeting peptide portion comprised of any of SEQ ID NOs: 1-44, 48-53, 65-68, and 74-93, so as to allow proper targeting of the protein to be expressed to the nervous system within the subject. If needed, the subject is administered a second or third dose of the vector, until a therapeutically effective amount of the protein to be expressed is expressed within the subject in the nervous system.

Example 9

Method of Treating Huntington's Disease

A subject having Huntington's disease is identified. The subject is then administered a first amount of an AAV vector that includes a polynucleotide that encodes for a small non-coding RNA (small hairpin RNA (shRNA) or microRNA (miRNA)) configured to reduce expression of the Huntingtin protein by its sequence). The AAV vector includes a capsid protein that includes a targeting peptide portion comprised of any of SEQ ID NOs: 1-44, 48-53, 65-68, and 74-93, so as to allow proper targeting of the said polynucleotide to the nervous system. If needed, the subject is administered a second or third dose of the vector, until a therapeutically effective amount of the small non-coding RNA is expressed the subject in the nervous system.

Example 10

Method of Treating Huntington's Disease

A subject having Huntington's disease is identified. The subject is then systemically administered a first amount of an AAV vector that includes a polynucleotide that encodes for a Zinc finger protein (ZFP) engineered to represses the transcription of the Huntingtin (HTT) gene. The AAV vector will include a capsid protein that includes a targeting peptide portion comprised of any of SEQ ID NOs: 1-44, 48-53, 65-68, and 74-93, so as to allow proper targeting of the ZFP to the nervous system, among other organs. If needed, the subject is administered a second or third dose of the vector, until a therapeutically effective amount of the ZFP is expressed the subject in the nervous system.

Example 11

Method of Huntington's Disease

A subject having Huntington's disease is identified. The subject is then systemically administered a first amount of an AAV vector that includes a polynucleotide that encodes for a small non-coding RNA (small hairpin RNA (shRNA) or microRNA (miRNA)) designed by one skilled in the art to reduce expression of the Huntingtin protein. The AAV vector will include a capsid protein that includes a targeting peptide portion comprised of any of SEQ ID NOs: 1-44, 48-53, 65-68, and 74-93, so as to allow proper targeting of the polynucleotide to the nervous system, among other organs. If needed, the subject is administered a second or third dose of the vector, until a therapeutically effective amount of the small non-coding RNA is expressed the subject in the nervous system.

Example 12

Method of Treating Alzheimer's Disease

A subject having Alzheimer's disease is identified. The subject is then administered a first amount of an AAV vector that includes a polynucleotide that encodes for an anti-Abeta antibodies or antibody fragments. The AAV vector includes a capsid protein that includes a targeting peptide portion comprised of any of SEQ ID NOs: 1-44, 48-53, 65-68, and 74-93, so as to allow proper targeting of the antibody or antibody fragment to be expressed to the nervous system. If needed, the subject is administered a second or third dose of the vector, until a therapeutically effective amount of the antibody or antibody fragment is expressed the subject in the nervous system.

Example 13

Method of Treating Alzheimer's Disease

A subject having Alzheimer's disease is identified. The subject is then administered a first amount of an AAV vector that includes a polynucleotide that encodes for an apolipoprotein E (ApoE) protein, preferably the human apoE polypeptide apoE2 or modified variant of apoE2. The AAV vector includes a capsid protein that includes a targeting peptide portion comprised of any of SEQ ID NOs: 1-44, 48-53, 65-68, and 74-93, so as to allow proper targeting of the antibody or antibody fragment to be expressed to the nervous system. If needed, the subject is administered a second or third dose of the vector, until a therapeutically effective amount of the ApoE protein is expressed the subject in the nervous system.

Example 14

Method of Treating SMA

A subject having spinal muscular atrophy (SMA) is identified. The subject is then administered a first amount of an AAV vector that includes a polynucleotide that encodes for a survival motor neuron 1 (SMN1) polypeptide. The AAV vector includes a capsid protein that includes a targeting peptide portion comprised of any of SEQ ID NOs: 1-44, 48-53, 65-68, and 74-93, so as to allow proper targeting of the SMN protein to be expressed to the nervous system. If needed, the subject is administered a second or third dose of the vector, until a therapeutically effective amount of the SMN protein is expressed the subject in the nervous system.

Example 15

Method of Treating Friedreich's Ataxia

A subject having Friedreich's ataxia is identified. The subject is then systemically administered a first amount of an AAV vector that includes a polynucleotide that encodes for a frataxin protein. The AAV vector includes a capsid protein that includes a targeting peptide portion comprised of any of SEQ ID NOs: 1-44, 48-53, 65-68, and 74-93, so as to allow proper targeting of the frataxin protein to be expressed to the nervous system and heart, among other organs. If needed, the subject is administered a second or third dose of the vector, until a therapeutically effective amount of the frataxin protein is expressed the subject in the nervous system and heart.

Example 16

Method of Treating Pompe Disease

A subject having Pompe disease is identified. The subject is then systemically administered a first amount of an AAV vector that includes a polynucleotide that encodes for an acid alpha-glucosidase (GAA) protein. The AAV vector includes a capsid protein that includes a targeting peptide portion comprised of any of SEQ ID NOs: 1-44, 48-53, 65-68, and 74-93, so as to allow proper targeting of the GAA protein to be expressed to the nervous system and heart, among other organs. If needed, the subject is administered a second or third dose of the vector, until a therapeutically effective amount of the GAA protein is expressed the subject in the nervous system and heart.

Example 17

Method of Treating Late Infantile Neuronal Ceroid Lipofuscinosis

A subject having Late Infantile neuronal ceroid lipofuscinosis (LINCL) is identified. The subject is then systemically administered a first amount of an AAV vector that includes a CLN2 polynucleotide that encodes for the tripeptidyl peptidase 1 protein. The vector includes a capsid protein that includes a targeting peptide portion comprised of any of SEQ ID NOs: 1-44, 48-53, 65-68, and 74-93, so as to allow proper targeting of the tripeptidyl peptidase 1 protein to be expressed to the nervous system. If needed, the subject is administered a second or third dose of the vector, until a therapeutically effective amount of the tripeptidyl peptidase 1 protein is expressed the subject in the nervous system.

Example 18

Method of Treating Batten Disease

A subject having the Juvenile NCL form of Batten disease is identified. The subject is then systemically administered a first amount of an AAV vector that includes a CLN3 polynucleotide that encodes for the battenin protein. The AAV vector includes a capsid protein that includes a targeting peptide portion comprised of any of SEQ ID NOs: 1-44, 48-53, 65-68, and 74-93, so as to allow proper targeting of the battenin protein to be expressed to the nervous system. If needed, the subject is administered a second or third dose of the vector, until a therapeutically effective amount of the battenin protein is expressed the subject in the nervous system.

Example 19

Method of Treating Canavan Disease

A subject having Canavan disease is identified. The subject is then systemically administered a first amount of an AAV vector that includes an ASPA polynucleotide that encodes for the aspartoacylase protein. The AAV vector includes a capsid protein that includes a targeting peptide portion comprised of any of SEQ ID NOs: 1-44, 48-53, 65-68, and 74-93, so as to allow proper targeting of the aspartoacylase protein to be expressed to the nervous system. If needed, the subject is administered a second or third dose of the vector, until a therapeutically effective amount of the aspartoacylase protein is expressed the subject in the nervous system.

Example 20

Method of Treating Parkinson's Disease

A subject having Parkinson's disease is identified. The subject is then systemically administered a first amount of one or more v AAV ectors that each includes one or more polynucleotide(s) that encode an enzyme(s) necessary for the increased production of dopamine from non-dopaminergic cells. The AAV vector includes a capsid protein that includes a targeting peptide portion comprised of any of SEQ ID NOs: 1-44, 48-53, 65-68, and 74-93, so as to allow proper targeting of said enzyme(s) to be expressed to the nervous system. If needed, the subject is administered a second or third dose of the vector, until a therapeutically effective amount of the enzyme(s) is expressed the subject in the nervous system.

Example 21

Method of Treating Parkinson's Disease

A subject having Parkinson's disease is identified. The subject is then systemically administered a first amount of an AAV vector that includes a polynucleotide that encode a modified, aggregation-resistant form of alpha-synuclein protein that reduces the aggregation of endogenous alpha-synuclein. The AAV vector includes a capsid protein that includes a targeting peptide portion comprised of any of SEQ ID NOs: 1-44, 48-53, 65-68, and 74-93, so as to allow proper targeting of the aggregation-resistant alpha-synuclein protein to be expressed to the nervous system. If needed, the subject is administered a second or third dose of the vector, until a therapeutically effective amount of the protein is expressed the subject in the nervous system.

Example 22

Method of Treating Amyotrophic Lateral Sclerosis or Frontal Dementia

A subject having amyotrophic lateral sclerosis or frontal dementia caused by a mutation in C9ORF72 is identified. The subject is then administered a first amount of an AAV vector that includes a polynucleotide that encodes a non-coding RNA(s) that reduce nuclear RNA foci caused by the hexanucleotide expansion (GGGGCC) in the subjects cells. The AAV vector includes a capsid protein that includes a targeting peptide portion comprised of any of SEQ ID NOs: 1-44, 48-53, 65-68, and 74-93, so as to allow proper targeting of the RNA(s) to be expressed to the nervous system. If needed, the subject is administered a second or third dose of the vector, until a therapeutically effective amount of the RNA(s) is expressed the subject in the nervous system.

Example 23

Method of Treating Multiple Sclerosis

A subject having multiple sclerosis is identified. The subject is then systemically administered a first amount of an AAV vector that includes a polynucleotide that encode a trophic or immunomodulatory factor, for example leukemia inhibitory factor (LIF) or ciliary eurotrophic factor (CNTF). The AAV vector includes a capsid protein that includes a targeting peptide protion comprised of any of SEQ ID NOs: 1-44, 48-53, 65-68, and 74-93, so as to allow proper targeting of the said factor to be expressed to the nervous system. If needed, the subject is administered a second or third dose of the vector, until a therapeutically effective amount of the factor is expressed the subject in the nervous system.

Example 24

Method of Treating Amyotrophic Lateral Sclerosis

A subject having amyotrophic lateral sclerosis caused by SOD1 mutation is identified. The subject is then administered a first amount of an AAV vector that includes a polynucleotide that encodes for a small non-coding RNA (small hairpin RNA (shRNA) or microRNA (miRNA)) designed by one of skill in the art to reduce expression of mutant SOD1 protein. The AAV vector includes a capsid protein that includes a targeting peptide portion comprised of any of SEQ ID NOs: 1-44, 48-53, 65-68, and 74-93, so as to allow proper targeting of the small non-coding RNA to be expressed to the nervous system. If needed, the subject is administered a second or third dose of the vector, until a therapeutically effective amount of the small non-coding RNA is expressed the subject in the nervous system.

All references cited herein, including patents, patent applications, papers, text books, and the like, and the references cited therein, to the extent that they are not already, are hereby incorporated herein by reference in their entirety. To the extent that any of the definitions or terms provided in the references incorporated by reference differ from the terms and discussion provided herein, the present terms and definitions control.

The foregoing written specification is considered to be sufficient to enable one skilled in the art to practice the invention. The foregoing description and examples detail certain preferred embodiments of the invention and describe the best mode contemplated by the inventors. It will be appreciated, however, that no matter how detailed the foregoing may appear in text, the invention may be practiced in many ways and the invention should be construed in accordance with the appended claims and any equivalents thereof.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc.

As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A central nervous system (CNS)-targeting adeno-associated virus (AAV) peptide comprising the amino acid sequence of DGTLAVPFKAQ (SEQ ID NO: 4).

2. A recombinant adeno-associated virus (rAAV) comprising an AAV capsid which comprises the CNS-targeting AAV peptide of claim 1; wherein the sequence of DGTLAVPFKAQ (SEQ ID NO: 4) is inserted between AA586 and AA591 of the AAV capsid protein sequence of SEQ ID NO: 45.

3. The rAAV of claim 2, wherein the rAAV comprises an rAAV vector genome.

4. A pharmaceutical composition, comprising the rAAV of claim 3 and one or more pharmaceutical acceptable carriers.

5. An adeno-associated virus (AAV) capsid protein comprising a CNS-targeting peptide that comprises the amino acid sequence of DGTLAVPFKAQ (SEQ ID NO: 4),
   wherein the amino acid sequence of DGTLAVPFKAQ (SEQ ID NO: 4) is inserted between AA586 and AA591 of the AAV capsid protein sequence of SEQ ID NO: 45.

6. A pharmaceutical composition, comprising the rAAV of claim 2 and one or more pharmaceutically acceptable carriers.

* * * * *

SEQUENCE LISTING

```
<160> NUMBER OF SEQ ID NOS: 93

<210> SEQ ID NO 1
<211> LENGTH: 11
<212> TYPE: PRT
<213> ORGANISM: Artificial Sequence
<220> FEATURE:
<223> OTHER INFORMATION: PHP.B

<400> SEQUENCE: 1

Ala Gln Thr Leu Ala Val Pro Phe Lys Ala Gln
1               5                   10

<210> SEQ ID NO 2
<211> LENGTH: 11
<212> TYPE: PRT
<213> ORGANISM: Artificial Sequence
<220> FEATURE:
<223> OTHER INFORMATION: PHP.B2

<400> SEQUENCE: 2

Ala Gln Ser Val Ser Lys Pro Phe Leu Ala Gln
1               5                   10

<210> SEQ ID NO 3
<211> LENGTH: 11
<212> TYPE: PRT
<213> ORGANISM: Artificial Sequence
<220> FEATURE:
<223> OTHER INFORMATION: PHP.B3

<400> SEQUENCE: 3

Ala Gln Phe Thr Leu Thr Thr Pro Lys Ala Gln
1               5                   10

<210> SEQ ID NO 4
<211> LENGTH: 11
<212> TYPE: PRT
<213> ORGANISM: Artificial Sequence
<220> FEATURE:
<223> OTHER INFORMATION: PHP.N/PHP.B-DGT

<400> SEQUENCE: 4

Asp Gly Thr Leu Ala Val Pro Phe Lys Ala Gln
1               5                   10

<210> SEQ ID NO 5
<211> LENGTH: 11
<212> TYPE: PRT
<213> ORGANISM: Artificial Sequence
<220> FEATURE:
<223> OTHER INFORMATION: PHP.B-EST

<400> SEQUENCE: 5

Glu Ser Thr Leu Ala Val Pro Phe Lys Ala Gln
1               5                   10
```

```
<210> SEQ ID NO 6
<211> LENGTH: 11
<212> TYPE: PRT
<213> ORGANISM: Artificial Sequence
<220> FEATURE:
<223> OTHER INFORMATION: PHP.B-GGT

<400> SEQUENCE: 6

Gly Gly Thr Leu Ala Val Pro Phe Lys Ala Gln
1               5                   10

<210> SEQ ID NO 7
<211> LENGTH: 11
<212> TYPE: PRT
<213> ORGANISM: Artificial Sequence
<220> FEATURE:
<223> OTHER INFORMATION: PHP.B-ATP

<400> SEQUENCE: 7

Ala Gln Thr Leu Ala Thr Pro Phe Lys Ala Gln
1               5                   10

<210> SEQ ID NO 8
<211> LENGTH: 11
<212> TYPE: PRT
<213> ORGANISM: Artificial Sequence
<220> FEATURE:
<223> OTHER INFORMATION: PHP.B-ATT-T

<400> SEQUENCE: 8

Ala Thr Thr Leu Ala Thr Pro Phe Lys Ala Gln
1               5                   10

<210> SEQ ID NO 9
<211> LENGTH: 11
<212> TYPE: PRT
<213> ORGANISM: Artificial Sequence
<220> FEATURE:
<223> OTHER INFORMATION: PHP.B-DGT-T

<400> SEQUENCE: 9

Asp Gly Thr Leu Ala Thr Pro Phe Lys Ala Gln
1               5                   10

<210> SEQ ID NO 10
<211> LENGTH: 11
<212> TYPE: PRT
<213> ORGANISM: Artificial Sequence
<220> FEATURE:
<223> OTHER INFORMATION: PHP.B-GGT-T

<400> SEQUENCE: 10

Gly Gly Thr Leu Ala Thr Pro Phe Lys Ala Gln
1               5                   10

<210> SEQ ID NO 11
<211> LENGTH: 11
<212> TYPE: PRT
<213> ORGANISM: Artificial Sequence
<220> FEATURE:
<223> OTHER INFORMATION: PHP.B-SGS

<400> SEQUENCE: 11

Ser Gly Ser Leu Ala Val Pro Phe Lys Ala Gln
1               5                   10
```

```
<210> SEQ ID NO 12
<211> LENGTH: 11
<212> TYPE: PRT
<213> ORGANISM: Artificial Sequence
<220> FEATURE:
<223> OTHER INFORMATION: PHP.B-AQP

<400> SEQUENCE: 12

Ala Gln Thr Leu Ala Gln Pro Phe Lys Ala Gln
1               5                   10

<210> SEQ ID NO 13
<211> LENGTH: 11
<212> TYPE: PRT
<213> ORGANISM: Artificial Sequence
<220> FEATURE:
<223> OTHER INFORMATION: PHP.B-QQP

<400> SEQUENCE: 13

Ala Gln Thr Leu Gln Gln Pro Phe Lys Ala Gln
1               5                   10

<210> SEQ ID NO 14
<211> LENGTH: 11
<212> TYPE: PRT
<213> ORGANISM: Artificial Sequence
<220> FEATURE:
<223> OTHER INFORMATION: PHP.B-SNP(3)

<400> SEQUENCE: 14

Ala Gln Thr Leu Ser Asn Pro Phe Lys Ala Gln
1               5                   10

<210> SEQ ID NO 15
<211> LENGTH: 11
<212> TYPE: PRT
<213> ORGANISM: Artificial Sequence
<220> FEATURE:
<223> OTHER INFORMATION: PHP.B-SNP

<400> SEQUENCE: 15

Ala Gln Thr Leu Ala Val Pro Phe Ser Asn Pro
1               5                   10

<210> SEQ ID NO 16
<211> LENGTH: 11
<212> TYPE: PRT
<213> ORGANISM: Artificial Sequence
<220> FEATURE:
<223> OTHER INFORMATION: PHP.B-QGT

<400> SEQUENCE: 16

Gln Gly Thr Leu Ala Val Pro Phe Lys Ala Gln
1               5                   10

<210> SEQ ID NO 17
<211> LENGTH: 11
<212> TYPE: PRT
<213> ORGANISM: Artificial Sequence
<220> FEATURE:
<223> OTHER INFORMATION: PHP.B-NQT

<400> SEQUENCE: 17

Asn Gln Thr Leu Ala Val Pro Phe Lys Ala Gln
1               5                   10

<210> SEQ ID NO 18
```

```
<211> LENGTH: 11
<212> TYPE: PRT
<213> ORGANISM: Artificial Sequence
<220> FEATURE:
<223> OTHER INFORMATION: PHP.B-EGS

<400> SEQUENCE: 18

Glu Gly Ser Leu Ala Val Pro Phe Lys Ala Gln
1               5                   10

<210> SEQ ID NO 19
<211> LENGTH: 11
<212> TYPE: PRT
<213> ORGANISM: Artificial Sequence
<220> FEATURE:
<223> OTHER INFORMATION: PHP.B-SGN

<400> SEQUENCE: 19

Ser Gly Asn Leu Ala Val Pro Phe Lys Ala Gln
1               5                   10

<210> SEQ ID NO 20
<211> LENGTH: 11
<212> TYPE: PRT
<213> ORGANISM: Artificial Sequence
<220> FEATURE:
<223> OTHER INFORMATION: PHP.B-EGT

<400> SEQUENCE: 20

Glu Gly Thr Leu Ala Val Pro Phe Lys Ala Gln
1               5                   10

<210> SEQ ID NO 21
<211> LENGTH: 11
<212> TYPE: PRT
<213> ORGANISM: Artificial Sequence
<220> FEATURE:
<223> OTHER INFORMATION: PHP.B-DST

<400> SEQUENCE: 21

Asp Ser Thr Leu Ala Val Pro Phe Lys Ala Gln
1               5                   10

<210> SEQ ID NO 22
<211> LENGTH: 11
<212> TYPE: PRT
<213> ORGANISM: Artificial Sequence
<220> FEATURE:
<223> OTHER INFORMATION: PHP.B-DST

<400> SEQUENCE: 22

Ala Val Thr Leu Ala Val Pro Phe Lys Ala Gln
1               5                   10

<210> SEQ ID NO 23
<211> LENGTH: 11
<212> TYPE: PRT
<213> ORGANISM: Artificial Sequence
<220> FEATURE:
<223> OTHER INFORMATION: PHP.B-STP

<400> SEQUENCE: 23

Ala Gln Thr Leu Ser Thr Pro Phe Lys Ala Gln
1               5                   10

<210> SEQ ID NO 24
<211> LENGTH: 11
```

```
<212> TYPE: PRT
<213> ORGANISM: Artificial Sequence
<220> FEATURE:
<223> OTHER INFORMATION: PHP.B-PQP

<400> SEQUENCE: 24

Ala Gln Thr Leu Pro Gln Pro Phe Lys Ala Gln
1               5                   10

<210> SEQ ID NO 25
<211> LENGTH: 11
<212> TYPE: PRT
<213> ORGANISM: Artificial Sequence
<220> FEATURE:
<223> OTHER INFORMATION: PHP.B-SQP

<400> SEQUENCE: 25

Ala Gln Thr Leu Ser Gln Pro Phe Lys Ala Gln
1               5                   10

<210> SEQ ID NO 26
<211> LENGTH: 11
<212> TYPE: PRT
<213> ORGANISM: Artificial Sequence
<220> FEATURE:
<223> OTHER INFORMATION: PHP.B-QLP

<400> SEQUENCE: 26

Ala Gln Thr Leu Gln Leu Pro Phe Lys Ala Gln
1               5                   10

<210> SEQ ID NO 27
<211> LENGTH: 11
<212> TYPE: PRT
<213> ORGANISM: Artificial Sequence
<220> FEATURE:
<223> OTHER INFORMATION: PHP.B-TMP

<400> SEQUENCE: 27

Ala Gln Thr Leu Thr Met Pro Phe Lys Ala Gln
1               5                   10

<210> SEQ ID NO 28
<211> LENGTH: 11
<212> TYPE: PRT
<213> ORGANISM: Artificial Sequence
<220> FEATURE:
<223> OTHER INFORMATION: PHP.B-TTP

<400> SEQUENCE: 28

Ala Gln Thr Leu Thr Thr Pro Phe Lys Ala Gln
1               5                   10

<210> SEQ ID NO 29
<211> LENGTH: 11
<212> TYPE: PRT
<213> ORGANISM: Artificial Sequence
<220> FEATURE:
<223> OTHER INFORMATION: PHP.A

<400> SEQUENCE: 29

Ala Gln Tyr Thr Leu Ser Gln Gly Trp Ala Gln
1               5                   10

<210> SEQ ID NO 30
<211> LENGTH: 11
<212> TYPE: PRT
```

<213> ORGANISM: Artificial Sequence
<220> FEATURE:
<223> OTHER INFORMATION: Synthetic amino acid sequence

<400> SEQUENCE: 30

Ala Gln Met Asn Ala Thr Lys Asn Val Ala Gln
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Synthetic amino acid sequence

<400> SEQUENCE: 31

Ala Gln Val Ser Gly Gly His His Ser Ala Gln
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic amino acid sequence

<400> SEQUENCE: 32

Ala Gln Thr Leu Pro Gln Pro Phe Lys Ala Gln
1               5                   10

<210> SEQ ID NO 33
<211> LENGTH: 11
<212> TYPE: PRT
<213> ORGANISM: Artificial Sequence
<220> FEATURE:
<223> OTHER INFORMATION: PHP.B-ATP

<400> SEQUENCE: 33

Ala Gln Thr Leu Ala Thr Pro Phe Lys Ala Gln
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Synthetic amino acid sequence

<400> SEQUENCE: 34

Ala Gln Thr Leu Thr Met Pro Phe Lys Ala Gln
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Synthetic amino acid sequence

<400> SEQUENCE: 35

Ala Gln Thr Leu Thr Met Pro Phe Lys Ala Gln
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Synthetic amino acid sequence

<400> SEQUENCE: 36

Ala Gln Thr Leu Ser Lys Pro Phe Lys Ala Gln
1               5                   10

<210> SEQ ID NO 37
<211> LENGTH: 7
<212> TYPE: PRT
<213> ORGANISM: Artificial Sequence
<220> FEATURE:
<223> OTHER INFORMATION: AAV-PHP.S

<400> SEQUENCE: 37

Gln Ala Val Arg Thr Ser Leu
1               5

<210> SEQ ID NO 38
<211> LENGTH: 7
<212> TYPE: PRT
<213> ORGANISM: Artificial Sequence
<220> FEATURE:
<223> OTHER INFORMATION: PHP.A

<400> SEQUENCE: 38

Tyr Thr Leu Ser Gln Gly Trp
1               5

<210> SEQ ID NO 39
<211> LENGTH: 7
<212> TYPE: PRT
<213> ORGANISM: Artificial Sequence
<220> FEATURE:
<223> OTHER INFORMATION: G2A3

<400> SEQUENCE: 39

Leu Ala Lys Glu Arg Leu Ser
1               5

<210> SEQ ID NO 40
<211> LENGTH: 7
<212> TYPE: PRT
<213> ORGANISM: Artificial Sequence
<220> FEATURE:
<223> OTHER INFORMATION: PHP.B

<400> SEQUENCE: 40

Thr Leu Ala Val Pro Phe Lys
1               5

<210> SEQ ID NO 41
<211> LENGTH: 7
<212> TYPE: PRT
<213> ORGANISM: Artificial Sequence
<220> FEATURE:
<223> OTHER INFORMATION: PHP.B2

<400> SEQUENCE: 41

Ser Val Ser Lys Pro Phe Leu
1               5

<210> SEQ ID NO 42
<211> LENGTH: 7
<212> TYPE: PRT
<213> ORGANISM: Artificial Sequence
<220> FEATURE:

```
<223> OTHER INFORMATION: PHP.B3

<400> SEQUENCE: 42

Phe Thr Leu Thr Thr Pro Lys
1               5

<210> SEQ ID NO 43
<211> LENGTH: 7
<212> TYPE: PRT
<213> ORGANISM: Artificial Sequence
<220> FEATURE:
<223> OTHER INFORMATION: G2B4

<400> SEQUENCE: 43

Met Asn Ser Thr Lys Asn Val
1               5

<210> SEQ ID NO 44
<211> LENGTH: 7
<212> TYPE: PRT
<213> ORGANISM: Artificial Sequence
<220> FEATURE:
<223> OTHER INFORMATION: G2B5

<400> SEQUENCE: 44

Val Ser Gly Gly His His Ser
1               5

<210> SEQ ID NO 45
<211> LENGTH: 736
<212> TYPE: PRT
<213> ORGANISM: Artificial Sequence
<220> FEATURE:
<223> OTHER INFORMATION: AAV9 Capsid Sequence

<400> SEQUENCE: 45

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190
```

```
Ala Ala Pro Ser Gly Val Gly Ser Leu Thr Met Ala Ser Gly Gly
            195                 200                 205
Ala Pro Val Ala Asp Asn Asn Glu Gly Ala Asp Gly Val Gly Ser Ser
    210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Gly Gly Ser Ser Asn Asp Asn
            260                 265                 270
Ala Tyr Phe Gly Tyr Ser Thr Pro Trp Gly Tyr Phe Asp Phe Asn Arg
    275                 280                 285
Phe His Cys His Phe Ser Pro Arg Asp Trp Gln Arg Leu Ile Asn Asn
    290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
            340                 345                 350
Pro Tyr Val Leu Gly Ser Ala His Glu Gly Cys Leu Pro Pro Phe Pro
    355                 360                 365
Ala Asp Val Phe Met Ile Pro Gln Tyr Gly Tyr Leu Thr Leu Asn Asp
    370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
    435                 440                 445
Arg Thr Ile Asn Gly Ser Gly Gln Asn Gln Gln Thr Leu Lys Phe Ser
    450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
            500                 505                 510
Gly Arg Asn Ser Leu Met Asn Pro Gly Pro Ala Met Ala Ser His Lys
    515                 520                 525
Glu Gly Glu Asp Arg Phe Phe Pro Leu Ser Gly Ser Leu Ile Phe Gly
    530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
Tyr Gly Gln Val Ala Thr Asn His Gln Ser Ala Gln Ala Gln Ala Gln
            580                 585                 590
Thr Gly Trp Val Gln Asn Gln Gly Ile Leu Pro Gly Met Val Trp Gln
    595                 600                 605
Asp Arg Asp Val Tyr Leu Gln Gly Pro Ile Trp Ala Lys Ile Pro His
```

```
                    610                 615                 620
Thr Asp Gly Asn Phe His Pro Ser Pro Leu Met Gly Phe Gly Met
625                 630                 635                 640

Lys His Pro Pro Gln Ile Leu Ile Lys Asn Thr Pro Val Pro Ala
                    645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 46
<211> LENGTH: 743
<212> TYPE: PRT
<213> ORGANISM: Artificial Sequence
<220> FEATURE:
<223> OTHER INFORMATION: AAV-PHP.N VP1 Capsid Sequence

<400> SEQUENCE: 46

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
        210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
```

-continued

```
                    245                 250                 255
Tyr Lys Gln Ile Ser Asn Ser Thr Ser Gly Ser Ser Asn Asp Asn
                260                 265                 270

Ala Tyr Phe Gly Tyr Ser Thr Pro Trp Gly Tyr Phe Asp Phe Asn Arg
                275                 280                 285

Phe His Cys His Phe Ser Pro Arg Asp Trp Gln Arg Leu Ile Asn Asn
                290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Pro Phe Pro
                355                 360                 365

Ala Asp Val Phe Met Ile Pro Gln Tyr Gly Tyr Leu Thr Leu Asn Asp
                370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
                435                 440                 445

Arg Thr Ile Asn Gly Ser Gly Gln Asn Gln Gln Thr Leu Lys Phe Ser
                450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
                515                 520                 525

Glu Gly Glu Asp Arg Phe Phe Pro Leu Ser Gly Ser Leu Ile Phe Gly
                530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Asp Gly Thr Leu Ala Val
                580                 585                 590

Pro Phe Lys Ala Gln Ala Gln Thr Gly Trp Val Gln Asn Gln Gly Ile
                595                 600                 605

Leu Pro Gly Met Val Trp Gln Asp Arg Asp Val Tyr Leu Gln Gly Pro
                610                 615                 620

Ile Trp Ala Lys Ile Pro His Thr Asp Gly Asn Phe His Pro Ser Pro
625                 630                 635                 640

Leu Met Gly Gly Phe Gly Met Lys His Pro Pro Gln Ile Leu Ile
                645                 650                 655

Lys Asn Thr Pro Val Pro Ala Asp Pro Pro Thr Ala Phe Asn Lys Asp
                660                 665                 670
```

```
Lys Leu Asn Ser Phe Ile Thr Gln Tyr Ser Thr Gly Gln Val Ser Val
            675                 680                 685

Glu Ile Glu Trp Glu Leu Gln Lys Glu Asn Ser Lys Arg Trp Asn Pro
690                 695                 700

Glu Ile Gln Tyr Thr Ser Asn Tyr Tyr Lys Ser Asn Asn Val Glu Phe
705                 710                 715                 720

Ala Val Asn Thr Glu Gly Val Tyr Ser Glu Pro Arg Pro Ile Gly Thr
            725                 730                 735

Arg Tyr Leu Thr Arg Asn Leu
            740

<210> SEQ ID NO 47
<211> LENGTH: 743
<212> TYPE: PRT
<213> ORGANISM: Artificial Sequence
<220> FEATURE:
<223> OTHER INFORMATION: AAV-PHP.S VP1 Capsid Sequence

<400> SEQUENCE: 47

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285
```

-continued

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                    325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                    405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Arg Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                    485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                    565                 570                 575

Tyr Gly Gln Val Ala Thr Asn His Gln Ser Ala Gln Gln Ala Val Arg
                580                 585                 590

Thr Ser Leu Ala Gln Ala Gln Thr Gly Trp Val Gln Asn Gln Gly Ile
            595                 600                 605

Leu Pro Gly Met Val Trp Gln Asp Arg Asp Val Tyr Leu Gln Gly Pro
    610                 615                 620

Ile Trp Ala Lys Ile Pro His Thr Asp Gly Asn Phe His Pro Ser Pro
625                 630                 635                 640

Leu Met Gly Gly Phe Gly Met Lys His Pro Pro Gln Ile Leu Ile
                    645                 650                 655

Lys Asn Thr Pro Val Pro Ala Asp Pro Pro Thr Ala Phe Asn Lys Asp
                660                 665                 670

Lys Leu Asn Ser Phe Ile Thr Gln Tyr Ser Thr Gly Gln Val Ser Val
            675                 680                 685

Glu Ile Glu Trp Glu Leu Gln Lys Glu Asn Ser Lys Arg Trp Asn Pro
    690                 695                 700

```
Glu Ile Gln Tyr Thr Ser Asn Tyr Tyr Lys Ser Asn Asn Val Glu Phe
705                 710                 715                 720

Ala Val Asn Thr Glu Gly Val Tyr Ser Glu Pro Arg Pro Ile Gly Thr
                725                 730                 735

Arg Tyr Leu Thr Arg Asn Leu
            740

<210> SEQ ID NO 48
<211> LENGTH: 14
<212> TYPE: PRT
<213> ORGANISM: Artificial Sequence
<220> FEATURE:
<223> OTHER INFORMATION: Synthetic amino acid sequence

<400> SEQUENCE: 48

Ser Ala Gln Thr Leu Ala Val Pro Phe Lys Ala Gln Ala Gln
1               5                   10

<210> SEQ ID NO 49
<211> LENGTH: 14
<212> TYPE: PRT
<213> ORGANISM: Artificial Sequence
<220> FEATURE:
<223> OTHER INFORMATION: Synthetic amino acid sequence
<220> FEATURE:
<221> NAME/KEY: VARIANT
<222> LOCATION: 2-4
<223> OTHER INFORMATION: Xaa = any amino acid

<400> SEQUENCE: 49

Ser Xaa Xaa Xaa Leu Ala Val Pro Phe Lys Ala Gln Ala Gln
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Synthetic amino acid sequence
<220> FEATURE:
<221> NAME/KEY: VARIANT
<222> LOCATION: 4-6
<223> OTHER INFORMATION: Xaa = any amino acid

<400> SEQUENCE: 50

Ser Ala Gln Xaa Xaa Xaa Val Pro Phe Lys Ala Gln Ala Gln
1               5                   10

<210> SEQ ID NO 51
<211> LENGTH: 14
<212> TYPE: PRT
<213> ORGANISM: Artificial Sequence
<220> FEATURE:
<223> OTHER INFORMATION: Synthetic amino acid sequence
<220> FEATURE:
<221> NAME/KEY: VARIANT
<222> LOCATION: 6-8
<223> OTHER INFORMATION: Xaa = any amino acid

<400> SEQUENCE: 51

Ser Ala Gln Thr Leu Xaa Xaa Xaa Phe Lys Ala Gln Ala Gln
1               5                   10

<210> SEQ ID NO 52
<211> LENGTH: 14
<212> TYPE: PRT
<213> ORGANISM: Artificial Sequence
<220> FEATURE:
```

<223> OTHER INFORMATION: Synthetic amino acid sequence
<220> FEATURE:
<221> NAME/KEY: VARIANT
<222> LOCATION: 8-10
<223> OTHER INFORMATION: Xaa = any amino acid

<400> SEQUENCE: 52

Ser Ala Gln Thr Leu Ala Val Xaa Xaa Xaa Ala Gln Ala Gln
1               5                   10

<210> SEQ ID NO 53
<211> LENGTH: 14
<212> TYPE: PRT
<213> ORGANISM: Artificial Sequence
<220> FEATURE:
<223> OTHER INFORMATION: Synthetic amino acid sequence
<220> FEATURE:
<221> NAME/KEY: VARIANT
<222> LOCATION: 10-12
<223> OTHER INFORMATION: Xaa = any amino acid

<400> SEQUENCE: 53

Ser Ala Gln Thr Leu Ala Val Pro Phe Xaa Xaa Xaa Ala Gln
1               5                   10

<210> SEQ ID NO 54
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 54
gatgggactt tggcggtgcc ttttaaggca cag                    33

<210> SEQ ID NO 55
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 55
gatgggacgt tggcggtgcc ttttaaggca cag                    33

<210> SEQ ID NO 56
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 56
caggcggtta ggacgtcttt g                                 21

<210> SEQ ID NO 57
<211> LENGTH: 27
<212> TYPE: DNA
<213> ORGANISM: Artificial Sequence
<220> FEATURE:
<223> OTHER INFORMATION: Synthetic nucleotide sequence

<400> SEQUENCE: 57
caggtcttca cggactcaga ctatcag                           27

<210> SEQ ID NO 58
<211> LENGTH: 32

```
<212> TYPE: DNA
<213> ORGANISM: Artificial Sequence
<220> FEATURE:
<223> OTHER INFORMATION: Synthetic nucleotide sequence

<400> SEQUENCE: 58
caagtaaaac ctctacaaat gtggtaaaat cg                                  32

<210> SEQ ID NO 59
<211> LENGTH: 36
<212> TYPE: DNA
<213> ORGANISM: Artificial Sequence
<220> FEATURE:
<223> OTHER INFORMATION: Synthetic nucleotide sequence

<400> SEQUENCE: 59
actcatcgac caatacttgt actatctctc tagaac                              36

<210> SEQ ID NO 60
<211> LENGTH: 26
<212> TYPE: DNA
<213> ORGANISM: Artificial Sequence
<220> FEATURE:
<223> OTHER INFORMATION: Synthetic nucleotide sequence

<400> SEQUENCE: 60
ggaagtattc cttggttttg aaccca                                         26

<210> SEQ ID NO 61
<211> LENGTH: 23
<212> TYPE: DNA
<213> ORGANISM: Artificial Sequence
<220> FEATURE:
<223> OTHER INFORMATION: Synthetic nucleotide sequence

<400> SEQUENCE: 61
ggtcgcggtt cttgtttgtg gat                                            23

<210> SEQ ID NO 62
<211> LENGTH: 24
<212> TYPE: DNA
<213> ORGANISM: Artificial Sequence
<220> FEATURE:
<223> OTHER INFORMATION: Synthetic nucleotide sequence

<400> SEQUENCE: 62
cgaccttgaa gcgcatgaac tcct                                           24

<210> SEQ ID NO 63
<211> LENGTH: 83
<212> TYPE: DNA
<213> ORGANISM: Artificial Sequence
<220> FEATURE:
<223> OTHER INFORMATION: Synthetic nucleotide sequence
<220> FEATURE:
<221> NAME/KEY: misc_feature
<222> LOCATION: 42, 43, 45, 46, 48, 49, 51, 52, 54, 55, 57, 58, 60, 61
<223> OTHER INFORMATION: n = a, c, t or g

<400> SEQUENCE: 63
gtattccttg gttttgaacc caaccggtct gcgcctgtgc mnnmnnmnnm nnmnnmnnmn    60
nttgggcact ctggtggttt gtc                                            83

<210> SEQ ID NO 64

<400> SEQUENCE: 64
```

```
<210> SEQ ID NO 65
<211> LENGTH: 7
<212> TYPE: PRT
<213> ORGANISM: Artificial Sequence
<220> FEATURE:
<223> OTHER INFORMATION: Synthetic amino acid sequence

<400> SEQUENCE: 65

Thr Asn His Gln Ser Ala Gln
1               5

<210> SEQ ID NO 66
<211> LENGTH: 7
<212> TYPE: PRT
<213> ORGANISM: Artificial Sequence
<220> FEATURE:
<223> OTHER INFORMATION: Synthetic amino acid sequence

<400> SEQUENCE: 66

Ala Gln Ala Gln Thr Gly Trp
1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic amino acid sequence

<400> SEQUENCE: 67

Asp Gly Thr Leu Ala Thr Pro Phe Lys
1               5

<210> SEQ ID NO 68
<211> LENGTH: 11
<212> TYPE: PRT
<213> ORGANISM: Artificial Sequence
<220> FEATURE:
<223> OTHER INFORMATION: Synthetic amino acid sequence
<220> FEATURE:
<221> NAME/KEY: VARIANT
<222> LOCATION: 10-11
<223> OTHER INFORMATION: Xaa = any amino acid

<400> SEQUENCE: 68

Asp Gly Thr Leu Ala Thr Pro Phe Lys Xaa Xaa
1               5                   10

<210> SEQ ID NO 69
<211> LENGTH: 64
<212> TYPE: DNA
<213> ORGANISM: Artificial Sequence
<220> FEATURE:
<223> OTHER INFORMATION: Synthetic nucleotide sequence
<220> FEATURE:
<221> NAME/KEY: misc_feature
<222> LOCATION: 36, 37, 39, 40, 42, 43
<223> OTHER INFORMATION: n = a, c, t or g

<400> SEQUENCE: 69
gtattccttg gttttgaacc caaccggtct gcgcmnnmnn mnnaaaaggc accgccaaag    60
tttg                                                                64

<210> SEQ ID NO 70
```

-continued

```
<211> LENGTH: 70
<212> TYPE: DNA
<213> ORGANISM: Artificial Sequence
<220> FEATURE:
<223> OTHER INFORMATION: Synthetic nucleotide sequence
<220> FEATURE:
<221> NAME/KEY: misc_feature
<222> LOCATION: 42, 43, 45, 46, 48, 49
<223> OTHER INFORMATION: n = a, c, t or g

<400> SEQUENCE: 70
gtattccttg gttttgaacc caaccggtct gcgcctgtgc mnnmnnmnnc accgccaaag      60
tttgggcact                                                             70

<210> SEQ ID NO 71
<211> LENGTH: 77
<212> TYPE: DNA
<213> ORGANISM: Artificial Sequence
<220> FEATURE:
<223> OTHER INFORMATION: Synthetic nucleotide sequence
<220> FEATURE:
<221> NAME/KEY: misc_feature
<222> LOCATION: 48, 49, 51, 52, 54, 55
<223> OTHER INFORMATION: n = a, c, t or g

<400> SEQUENCE: 71
gtattccttg gttttgaacc caaccggtct gcgcctgtgc cttaaamnnm nnmnncaaag      60
tttgggcact ctggtgg                                                     77

<210> SEQ ID NO 72
<211> LENGTH: 83
<212> TYPE: DNA
<213> ORGANISM: Artificial Sequence
<220> FEATURE:
<223> OTHER INFORMATION: Synthetic nucleotide sequence
<220> FEATURE:
<221> NAME/KEY: misc_feature
<222> LOCATION: 54, 55, 57, 58, 60, 61
<223> OTHER INFORMATION: n = a, c, t or g

<400> SEQUENCE: 72
gtattccttg gttttgaacc caaccggtct gcgcctgtgc cttaaaaggc acmnnmnnmn      60
nttgggcact ctggtggttt gtg                                              83

<210> SEQ ID NO 73
<211> LENGTH: 90
<212> TYPE: DNA
<213> ORGANISM: Artificial Sequence
<220> FEATURE:
<223> OTHER INFORMATION: Reverse primer sequence used to generate the
      AAV-PHP.B-XXX libraries
<220> FEATURE:
<221> NAME/KEY: misc_feature
<222> LOCATION: 57, 58, 60, 61, 63, 64
<223> OTHER INFORMATION: n = a, c, t or g

<400> SEQUENCE: 73
ttccttggtt ttgaacccaa ccggtctgcg cctgtgcctt aaaaggcacc gccaamnnmn      60
nmnnactctg gtggtttgtg gccacttgtc                                       90

<210> SEQ ID NO 74
<211> LENGTH: 21
<212> TYPE: DNA
<213> ORGANISM: Artificial Sequence
<220> FEATURE:
<223> OTHER INFORMATION: Synthetic nucleotide sequence
```

<400> SEQUENCE: 74
actttggcgg tgccttttaa g                                                    21

<210> SEQ ID NO 75
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 75
agtgtgagta agccttttttt g                                                   21

<210> SEQ ID NO 76
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 76
tttacgttga cgacgcctaa g                                                    21

<210> SEQ ID NO 77
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 77
tatactttgt cgcagggttg g                                                    21

<210> SEQ ID NO 78
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 78
caggcggtta ggacgtcttt g                                                    21

<210> SEQ ID NO 79
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 79
cttgcgaagg agcggctttc g                                                    21

<210> SEQ ID NO 80
<211> LENGTH: 8
<212> TYPE: PRT
<213> ORGANISM: Artificial Sequence
<220> FEATURE:
<223> OTHER INFORMATION: Synthetic amino acid sequence

<400> SEQUENCE: 80

Leu Ala Val Pro Phe Lys Ala Gln
1               5

<210> SEQ ID NO 81

```
<211> LENGTH: 6
<212> TYPE: PRT
<213> ORGANISM: Artificial Sequence
<220> FEATURE:
<223> OTHER INFORMATION: Synthetic amino acid sequence

<400> SEQUENCE: 81

Val Pro Phe Lys Ala Gln
1               5

<210> SEQ ID NO 82
<211> LENGTH: 4
<212> TYPE: PRT
<213> ORGANISM: Artificial Sequence
<220> FEATURE:
<223> OTHER INFORMATION: Synthetic amino acid sequence

<400> SEQUENCE: 82

Phe Lys Ala Gln
1

<210> SEQ ID NO 83
<211> LENGTH: 6
<212> TYPE: PRT
<213> ORGANISM: Artificial Sequence
<220> FEATURE:
<223> OTHER INFORMATION: Synthetic amino acid sequence

<400> SEQUENCE: 83

Ala Gln Thr Leu Ala Val
1               5

<210> SEQ ID NO 84
<211> LENGTH: 8
<212> TYPE: PRT
<213> ORGANISM: Artificial Sequence
<220> FEATURE:
<223> OTHER INFORMATION: Synthetic amino acid sequence

<400> SEQUENCE: 84

Ala Gln Thr Leu Ala Val Pro Phe
1               5

<210> SEQ ID NO 85
<211> LENGTH: 4
<212> TYPE: PRT
<213> ORGANISM: Artificial Sequence
<220> FEATURE:
<223> OTHER INFORMATION: Synthetic amino acid sequence

<400> SEQUENCE: 85

Gln Ala Val Arg
1

<210> SEQ ID NO 86
<211> LENGTH: 4
<212> TYPE: PRT
<213> ORGANISM: Artificial Sequence
<220> FEATURE:
<223> OTHER INFORMATION: Synthetic amino acid sequence

<400> SEQUENCE: 86

Ala Val Arg Thr
1

<210> SEQ ID NO 87
<211> LENGTH: 4
```

```
<212> TYPE: PRT
<213> ORGANISM: Artificial Sequence
<220> FEATURE:
<223> OTHER INFORMATION: Synthetic amino acid sequence

<400> SEQUENCE: 87

Val Arg Thr Ser
1

<210> SEQ ID NO 88
<211> LENGTH: 4
<212> TYPE: PRT
<213> ORGANISM: Artificial Sequence
<220> FEATURE:
<223> OTHER INFORMATION: Synthetic amino acid sequence

<400> SEQUENCE: 88

Arg Thr Ser Leu
1

<210> SEQ ID NO 89
<211> LENGTH: 5
<212> TYPE: PRT
<213> ORGANISM: Artificial Sequence
<220> FEATURE:
<223> OTHER INFORMATION: Synthetic amino acid sequence

<400> SEQUENCE: 89

Gln Ala Val Arg Thr
1               5

<210> SEQ ID NO 90
<211> LENGTH: 5
<212> TYPE: PRT
<213> ORGANISM: Artificial Sequence
<220> FEATURE:
<223> OTHER INFORMATION: Synthetic amino acid sequence

<400> SEQUENCE: 90

Ala Val Arg Thr Ser
1               5

<210> SEQ ID NO 91
<211> LENGTH: 5
<212> TYPE: PRT
<213> ORGANISM: Artificial Sequence
<220> FEATURE:
<223> OTHER INFORMATION: Synthetic amino acid sequence

<400> SEQUENCE: 91

Val Arg Thr Ser Leu
1               5

<210> SEQ ID NO 92
<211> LENGTH: 6
<212> TYPE: PRT
<213> ORGANISM: Artificial Sequence
<220> FEATURE:
<223> OTHER INFORMATION: Synthetic amino acid sequence

<400> SEQUENCE: 92

Gln Ala Val Arg Thr Ser
1               5

<210> SEQ ID NO 93
<211> LENGTH: 6
<212> TYPE: PRT
```

```
<213> ORGANISM: Artificial Sequence
<220> FEATURE:
<223> OTHER INFORMATION: Synthetic amino acid sequence

<400> SEQUENCE: 93

Ala Val Arg Thr Ser Leu
1               5
```